(12) United States Patent
Matsui et al.

(10) Patent No.: US 7,846,704 B2
(45) Date of Patent: Dec. 7, 2010

(54) FLAP ENDONUCLEASE MUTANTS

(75) Inventors: Eriko Matsui, Ibaraki (JP); Ikuo Matsui, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 524 days.

(21) Appl. No.: 11/658,096

(22) PCT Filed: Jan. 21, 2005

(86) PCT No.: PCT/JP2005/000792

§ 371 (c)(1),
(2), (4) Date: Aug. 16, 2007

(87) PCT Pub. No.: WO2006/011253

PCT Pub. Date: Feb. 2, 2006

(65) Prior Publication Data

US 2008/0118922 A1    May 22, 2008

(30) Foreign Application Priority Data

Jul. 23, 2004   (JP)   .............................. 2004-216527

(51) Int. Cl.
| | |
|---|---|
| C12N 9/16 | (2006.01) |
| C07K 14/00 | (2006.01) |
| C12N 15/00 | (2006.01) |
| C12P 21/00 | (2006.01) |
| C12Q 1/44 | (2006.01) |
| C12N 1/21 | (2006.01) |
| C12N 5/10 | (2006.01) |
| C07H 21/00 | (2006.01) |

(52) U.S. Cl. ....................... 435/196; 435/19; 435/320.1; 435/69.1; 435/252.3; 435/325; 530/350; 536/23.2

(58) Field of Classification Search ................. 435/196, 435/320.1, 69.1, 19, 252.3, 325; 530/350; 536/23.2
See application file for complete search history.

(56) References Cited

PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Eriko Matsui, et al, "Aromatic Residues Located Close to the Active Center are Essential for the Catalytic Reaction of Flap Endonuclease-1 From Hyperthermophilic Archaeon *Pyrococcus Horikoshii*", The Journal of Biological Chemistry, vol. 279, No. 16, 2004, pp. 16687-16696.
Tony M. Hsu, et al, "Genotyping Single-Nucleotide Polymorphisms by the Invader Assay With Dual-Color Fluorescence Polarization Detection", Clinical Chemistry, vol. 47, No. 8, 2001, p. 1373-1377.
Junzhuan Qiu, et al, "Interaction Interface of Human Flap Endonuclease-1 With its DNA Substrates", The Journal of Biological Chemistry, vol. 279, No. 23, 2004, pp. 24394-24402.
Binghui Shen, et al, "Essential Amino Acids for Substrate Binding and Catalysis of Human Flap Endonuclease 1", The Journal of Biological Chemistry, vol. 271, No. 16, 1996, pp. 9173-9176.

* cited by examiner

*Primary Examiner*—Delia M Ramirez
(74) *Attorney, Agent, or Firm*—Sughrue Mion, PLLC

(57) ABSTRACT

A mutation is introduced into the substrate-binding site of flap endonuclease to prepare a mutant with modified substrate specificity. Using the mutant as a reagent for the analysis of genetic polymorphism, the analysis of genetic polymorphism can be performed more accurately, easily and sensitively as compared with conventional methods.

2 Claims, 27 Drawing Sheets

Comparison of Km, Kcat and Kcat/Km of the mutants in each substrate

Comparison of Kcat/Km of the mutants in each substrate $k_{cat}/K_m (10^6 s^{-1} M^{-1})$ (1)
In the presence of SNP In the absence of SNP (2)
In the presence of SNP In the absence of SNP (3)
Sequencing of SNP (A) Single Flap with 5' 1mer projection (B) nick with 3' projection (C) Double flap with gap at junction (A) Single flap with 5' 1mer projection (B, B') Double flap with gap at junction (C) Nick with 3' projection

Fig. 14

(A) Nick with 3' projection

Template Strand(A)

Downstream 3' Upstream
Strand(C-1)   Strand(B-2)

(B) Double flap with gap at junction

Template Strand(A)

Flap      5' 3' Upstream
Strand(C-4)   Strand(B-3)

(C) Single flap with 5' 1mer projection

Template Strand(A)

Flap       Upstream
Strand(C-4) 5' Strand(B-1)

(A) Nick with 3' projection (B) Single flap with 5' 1mer projection

SEQUENCE LISTING

<160> NUMBER OF SEQ ID NOS: 54

<210> SEQ ID NO 1
<211> LENGTH: 1032
<212> TYPE: DNA
<213> ORGANISM: Pyrococcus horikoshii
<220> FEATURE:
<221> NAME/KEY: CDS
<222> LOCATION: (1)..(1029)

<400> SEQUENCE: 1

```
atg ggt gtt cct atc ggt gac ctc gtt ccg cgc aag gag atc gac ctt       48
Met Gly Val Pro Ile Gly Asp Leu Val Pro Arg Lys Glu Ile Asp Leu
1               5                   10                  15 gaa aat ctg tat gga aag aag ata gcg ata gat gcc cta aac gcc atc       96
Glu Asn Leu Tyr Gly Lys Lys Ile Ala Ile Asp Ala Leu Asn Ala Ile
                20                  25                  30 tat cag ttt tta tca acg ata cga cag cgt gat gga aca cca ctt atg      144
Tyr Gln Phe Leu Ser Thr Ile Arg Gln Arg Asp Gly Thr Pro Leu Met
            35                  40                  45 gac tct ggc ggt agg ata acc tct cat tta agt ggg ctc ttt tat aga      192
Asp Ser Gly Gly Arg Ile Thr Ser His Leu Ser Gly Leu Phe Tyr Arg
        50                  55                  60 acg ata aat cta atg gaa gcc ggt att aag ccg gcc tac gtc ttt gat      240
Thr Ile Asn Leu Met Glu Ala Gly Ile Lys Pro Ala Tyr Val Phe Asp
65                  70                  75                  80 gga aag cct ccg gaa ttt aaa cgc aag gaa cta gaa aaa cgc cgt gaa      288
```

```
                                                      -continued

Gly Lys Pro Pro Glu Phe Lys Arg Lys Glu Leu Glu Lys Arg Arg Glu
            85                  90                  95 gct cgt gaa gag gca gaa cta aaa tgg aaa gaa gct cta gcc aag gga       336
Ala Arg Glu Glu Ala Glu Leu Lys Trp Lys Glu Ala Leu Ala Lys Gly
        100                 105                 110 aac ctg gag gaa gct agg aaa tac gct caa agg gca act aag gtt aat       384
Asn Leu Glu Glu Ala Arg Lys Tyr Ala Gln Arg Ala Thr Lys Val Asn
    115                 120                 125 gaa atg cta atc gaa gat gca aag aag ctt ttg caa cta atg gga ata       432
Glu Met Leu Ile Glu Asp Ala Lys Lys Leu Leu Gln Leu Met Gly Ile
130                 135                 140 cca ata att cag gct cca agt gaa gga gaa gcc caa gcg gca tac atg       480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca       528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga       576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag       624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa       672
Leu Val Val Leu Asp Glu Val Leu Lys Glu Leu Lys Ile Thr Arg Glu
    210                 215                 220 aag ctt ata gaa ctt gca att ctg gtt ggg act gac tat aat cct ggg       720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat       768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt       816
Ser Arg Asp Pro Leu Ala Lys Phe Gln Arg Gln Ser Asp Val Asp Leu
            260                 265                 270 tac gct att aag gaa ttc ttc ctt aac cct cct gtc act aat gaa tac       864
Tyr Ala Ile Lys Glu Phe Phe Leu Asn Pro Pro Val Thr Asn Glu Tyr
        275                 280                 285 tcg ctt agt tgg aag gag cct gat gag gaa gga ata tta aaa ttc ctc       912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa       960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt      1008
Arg Leu Lys Lys Ala Ile Lys Ala Gly Arg Gln Ser Thr Leu Glu Ser
                325                 330                 335 tgg ttc gtt aaa aag aaa ccc taa                                      1032
Trp Phe Val Lys Lys Lys Pro
            340

<210> SEQ ID NO 2
<211> LENGTH: 343
<212> TYPE: PRT
<213> ORGANISM: Pyrococcus horikoshii

<400> SEQUENCE: 2

Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
```

|   |   | 20 |   |   |   | 25 |   |   |   | 30 |   |   |   |   |
|---|---|---|---|---|---|---|---|---|---|---|---|---|---|---|

Tyr Gln Phe Leu Ser Thr Ile Arg Gln Arg Asp Gly Thr Pro Leu Met
                35                  40                  45

Asp Ser Gly Gly Arg Ile Thr Ser His Leu Ser Gly Leu Phe Tyr Arg
 50                      55                  60

Thr Ile Asn Leu Met Glu Ala Gly Ile Lys Pro Ala Tyr Val Phe Asp
65                   70                  75                  80

Gly Lys Pro Pro Glu Phe Lys Arg Lys Glu Leu Lys Arg Arg Glu
                    85                  90                  95

Ala Arg Glu Glu Ala Glu Leu Lys Trp Lys Glu Ala Leu Ala Lys Gly
                100                 105                 110

Asn Leu Glu Glu Ala Arg Lys Tyr Ala Gln Arg Ala Thr Lys Val Asn
            115                 120                 125

Glu Met Leu Ile Glu Asp Ala Lys Lys Leu Leu Gln Leu Met Gly Ile
        130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Lys Pro
            340

<210> SEQ ID NO 3
<211> LENGTH: 1032
<212> TYPE: DNA
<213> ORGANISM: Artificial Sequence
<220> FEATURE:
<223> OTHER INFORMATION: Flap endonuclease mutant (Y33A)
<220> FEATURE:
<221> NAME/KEY: CDS
<222> LOCATION: (1)..(1029)

<400> SEQUENCE: 3 atg ggt gtt cct atc ggt gac ctc gtt ccg cgc aag gag atc gac ctt     48
Met Gly Val Pro Ile Gly Asp Leu Val Pro Arg Lys Glu Ile Asp Leu
 1               5                  10                  15

-continued

| | | |
|---|---|---|
| gaa aat ctg tat gga aag aag ata gcg ata gat gcc cta aac gcc atc<br>Glu Asn Leu Tyr Gly Lys Lys Ile Ala Ile Asp Ala Leu Asn Ala Ile<br>        20                      25                      30 | 96 |
| gcg cag ttt tta tca acg ata cga cag cgt gat gga aca cca ctt atg<br>Ala Gln Phe Leu Ser Thr Ile Arg Gln Arg Asp Gly Thr Pro Leu Met<br>      35                    40                      45 | 144 |
| gac tct ggc ggt agg ata acc tct cat tta agt ggg ctc ttt tat aga<br>Asp Ser Gly Gly Arg Ile Thr Ser His Leu Ser Gly Leu Phe Tyr Arg<br>50                      55                      60 | 192 |
| acg ata aat cta atg gaa gcc ggt att aag ccg gcc tac gtc ttt gat<br>Thr Ile Asn Leu Met Glu Ala Gly Ile Lys Pro Ala Tyr Val Phe Asp<br>65                      70                      75                      80 | 240 |
| gga aag cct ccg gaa ttt aaa cgc aag gaa cta gaa aaa cgc cgt gaa<br>Gly Lys Pro Pro Glu Phe Lys Arg Lys Glu Leu Glu Lys Arg Arg Glu<br>                      85                      90                      95 | 288 |
| gct cgt gaa gag gca gaa cta aaa tgg aaa gaa gct cta gcc aag gga<br>Ala Arg Glu Glu Ala Glu Leu Lys Trp Lys Glu Ala Leu Ala Lys Gly<br>                      100                   105                 110 | 336 |
| aac ctg gag gaa gct agg aaa tac gct caa agg gca act aag gtt aat<br>Asn Leu Glu Glu Ala Arg Lys Tyr Ala Gln Arg Ala Thr Lys Val Asn<br>               115                 120                 125 | 384 |
| gaa atg cta atc gaa gat gca aag aag ctt ttg caa cta atg gga ata<br>Glu Met Leu Ile Glu Asp Ala Lys Lys Leu Leu Gln Leu Met Gly Ile<br>130                      135                      140 | 432 |
| cca ata att cag gct cca agt gaa gga gaa gcc caa gcg gca tac atg<br>Pro Ile Ile Gln Ala Pro Ser Glu Gly Glu Ala Gln Ala Ala Tyr Met<br>145                      150                   155                 160 | 480 |
| gca agt aaa ggg gat gtc tac gcg tca gcg agt caa gat tat gat tca<br>Ala Ser Lys Gly Asp Val Tyr Ala Ser Ala Ser Gln Asp Tyr Asp Ser<br>                      165                   170                 175 | 528 |
| cta ctc ttt ggt gct cca agg ttg att agg aat ctg aca att acg gga<br>Leu Leu Phe Gly Ala Pro Arg Leu Ile Arg Asn Leu Thr Ile Thr Gly<br>                      180                   185                 190 | 576 |
| aaa aga aag atg cct ggg aaa gat gtt tac gtt gaa ata aag cca gag<br>Lys Arg Lys Met Pro Gly Lys Asp Val Tyr Val Glu Ile Lys Pro Glu<br>195                      200                   205 | 624 |
| tta gta gtt cta gat gag gta cta aaa gag ctt aag ata aca aga gaa<br>Leu Val Val Leu Asp Glu Val Leu Lys Glu Leu Lys Ile Thr Arg Glu<br>210                      215                      220 | 672 |
| aag ctt ata gaa ctt gca att ctg gtt ggg act gac tat aat cct ggg<br>Lys Leu Ile Glu Leu Ala Ile Leu Val Gly Thr Asp Tyr Asn Pro Gly<br>225                      230                   235                 240 | 720 |
| ggc gta aag ggg ata gga cct aag aag gcc ctt gag att gta aga tat<br>Gly Val Lys Gly Ile Gly Pro Lys Lys Ala Leu Glu Ile Val Arg Tyr<br>                      245                   250                 255 | 768 |
| tca agg gat ccc cta gca aag ttc caa aga cag agc gat gtg gat ctt<br>Ser Arg Asp Pro Leu Ala Lys Phe Gln Arg Gln Ser Asp Val Asp Leu<br>                      260                   265                 270 | 816 |
| tac gct att aag gaa ttc ttc ctt aac cct cct gtc act aat gaa tac<br>Tyr Ala Ile Lys Glu Phe Phe Leu Asn Pro Pro Val Thr Asn Glu Tyr<br>275                      280                   285 | 864 |
| tcg ctt agt tgg aag gag cct gat gag gaa gga ata tta aaa ttc ctc<br>Ser Leu Ser Trp Lys Glu Pro Asp Glu Glu Gly Ile Leu Lys Phe Leu<br>                      290                   295                 300 | 912 |
| tgt gat gag cat aat ttt agc gaa gaa agg gta aaa aat ggg ata gaa<br>Cys Asp Glu His Asn Phe Ser Glu Glu Arg Val Lys Asn Gly Ile Glu<br>305                      310                   315                 320 | 960 |
| aga cta aaa aag gcg ata aaa gct gga aga caa tca acg ctt gag agt<br>Arg Leu Lys Lys Ala Ile Lys Ala Gly Arg Gln Ser Thr Leu Glu Ser<br>                      325                   330                 335 | 1008 |

```
tgg ttc gtt aaa aag aaa ccc taa                                    1032
Trp Phe Val Lys Lys Lys Pro
            340

<210> SEQ ID NO 4
<211> LENGTH: 343
<212> TYPE: PRT
<213> ORGANISM: Artificial Sequence
<220> FEATURE:
<223> OTHER INFORMATION: Flap endonuclease mutant (Y33A)

<400> SEQUENCE: 4

Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Ala Gln Phe Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Lys Pro
```

-continued

340

<210> SEQ ID NO 5
<211> LENGTH: 1032
<212> TYPE: DNA
<213> ORGANISM: Artificial Sequence
<220> FEATURE:
<223> OTHER INFORMATION: Flap endonuclease mutant (Y33L)
<220> FEATURE:
<221> NAME/KEY: CDS
<222> LOCATION: (1)..(1029)

<400> SEQUENCE: 5

```
atg ggt gtt cct atc ggt gac ctc gtt ccg cgc aag gag atc gac ctt      48
Met Gly Val Pro Ile Gly Asp Leu Val Pro Arg Lys Glu Ile Asp Leu
1               5                   10                  15 gaa aat ctg tat gga aag aag ata gcg ata gat gcc cta aac gcc atc      96
Glu Asn Leu Tyr Gly Lys Lys Ile Ala Ile Asp Ala Leu Asn Ala Ile
            20                  25                  30 ctg cag ttt tta tca acg ata cga cag cgt gat gga aca cca ctt atg     144
Leu Gln Phe Leu Ser Thr Ile Arg Gln Arg Asp Gly Thr Pro Leu Met
        35                  40                  45 gac tct ggc ggt agg ata acc tct cat tta agt ggg ctc ttt tat aga     192
Asp Ser Gly Gly Arg Ile Thr Ser His Leu Ser Gly Leu Phe Tyr Arg
    50                  55                  60 acg ata aat cta atg gaa gcc ggt att aag ccg gcc tac gtc ttt gat     240
Thr Ile Asn Leu Met Glu Ala Gly Ile Lys Pro Ala Tyr Val Phe Asp
65                  70                  75                  80 gga aag cct ccg gaa ttt aaa cgc aag gaa cta gaa aaa cgc cgt gaa     288
Gly Lys Pro Pro Glu Phe Lys Arg Lys Glu Leu Glu Lys Arg Arg Glu
                85                  90                  95 gct cgt gaa gag gca gaa cta aaa tgg aaa gaa gct cta gcc aag gga     336
Ala Arg Glu Glu Ala Glu Leu Lys Trp Lys Glu Ala Leu Ala Lys Gly
            100                 105                 110 aac ctg gag gaa gct agg aaa tac gct caa agg gca act aag gtt aat     384
Asn Leu Glu Glu Ala Arg Lys Tyr Ala Gln Arg Ala Thr Lys Val Asn
        115                 120                 125 gaa atg cta atc gaa gat gca aag aag ctt ttg caa cta atg gga ata     432
Glu Met Leu Ile Glu Asp Ala Lys Lys Leu Leu Gln Leu Met Gly Ile
    130                 135                 140 cca ata att cag gct cca agt gaa gga gaa gcc caa gcg gca tac atg     480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca     528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga     576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag     624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa     672
Leu Val Val Leu Asp Glu Val Leu Lys Glu Leu Lys Ile Thr Arg Glu
    210                 215                 220 aag ctt ata gaa ctt gca att ctg gtt ggg act gac tat aat cct ggg     720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat     768
Gly Val Lys Gly Ile Gly Pro Lys Lys Ala Leu Glu Ile Val Arg Tyr
                245                 250                 255
```

-continued

```
tca agg gat ccc cta gca aag ttc caa aga cag agc gat gtg gat ctt    816
Ser Arg Asp Pro Leu Ala Lys Phe Gln Arg Gln Ser Asp Val Asp Leu
        260                 265                 270 tac gct att aag gaa ttc ttc ctt aac cct cct gtc act aat gaa tac    864
Tyr Ala Ile Lys Glu Phe Phe Leu Asn Pro Pro Val Thr Asn Glu Tyr
275                 280                 285 tcg ctt agt tgg aag gag cct gat gag gaa gga ata tta aaa ttc ctc    912
Ser Leu Ser Trp Lys Glu Pro Asp Glu Glu Gly Ile Leu Lys Phe Leu
        290                 295                 300 tgt gat gag cat aat ttt agc gaa gaa agg gta aaa aat ggg ata gaa    960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt   1008
Arg Leu Lys Lys Ala Ile Lys Ala Gly Arg Gln Ser Thr Leu Glu Ser
                325                 330                 335 tgg ttc gtt aaa aag aaa ccc taa                                   1032
Trp Phe Val Lys Lys Lys Pro
                340
```

<210> SEQ ID NO 6
<211> LENGTH: 343
<212> TYPE: PRT
<213> ORGANISM: Artificial Sequence
<220> FEATURE:
<223> OTHER INFORMATION: Flap endonuclease mutant (Y33L)

<400> SEQUENCE: 6

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Leu Gln Phe Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240
```

```
Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Pro
            340

<210> SEQ ID NO 7
<211> LENGTH: 1032
<212> TYPE: DNA
<213> ORGANISM: Artificial Sequence
<220> FEATURE:
<223> OTHER INFORMATION: Flap endonuclease mutant(F35Y)
<220> FEATURE:
<221> NAME/KEY: CDS
<222> LOCATION: (1)..(1029)

<400> SEQUENCE: 7
```

| | | | | | | | | | | | | | | | | |
|---|---|---|---|---|---|---|---|---|---|---|---|---|---|---|---|---|
| atg | ggt | gtt | cct | atc | ggt | gac | ctc | gtt | ccg | cgc | aag | gag | atc | gac | ctt | 48 |
| Met | Gly | Val | Pro | Ile | Gly | Asp | Leu | Val | Pro | Arg | Lys | Glu | Ile | Asp | Leu | |
| 1 | | | | 5 | | | | | 10 | | | | | 15 | | |
| gaa | aat | ctg | tat | gga | aag | aag | ata | gcg | ata | gat | gcc | cta | aac | gcc | atc | 96 |
| Glu | Asn | Leu | Tyr | Gly | Lys | Lys | Ile | Ala | Ile | Asp | Ala | Leu | Asn | Ala | Ile | |
| | | | 20 | | | | | 25 | | | | | 30 | | | |
| tat | cag | tat | tta | tca | acg | ata | cga | cag | cgt | gat | gga | aca | cca | ctt | atg | 144 |
| Tyr | Gln | Tyr | Leu | Ser | Thr | Ile | Arg | Gln | Arg | Asp | Gly | Thr | Pro | Leu | Met | |
| | | | | 35 | | | | | 40 | | | | | 45 | | |
| gac | tct | ggc | ggt | agg | ata | acc | tct | cat | tta | agt | ggg | ctc | ttt | tat | aga | 192 |
| Asp | Ser | Gly | Gly | Arg | Ile | Thr | Ser | His | Leu | Ser | Gly | Leu | Phe | Tyr | Arg | |
| | 50 | | | | | 55 | | | | | 60 | | | | | |
| acg | ata | aat | cta | atg | gaa | gcc | ggt | att | aag | ccg | gcc | tac | gtc | ttt | gat | 240 |
| Thr | Ile | Asn | Leu | Met | Glu | Ala | Gly | Ile | Lys | Pro | Ala | Tyr | Val | Phe | Asp | |
| 65 | | | | | 70 | | | | | 75 | | | | | 80 | |
| gga | aag | cct | ccg | gaa | ttt | aaa | cgc | aag | gaa | cta | gaa | aaa | cgc | cgt | gaa | 288 |
| Gly | Lys | Pro | Pro | Glu | Phe | Lys | Arg | Lys | Glu | Leu | Glu | Lys | Arg | Arg | Glu | |
| | | | | 85 | | | | | 90 | | | | | 95 | | |
| gct | cgt | gaa | gag | gca | gaa | cta | aaa | tgg | aaa | gaa | gct | cta | gcc | aag | gga | 336 |
| Ala | Arg | Glu | Glu | Ala | Glu | Leu | Lys | Trp | Lys | Glu | Ala | Leu | Ala | Lys | Gly | |
| | | | 100 | | | | | 105 | | | | | 110 | | | |
| aac | ctg | gag | gaa | gct | agg | aaa | tac | gct | caa | agg | gca | act | aag | gtt | aat | 384 |
| Asn | Leu | Glu | Glu | Ala | Arg | Lys | Tyr | Ala | Gln | Arg | Ala | Thr | Lys | Val | Asn | |
| | | | | 115 | | | | | 120 | | | | | 125 | | |
| gaa | atg | cta | atc | gaa | gat | gca | aag | aag | ctt | ttg | caa | cta | atg | gga | ata | 432 |
| Glu | Met | Leu | Ile | Glu | Asp | Ala | Lys | Lys | Leu | Leu | Gln | Leu | Met | Gly | Ile | |
| | | 130 | | | | | 135 | | | | | 140 | | | | |
| cca | ata | att | cag | gct | cca | agt | gaa | gga | gaa | gcc | caa | gcg | gca | tac | atg | 480 |
| Pro | Ile | Ile | Gln | Ala | Pro | Ser | Glu | Gly | Glu | Ala | Gln | Ala | Ala | Tyr | Met | |
| 145 | | | | | 150 | | | | | 155 | | | | | 160 | |
| gca | agt | aaa | ggg | gat | gtc | tac | gcg | tca | gcg | agt | caa | gat | tat | gat | tca | 528 |
| Ala | Ser | Lys | Gly | Asp | Val | Tyr | Ala | Ser | Ala | Ser | Gln | Asp | Tyr | Asp | Ser | |
| | | | | 165 | | | | | 170 | | | | | 175 | | |
| cta | ctc | ttt | ggt | gct | cca | agg | ttg | att | agg | aat | ctg | aca | att | acg | gga | 576 |

```
                                                                              624
aaa aga aag atg cct ggg aaa gat gtt tac gtt gaa ata aag cca gag
Lys Arg Lys Met Pro Gly Lys Asp Val Tyr Val Glu Ile Lys Pro Glu
        195                 200                 205

672
tta gta gtt cta gat gag gta cta aaa gag ctt aag ata aca aga gaa
Leu Val Val Leu Asp Glu Val Leu Lys Glu Leu Lys Ile Thr Arg Glu
    210                 215                 220

720
aag ctt ata gaa ctt gca att ctg gtt ggg act gac tat aat cct ggg
Lys Leu Ile Glu Leu Ala Ile Leu Val Gly Thr Asp Tyr Asn Pro Gly
225                 230                 235                 240

768
ggc gta aag ggg ata gga cct aag aag gcc ctt gag att gta aga tat
Gly Val Lys Gly Ile Gly Pro Lys Lys Ala Leu Glu Ile Val Arg Tyr
        245                 250                 255

816
tca agg gat ccc cta gca aag ttc caa aga cag agc gat gtg gat ctt
Ser Arg Asp Pro Leu Ala Lys Phe Gln Arg Gln Ser Asp Val Asp Leu
    260                 265                 270

864
tac gct att aag gaa ttc ttc ctt aac cct cct gtc act aat gaa tac
Tyr Ala Ile Lys Glu Phe Phe Leu Asn Pro Pro Val Thr Asn Glu Tyr
275                 280                 285

912
tcg ctt agt tgg aag gag cct gat gag gaa gga ata tta aaa ttc ctc
Ser Leu Ser Trp Lys Glu Pro Asp Glu Glu Gly Ile Leu Lys Phe Leu
        290                 295                 300

960
tgt gat gag cat aat ttt agc gaa gaa agg gta aaa aat ggg ata gaa
Cys Asp Glu His Asn Phe Ser Glu Glu Arg Val Lys Asn Gly Ile Glu
305                 310                 315                 320

1008
aga cta aaa aag gcg ata aaa gct gga aga caa tca acg ctt gag agt
Arg Leu Lys Lys Ala Ile Lys Ala Gly Arg Gln Ser Thr Leu Glu Ser
            325                 330                 335

1032
tgg ttc gtt aaa aag aaa ccc taa
Trp Phe Val Lys Lys Lys Pro
            340
```

<210> SEQ ID NO 8
<211> LENGTH: 343
<212> TYPE: PRT
<213> ORGANISM: Artificial Sequence
<220> FEATURE:
<223> OTHER INFORMATION: Flap endonuclease mutant(F35Y)

<400> SEQUENCE: 8

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Tyr Gln Tyr Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140
```

```
Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Pro
            340

<210> SEQ ID NO 9
<211> LENGTH: 1032
<212> TYPE: DNA
<213> ORGANISM: Artificial Sequence
<220> FEATURE:
<223> OTHER INFORMATION: Flap endonuclease mutant(F79A)
<220> FEATURE:
<221> NAME/KEY: CDS
<222> LOCATION: (1)..(1029)

<400> SEQUENCE: 9 atg ggt gtt cct atc ggt gac ctc gtt ccg cgc aag gag atc gac ctt     48
Met Gly Val Pro Ile Gly Asp Leu Val Pro Arg Lys Glu Ile Asp Leu
1               5                   10                  15 gaa aat ctg tat gga aag aag ata gcg ata gat gcc cta aac gcc atc     96
Glu Asn Leu Tyr Gly Lys Lys Ile Ala Ile Asp Ala Leu Asn Ala Ile
            20                  25                  30 tat cag ttt tta tca acg ata cga cag cgt gat gga aca cca ctt atg    144
Tyr Gln Phe Leu Ser Thr Ile Arg Gln Arg Asp Gly Thr Pro Leu Met
        35                  40                  45 gac tct ggc ggt agg ata acc tct cat tta agt ggg ctc ttt tat aga    192
Asp Ser Gly Gly Arg Ile Thr Ser His Leu Ser Gly Leu Phe Tyr Arg
    50                  55                  60 acg ata aat cta atg gaa gcc ggt att aag ccg gcc tac gtc gcg gat    240
Thr Ile Asn Leu Met Glu Ala Gly Ile Lys Pro Ala Tyr Val Ala Asp
65                  70                  75                  80 gga aag cct ccg gaa ttt aaa cgc aag gaa cta gaa aaa cgc cgt gaa    288
Gly Lys Pro Pro Glu Phe Lys Arg Lys Glu Leu Glu Lys Arg Arg Glu
                85                  90                  95 gct cgt gaa gag gca gaa cta aaa tgg aaa gaa gct cta gcc aag gga    336
Ala Arg Glu Glu Ala Glu Leu Lys Trp Lys Glu Ala Leu Ala Lys Gly
```

```
                    100                 105                 110
aac ctg gag gaa gct agg aaa tac gct caa agg gca act aag gtt aat    384
Asn Leu Glu Glu Ala Arg Lys Tyr Ala Gln Arg Ala Thr Lys Val Asn
        115                 120                 125 gaa atg cta atc gaa gat gca aag aag ctt ttg caa cta atg gga ata    432
Glu Met Leu Ile Glu Asp Ala Lys Lys Leu Leu Gln Leu Met Gly Ile
130                 135                 140 cca ata att cag gct cca agt gaa gga gaa gcc caa gcg gca tac atg    480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca    528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga    576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag    624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa    672
Leu Val Val Leu Asp Glu Val Leu Lys Glu Leu Lys Ile Thr Arg Glu
    210                 215                 220 aag ctt ata gaa ctt gca att ctg gtt ggg act gac tat aat cct ggg    720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat    768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt    816
Ser Arg Asp Pro Leu Ala Lys Phe Gln Arg Gln Ser Asp Val Asp Leu
            260                 265                 270 tac gct att aag gaa ttc ttc ctt aac cct cct gtc act aat gaa tac    864
Tyr Ala Ile Lys Glu Phe Phe Leu Asn Pro Pro Val Thr Asn Glu Tyr
        275                 280                 285 tcg ctt agt tgg aag gag cct gat gag gaa gga ata tta aaa ttc ctc    912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa    960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt   1008
Arg Leu Lys Lys Ala Ile Lys Ala Gly Arg Gln Ser Thr Leu Glu Ser
                325                 330                 335 tgg ttc gtt aaa aag aaa ccc taa                                   1032
Trp Phe Val Lys Lys Lys Pro
            340
```

<210> SEQ ID NO 10
<211> LENGTH: 343
<212> TYPE: PRT
<213> ORGANISM: Artificial Sequence
<220> FEATURE:
<223> OTHER INFORMATION: Flap endonuclease mutant(F79A)

<400> SEQUENCE: 10

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Arg Asp Gly Thr Pro Leu Met
```

-continued

```
                35                  40                  45
Asp Ser Gly Gly Arg Ile Thr Ser His Leu Ser Gly Leu Phe Tyr Arg
        50                  55                  60

Thr Ile Asn Leu Met Glu Ala Gly Ile Lys Pro Ala Tyr Val Ala Asp
 65                  70                  75                  80

Gly Lys Pro Pro Glu Phe Lys Arg Lys Glu Leu Glu Lys Arg Arg Glu
                 85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Lys Pro
            340
```

```
<210> SEQ ID NO 11
<211> LENGTH: 1032
<212> TYPE: DNA
<213> ORGANISM: Artificial Sequence
<220> FEATURE:
<223> OTHER INFORMATION: Flap endonuclease mutant(F79H)
<220> FEATURE:
<221> NAME/KEY: CDS
<222> LOCATION: (1)..(1029)

<400> SEQUENCE: 11 atg ggt gtt cct atc ggt gac ctc gtt ccg cgc aag gag atc gac ctt      48
Met Gly Val Pro Ile Gly Asp Leu Val Pro Arg Lys Glu Ile Asp Leu
 1               5                  10                  15 gaa aat ctg tat gga aag aag ata gcg ata gat gcc cta aac gcc atc      96
Glu Asn Leu Tyr Gly Lys Lys Ile Ala Ile Asp Ala Leu Asn Ala Ile
                20                  25                  30
```

```
tat cag ttt tta tca acg ata cga cag cgt gat gga aca cca ctt atg        144
Tyr Gln Phe Leu Ser Thr Ile Arg Gln Arg Asp Gly Thr Pro Leu Met
         35                  40                  45 gac tct ggc ggt agg ata acc tct cat tta agt ggg ctc ttt tat aga        192
Asp Ser Gly Gly Arg Ile Thr Ser His Leu Ser Gly Leu Phe Tyr Arg
 50                  55                  60 acg ata aat cta atg gaa gcc ggt att aag ccg gcc tac gtc cat gat        240
Thr Ile Asn Leu Met Glu Ala Gly Ile Lys Pro Ala Tyr Val His Asp
 65                  70                  75                  80 gga aag cct ccg gaa ttt aaa cgc aag gaa cta gaa aaa cgc cgt gaa        288
Gly Lys Pro Pro Glu Phe Lys Arg Lys Glu Leu Glu Lys Arg Arg Glu
                     85                  90                  95 gct cgt gaa gag gca gaa cta aaa tgg aaa gaa gct cta gcc aag gga        336
Ala Arg Glu Glu Ala Glu Leu Lys Trp Lys Glu Ala Leu Ala Lys Gly
                100                 105                 110 aac ctg gag gaa gct agg aaa tac gct caa agg gca act aag gtt aat        384
Asn Leu Glu Glu Ala Arg Lys Tyr Ala Gln Arg Ala Thr Lys Val Asn
            115                 120                 125 gaa atg cta atc gaa gat gca aag aag ctt ttg caa cta atg gga ata        432
Glu Met Leu Ile Glu Asp Ala Lys Lys Leu Leu Gln Leu Met Gly Ile
130                 135                 140 cca ata att cag gct cca agt gaa gga gaa gcc caa gcg gca tac atg        480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca        528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga        576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag        624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa        672
Leu Val Val Leu Asp Glu Val Leu Lys Glu Leu Lys Ile Thr Arg Glu
210                 215                 220 aag ctt ata gaa ctt gca att ctg gtt ggg act gac tat aat cct ggg        720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat        768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt        816
Ser Arg Asp Pro Leu Ala Lys Phe Gln Arg Gln Ser Asp Val Asp Leu
            260                 265                 270 tac gct att aag gaa ttc ttc ctt aac cct cct gtc act aat gaa tac        864
Tyr Ala Ile Lys Glu Phe Phe Leu Asn Pro Pro Val Thr Asn Glu Tyr
        275                 280                 285 tcg ctt agt tgg aag gag cct gat gag gaa gga ata tta aaa ttc ctc        912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa        960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt       1008
Arg Leu Lys Lys Ala Ile Lys Ala Gly Arg Gln Ser Thr Leu Glu Ser
                325                 330                 335 tgg ttc gtt aaa aag aaa ccc taa                                       1032
Trp Phe Val Lys Lys Lys Pro
```

<210> SEQ ID NO 12
<211> LENGTH: 343
<212> TYPE: PRT
<213> ORGANISM: Artificial Sequence
<220> FEATURE:
<223> OTHER INFORMATION: Flap endonuclease mutant(F79H)

<400> SEQUENCE: 12

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
50                  55                  60

Thr Ile Asn Leu Met Glu Ala Gly Ile Lys Pro Ala Tyr Val His Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Ala Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Lys Pro
            340
```

-continued

```
<210> SEQ ID NO 13
<211> LENGTH: 1032
<212> TYPE: DNA
<213> ORGANISM: Artificial Sequence
<220> FEATURE:
<223> OTHER INFORMATION: Flap endonuclease mutant (Y33AF79A)
<220> FEATURE:
<221> NAME/KEY: CDS
<222> LOCATION: (1)..(1029)

<400> SEQUENCE: 13
```

| | | | | | | | | | | | | | | | | |
|---|---|---|---|---|---|---|---|---|---|---|---|---|---|---|---|---|
| atg | ggt | gtt | cct | atc | ggt | gac | ctc | gtt | ccg | cgc | aag | gag | atc | gac | ctt | 48 |
| Met | Gly | Val | Pro | Ile | Gly | Asp | Leu | Val | Pro | Arg | Lys | Glu | Ile | Asp | Leu | |
| 1 | | | | 5 | | | | | 10 | | | | | 15 | | |
| gaa | aat | ctg | tat | gga | aag | aag | ata | gcg | ata | gat | gcc | cta | aac | gcc | atc | 96 |
| Glu | Asn | Leu | Tyr | Gly | Lys | Lys | Ile | Ala | Ile | Asp | Ala | Leu | Asn | Ala | Ile | |
| | | | 20 | | | | | 25 | | | | | 30 | | | |
| gcg | cag | ttt | tta | tca | acg | ata | cga | cag | cgt | gat | gga | aca | cca | ctt | atg | 144 |
| Ala | Gln | Phe | Leu | Ser | Thr | Ile | Arg | Gln | Arg | Asp | Gly | Thr | Pro | Leu | Met | |
| | | 35 | | | | | 40 | | | | | 45 | | | | |
| gac | tct | ggc | ggt | agg | ata | acc | tct | cat | tta | agt | ggg | ctc | ttt | tat | aga | 192 |
| Asp | Ser | Gly | Gly | Arg | Ile | Thr | Ser | His | Leu | Ser | Gly | Leu | Phe | Tyr | Arg | |
| | 50 | | | | | 55 | | | | | 60 | | | | | |
| acg | ata | aat | cta | atg | gaa | gcc | ggt | att | aag | ccg | gcc | tac | gtc | gcg | gat | 240 |
| Thr | Ile | Asn | Leu | Met | Glu | Ala | Gly | Ile | Lys | Pro | Ala | Tyr | Val | Ala | Asp | |
| 65 | | | | | 70 | | | | | 75 | | | | | 80 | |
| gga | aag | cct | ccg | gaa | ttt | aaa | cgc | aag | gaa | cta | gaa | aaa | cgc | cgt | gaa | 288 |
| Gly | Lys | Pro | Pro | Glu | Phe | Lys | Arg | Lys | Glu | Leu | Glu | Lys | Arg | Arg | Glu | |
| | | | | 85 | | | | | 90 | | | | | 95 | | |
| gct | cgt | gaa | gag | gca | gaa | cta | aaa | tgg | aaa | gaa | gct | cta | gcc | aag | gga | 336 |
| Ala | Arg | Glu | Glu | Ala | Glu | Leu | Lys | Trp | Lys | Glu | Ala | Leu | Ala | Lys | Gly | |
| | | | 100 | | | | | 105 | | | | | 110 | | | |
| aac | ctg | gag | gaa | gct | agg | aaa | tac | gct | caa | agg | gca | act | aag | gtt | aat | 384 |
| Asn | Leu | Glu | Glu | Ala | Arg | Lys | Tyr | Ala | Gln | Arg | Ala | Thr | Lys | Val | Asn | |
| | | 115 | | | | | 120 | | | | | 125 | | | | |
| gaa | atg | cta | atc | gaa | gat | gca | aag | aag | ctt | ttg | caa | cta | atg | gga | ata | 432 |
| Glu | Met | Leu | Ile | Glu | Asp | Ala | Lys | Lys | Leu | Leu | Gln | Leu | Met | Gly | Ile | |
| | 130 | | | | | 135 | | | | | 140 | | | | | |
| cca | ata | att | cag | gct | cca | agt | gaa | gga | gaa | gcc | caa | gcg | gca | tac | atg | 480 |
| Pro | Ile | Ile | Gln | Ala | Pro | Ser | Glu | Gly | Glu | Ala | Gln | Ala | Ala | Tyr | Met | |
| 145 | | | | | 150 | | | | | 155 | | | | | 160 | |
| gca | agt | aaa | ggg | gat | gtc | tac | gcg | tca | gcg | agt | caa | gat | tat | gat | tca | 528 |
| Ala | Ser | Lys | Gly | Asp | Val | Tyr | Ala | Ser | Ala | Ser | Gln | Asp | Tyr | Asp | Ser | |
| | | | | 165 | | | | | 170 | | | | | 175 | | |
| cta | ctc | ttt | ggt | gct | cca | agg | ttg | att | agg | aat | ctg | aca | att | acg | gga | 576 |
| Leu | Leu | Phe | Gly | Ala | Pro | Arg | Leu | Ile | Arg | Asn | Leu | Thr | Ile | Thr | Gly | |
| | | | 180 | | | | | 185 | | | | | 190 | | | |
| aaa | aga | aag | atg | cct | ggg | aaa | gat | gtt | tac | gtt | gaa | ata | aag | cca | gag | 624 |
| Lys | Arg | Lys | Met | Pro | Gly | Lys | Asp | Val | Tyr | Val | Glu | Ile | Lys | Pro | Glu | |
| | | 195 | | | | | 200 | | | | | 205 | | | | |
| tta | gta | gtt | cta | gat | gag | gta | cta | aaa | gag | ctt | aag | ata | aca | aga | gaa | 672 |
| Leu | Val | Val | Leu | Asp | Glu | Val | Leu | Lys | Glu | Leu | Lys | Ile | Thr | Arg | Glu | |
| | 210 | | | | | 215 | | | | | 220 | | | | | |
| aag | ctt | ata | gaa | ctt | gca | att | ctg | gtt | ggg | act | gac | tat | aat | cct | ggg | 720 |
| Lys | Leu | Ile | Glu | Leu | Ala | Ile | Leu | Val | Gly | Thr | Asp | Tyr | Asn | Pro | Gly | |
| 225 | | | | | 230 | | | | | 235 | | | | | 240 | |
| ggc | gta | aag | ggg | ata | gga | cct | aag | aag | gcc | ctt | gag | att | gta | aga | tat | 768 |
| Gly | Val | Lys | Gly | Ile | Gly | Pro | Lys | Lys | Ala | Leu | Glu | Ile | Val | Arg | Tyr | |
| | | | | 245 | | | | | 250 | | | | | 255 | | |
| tca | agg | gat | ccc | cta | gca | aag | ttc | caa | aga | cag | agc | gat | gtg | gat | ctt | 816 |
| Ser | Arg | Asp | Pro | Leu | Ala | Lys | Phe | Gln | Arg | Gln | Ser | Asp | Val | Asp | Leu | |
| | | | 260 | | | | | 265 | | | | | 270 | | | |

```
tac gct att aag gaa ttc ttc ctt aac cct cct gtc act aat gaa tac      864
Tyr Ala Ile Lys Glu Phe Phe Leu Asn Pro Pro Val Thr Asn Glu Tyr
            275                 280                 285 tcg ctt agt tgg aag gag cct gat gag gaa gga ata tta aaa ttc ctc      912
Ser Leu Ser Trp Lys Glu Pro Asp Glu Glu Gly Ile Leu Lys Phe Leu
        290                 295                 300 tgt gat gag cat aat ttt agc gaa gaa agg gta aaa aat ggg ata gaa      960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt     1008
Arg Leu Lys Lys Ala Ile Lys Ala Gly Arg Gln Ser Thr Leu Glu Ser
                325                 330                 335 tgg ttc gtt aaa aag aaa ccc taa                                     1032
Trp Phe Val Lys Lys Lys Pro
            340
```

<210> SEQ ID NO 14
<211> LENGTH: 343
<212> TYPE: PRT
<213> ORGANISM: Artificial Sequence
<220> FEATURE:
<223> OTHER INFORMATION: Flap endonuclease mutant (Y33AF79A)

<400> SEQUENCE: 14

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Ala Gln Phe Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Ala Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255
```

```
Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
            290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Pro
            340

<210> SEQ ID NO 15
<211> LENGTH: 1032
<212> TYPE: DNA
<213> ORGANISM: Artificial Sequence
<220> FEATURE:
<223> OTHER INFORMATION: Flap endonuclease mutant(F278AF279A)
<220> FEATURE:
<221> NAME/KEY: CDS
<222> LOCATION: (1)..(1029)

<400> SEQUENCE: 15 atg ggt gtt cct atc ggt gac ctc gtt ccg cgc aag gag atc gac ctt      48
Met Gly Val Pro Ile Gly Asp Leu Val Pro Arg Lys Glu Ile Asp Leu
1               5                   10                  15 gaa aat ctg tat gga aag aag ata gcg ata gat gcc cta aac gcc atc      96
Glu Asn Leu Tyr Gly Lys Lys Ile Ala Ile Asp Ala Leu Asn Ala Ile
            20                  25                  30 tat cag ttt tta tca acg ata cga cag cgt gat gga aca cca ctt atg     144
Tyr Gln Phe Leu Ser Thr Ile Arg Gln Arg Asp Gly Thr Pro Leu Met
        35                  40                  45 gac tct ggc ggt agg ata acc tct cat tta agt ggg ctc ttt tat aga     192
Asp Ser Gly Gly Arg Ile Thr Ser His Leu Ser Gly Leu Phe Tyr Arg
    50                  55                  60 acg ata aat cta atg gaa gcc ggt att aag ccg gcc tac gtc ttt gat     240
Thr Ile Asn Leu Met Glu Ala Gly Ile Lys Pro Ala Tyr Val Phe Asp
65                  70                  75                  80 gga aag cct ccg gaa ttt aaa cgc aag gaa cta gaa aaa cgc cgt gaa     288
Gly Lys Pro Pro Glu Phe Lys Arg Lys Glu Leu Glu Lys Arg Arg Glu
                85                  90                  95 gct cgt gaa gag gca gaa cta aaa tgg aaa gaa gct cta gcc aag gga     336
Ala Arg Glu Glu Ala Glu Leu Lys Trp Lys Glu Ala Leu Ala Lys Gly
            100                 105                 110 aac ctg gag gaa gct agg aaa tac gct caa agg gca act aag gtt aat     384
Asn Leu Glu Glu Ala Arg Lys Tyr Ala Gln Arg Ala Thr Lys Val Asn
        115                 120                 125 gaa atg cta atc gaa gat gca aag aag ctt ttg caa cta atg gga ata     432
Glu Met Leu Ile Glu Asp Ala Lys Lys Leu Leu Gln Leu Met Gly Ile
    130                 135                 140 cca ata att cag gct cca agt gaa gga gaa gcc caa gcg gca tac atg     480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca     528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga     576
Leu Leu Phe Gly Ala Pro Arg Leu Ile Arg Asn Leu Thr Ile Thr Gly
            180                 185                 190
```

```
aaa aga aag atg cct ggg aaa gat gtt tac gtt gaa ata aag cca gag      624
Lys Arg Lys Met Pro Gly Lys Asp Val Tyr Val Glu Ile Lys Pro Glu
            195                 200                 205 tta gta gtt cta gat gag gta cta aaa gag ctt aag ata aca aga gaa      672
Leu Val Val Leu Asp Glu Val Leu Lys Glu Leu Lys Ile Thr Arg Glu
210                 215                 220 aag ctt ata gaa ctt gca att ctg gtt ggg act gac tat aat cct ggg      720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat      768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt      816
Ser Arg Asp Pro Leu Ala Lys Phe Gln Arg Gln Ser Asp Val Asp Leu
            260                 265                 270 tac gct att aag gaa gcg gcg ctt aac cct cct gtc act aat gaa tac      864
Tyr Ala Ile Lys Glu Ala Ala Leu Asn Pro Pro Val Thr Asn Glu Tyr
        275                 280                 285 tcg ctt agt tgg aag gag cct gat gag gaa gga ata tta aaa ttc ctc      912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa      960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt     1008
Arg Leu Lys Lys Ala Ile Lys Ala Gly Arg Gln Ser Thr Leu Glu Ser
                325                 330                 335 tgg ttc gtt aaa aag aaa ccc taa                                     1032
Trp Phe Val Lys Lys Lys Pro
            340

<210> SEQ ID NO 16
<211> LENGTH: 343
<212> TYPE: PRT
<213> ORGANISM: Artificial Sequence
<220> FEATURE:
<223> OTHER INFORMATION: Flap endonuclease mutant(F278AF279A)

<400> SEQUENCE: 16

Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Lys Arg Arg Glu
            85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160
```

```
Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Ala Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Pro
            340

<210> SEQ ID NO 17
<211> LENGTH: 42
<212> TYPE: DNA
<213> ORGANISM: Artificial Sequence
<220> FEATURE:
<223> OTHER INFORMATION: Primer(FEN-U)

<400> SEQUENCE: 17
gggaattcct gcagatcgca tatgggtgtt cctatcggtg ac                    42

<210> SEQ ID NO 18
<211> LENGTH: 50
<212> TYPE: DNA
<213> ORGANISM: Artificial Sequence
<220> FEATURE:
<223> OTHER INFORMATION: Primer(FEN-R)

<400> SEQUENCE: 18
acgcgtcgac gtccgctcga gcggttaggg tttcttttta acgaaccaac            50

<210> SEQ ID NO 19
<211> LENGTH: 48
<212> TYPE: DNA
<213> ORGANISM: Artificial Sequence
<220> FEATURE:
<223> OTHER INFORMATION: Primer(Y33A-U)

<400> SEQUENCE: 19
atagatgccc taaacgccat cgcgcagttt ttatcaacga tacgacag              48

<210> SEQ ID NO 20
<211> LENGTH: 48
<212> TYPE: DNA
<213> ORGANISM: Artificial Sequence
<220> FEATURE:
```

-continued

<223> OTHER INFORMATION: Primer(Y33A-R)

<400> SEQUENCE: 20
ctgtcgtatc gttgataaaa actgcgcgat ggcgtttagg gcatctat        48

<210> SEQ ID NO 21
<211> LENGTH: 48
<212> TYPE: DNA
<213> ORGANISM: Artificial Sequence
<220> FEATURE:
<223> OTHER INFORMATION: Primer(Y33L-U)

<400> SEQUENCE: 21
atagatgccc taaacgccat cctgcagttt ttatcaacga tacgacag        48

<210> SEQ ID NO 22
<211> LENGTH: 48
<212> TYPE: DNA
<213> ORGANISM: Artificial Sequence
<220> FEATURE:
<223> OTHER INFORMATION: Primer(Y33L-R)

<400> SEQUENCE: 22
ctgtcgtatc gttgataaaa actgcaggat ggcgtttagg gcatctat        48

<210> SEQ ID NO 23
<211> LENGTH: 48
<212> TYPE: DNA
<213> ORGANISM: Artificial Sequence
<220> FEATURE:
<223> OTHER INFORMATION: Primer(F35Y-U)

<400> SEQUENCE: 23
gccctaaacg ccatctatca gtatttatca acgatacgac agcgtgat        48

<210> SEQ ID NO 24
<211> LENGTH: 48
<212> TYPE: DNA
<213> ORGANISM: Artificial Sequence
<220> FEATURE:
<223> OTHER INFORMATION: Primer(F35Y-R)

<400> SEQUENCE: 24
atcacgctgt cgtatcgttg ataaatactg atagatggcg tttagggc        48

<210> SEQ ID NO 25
<211> LENGTH: 48
<212> TYPE: DNA
<213> ORGANISM: Artificial Sequence
<220> FEATURE:
<223> OTHER INFORMATION: Primer(F79A-U)

<400> SEQUENCE: 25
ggtattaagc cggcctacgt cgcggatgga aagcctccgg aatttaaa        48

<210> SEQ ID NO 26
<211> LENGTH: 48
<212> TYPE: DNA
<213> ORGANISM: Artificial Sequence
<220> FEATURE:
<223> OTHER INFORMATION: Primer(F79A-R)

<400> SEQUENCE: 26
tttaaattcc ggaggctttc catccgcgac gtaggccggc ttaatacc        48

<210> SEQ ID NO 27
<211> LENGTH: 48
<212> TYPE: DNA
<213> ORGANISM: Artificial Sequence
<220> FEATURE:
<223> OTHER INFORMATION: Primer(F79H-U)

<400> SEQUENCE: 27
ggtattaagc cggcctacgt ccatgatgga aagcctccgg aatttaaa         48

<210> SEQ ID NO 28
<211> LENGTH: 48
<212> TYPE: DNA
<213> ORGANISM: Artificial Sequence
<220> FEATURE:
<223> OTHER INFORMATION: Primer(F79H-R)

<400> SEQUENCE: 28
tttaaattcc ggaggctttc catcatggac gtaggccggc ttaatacc         48

<210> SEQ ID NO 29
<211> LENGTH: 49
<212> TYPE: DNA
<213> ORGANISM: Artificial Sequence
<220> FEATURE:
<223> OTHER INFORMATION: Primer(F278A279A-U)

<400> SEQUENCE: 29
ctttacgcta ttaaggaagc ggcgccttaa ccctcctgtc actaatgaa         49

<210> SEQ ID NO 30
<211> LENGTH: 48
<212> TYPE: DNA
<213> ORGANISM: Artificial Sequence
<220> FEATURE:
<223> OTHER INFORMATION: Primer(F278A279A-R)

<400> SEQUENCE: 30
ttcattagtg acaggagggt taagcgccgc ttccttaata gcgtaaag         48

<210> SEQ ID NO 31
<211> LENGTH: 54
<212> TYPE: DNA
<213> ORGANISM: Artificial Sequence
<220> FEATURE:
<223> OTHER INFORMATION: DNA(template strand A) for preparation of
      substrates

<400> SEQUENCE: 31
gagctagatg tcggactctg cctcaagacg gtagtcaacg tgcactcgag gtca      54

<210> SEQ ID NO 32
<211> LENGTH: 26
<212> TYPE: DNA
<213> ORGANISM: Artificial Sequence
<220> FEATURE:
<223> OTHER INFORMATION: DNA(upstream strandB-1)for preparation of
      substrates

<400> SEQUENCE: 32
tgacctcgag tgcacgttga ctaccg         26

<210> SEQ ID NO 33
<211> LENGTH: 27
<212> TYPE: DNA
<213> ORGANISM: Artificial Sequence
<220> FEATURE:

```
<223> OTHER INFORMATION: DNA(upstream strandB-2) for preparation of
      substrates

<400> SEQUENCE: 33
tgacctcgag tgcacgttga ctaccgc                                        27

<210> SEQ ID NO 34
<211> LENGTH: 26
<212> TYPE: DNA
<213> ORGANISM: Artificial Sequence
<220> FEATURE:
<223> OTHER INFORMATION: DNA(upstream strand B-3) for preparation of
      substrate

<400> SEQUENCE: 34
tgacctcgag tgcacgttga ctacca                                         26

<210> SEQ ID NO 35
<211> LENGTH: 28
<212> TYPE: DNA
<213> ORGANISM: Artificial Sequence
<220> FEATURE:
<223> OTHER INFORMATION: DNA(downstream strand C-1) for preparation of
      substrates

<400> SEQUENCE: 35
tcttgaggca gagtccgaca tctagctc                                       28

<210> SEQ ID NO 36
<211> LENGTH: 32
<212> TYPE: DNA
<213> ORGANISM: Artificial Sequence
<220> FEATURE:
<223> OTHER INFORMATION: DNA(flap strandC-2) for preparation of
      substrates

<400> SEQUENCE: 36
taactcttga ggcagagtcc gacatctagc tc                                  32

<210> SEQ ID NO 37
<211> LENGTH: 57
<212> TYPE: DNA
<213> ORGANISM: Artificial Sequence
<220> FEATURE:
<223> OTHER INFORMATION: DNA(flap strand C-3) for preparation of
      substrates

<400> SEQUENCE: 37
gcatctgacg gatgtcaagc agtcctaact cttgaggcag agtccgacat ctagctc       57

<210> SEQ ID NO 38
<211> LENGTH: 29
<212> TYPE: DNA
<213> ORGANISM: Artificial Sequence
<220> FEATURE:
<223> OTHER INFORMATION: DNA(downstream strand C-4) for preparation of
      substrate

<400> SEQUENCE: 38
ctcttgaggc agagtccgac atctagctc                                      29

<210> SEQ ID NO 39
<211> LENGTH: 51
<212> TYPE: DNA
<213> ORGANISM: Artificial Sequence
<220> FEATURE:
<223> OTHER INFORMATION: Primer(Y33AF35A-U)
```

-continued

<400> SEQUENCE: 39
atagatgccc taaacgccat cgcgcaggcg ttatcaacga taagacagag g          51

<210> SEQ ID NO 40
<211> LENGTH: 51
<212> TYPE: DNA
<213> ORGANISM: Artificial Sequence
<220> FEATURE:
<223> OTHER INFORMATION: Primer(Y33AF35A-R)

<400> SEQUENCE: 40
cctctgtctt atcgttgata acgcctgcgc gatggcgttt agggcatcta t          51

<210> SEQ ID NO 41
<211> LENGTH: 20
<212> TYPE: DNA
<213> ORGANISM: Artificial Sequence
<220> FEATURE:
<223> OTHER INFORMATION: DNA(Downstream C-1-1) for preparetion of
      substrate

<400> SEQUENCE: 41
tcttgaggca gagtccgaca                                             20

<210> SEQ ID NO 42
<211> LENGTH: 20
<212> TYPE: DNA
<213> ORGANISM: Artificial Sequence
<220> FEATURE:
<223> OTHER INFORMATION: DNA(Flap strand(C-4-1) for preparation
      substrate

<400> SEQUENCE: 42
ctcttgaggc agagtccgac                                             20

<210> SEQ ID NO 43
<211> LENGTH: 54
<212> TYPE: DNA
<213> ORGANISM: Artificial Sequence
<220> FEATURE:
<223> OTHER INFORMATION: DNA(Template StrandG) for preparation of
      substrates

<400> SEQUENCE: 43
gagctagatg tcggactctg cctcaaggcg gtagtcaacg tgcactcgag gtca       54

<210> SEQ ID NO 44
<211> LENGTH: 54
<212> TYPE: DNA
<213> ORGANISM: Artificial Sequence
<220> FEATURE:
<223> OTHER INFORMATION: DNA(Temprate Strand C) for preparation
      substrate

<400> SEQUENCE: 44
gagctagatg tcggactctg cctcaagccg gtagtcaacg tgcactcgag gtca       54

<210> SEQ ID NO 45
<211> LENGTH: 54
<212> TYPE: DNA
<213> ORGANISM: Artificial Sequence
<220> FEATURE:
<223> OTHER INFORMATION: DNA(Template Strand T) for preparation of
      substrates

<400> SEQUENCE: 45

-continued

```
gagctagatg tcggactctg cctcaagtcg gtagtcaacg tgcactcgag gtca      54
```

<210> SEQ ID NO 46
<211> LENGTH: 28
<212> TYPE: DNA
<213> ORGANISM: Artificial Sequence
<220> FEATURE:
<223> OTHER INFORMATION: ProbeA(C)

<400> SEQUENCE: 46

```
ccttgaggca gagtccgaca tctagctc                                   28
```

<210> SEQ ID NO 47
<211> LENGTH: 28
<212> TYPE: DNA
<213> ORGANISM: Artificial Sequence
<220> FEATURE:
<223> OTHER INFORMATION: ProbeA(G)

<400> SEQUENCE: 47

```
gcttgaggca gagtccgaca tctagctc                                   28
```

<210> SEQ ID NO 48
<211> LENGTH: 28
<212> TYPE: DNA
<213> ORGANISM: Artificial Sequence
<220> FEATURE:
<223> OTHER INFORMATION: ProbeA(A)

<400> SEQUENCE: 48

```
acttgaggca gagtccgaca tctagctc                                   28
```

<210> SEQ ID NO 49
<211> LENGTH: 20
<212> TYPE: DNA
<213> ORGANISM: Artificial Sequence
<220> FEATURE:
<223> OTHER INFORMATION: ProbeA(T)

<400> SEQUENCE: 49

```
tcttgaggca gagtccgaca                                            20
```

<210> SEQ ID NO 50
<211> LENGTH: 20
<212> TYPE: DNA
<213> ORGANISM: Artificial Sequence
<220> FEATURE:
<223> OTHER INFORMATION: ProbeA(C)

<400> SEQUENCE: 50

```
ccttgaggca gagtccgaca                                            20
```

<210> SEQ ID NO 51
<211> LENGTH: 43
<212> TYPE: DNA
<213> ORGANISM: Artificial Sequence
<220> FEATURE:
<223> OTHER INFORMATION: DNA(Flap StrandC-5) for preparation of
      substrates

<400> SEQUENCE: 51

```
cccaaaaaaa aaaaatcttg aggcagagtc cgacatctag ctc                  43
```

<210> SEQ ID NO 52
<211> LENGTH: 43

```
<212> TYPE: DNA
<213> ORGANISM: Artificial Sequence
<220> FEATURE:
<223> OTHER INFORMATION: DNA(Flap StrandC-6) for preparation of
      substrates

<400> SEQUENCE: 52
aaaaaaaaaa aaaaatcttg aggcagagtc cgacatctag ctc                        43

<210> SEQ ID NO 53
<211> LENGTH: 1032
<212> TYPE: DNA
<213> ORGANISM: Artificial Sequence
<220> FEATURE:
<223> OTHER INFORMATION: Flap endonuclease mutant(Y33AF35A)
<220> FEATURE:
<221> NAME/KEY: CDS
<222> LOCATION: (1)..(1029)

<400> SEQUENCE: 53 atg ggt gtt cct atc ggt gac ctc gtt ccg cgc aag gag atc gac ctt       48
Met Gly Val Pro Ile Gly Asp Leu Val Pro Arg Lys Glu Ile Asp Leu
1               5                   10                  15 gaa aat ctg tat gga aag aag ata gcg ata gat gcc cta aac gcc atc       96
Glu Asn Leu Tyr Gly Lys Lys Ile Ala Ile Asp Ala Leu Asn Ala Ile
                20                  25                  30 gcg cag gcg tta tca acg ata cga cag cgt gat gga aca cca ctt atg      144
Ala Gln Ala Leu Ser Thr Ile Arg Gln Arg Asp Gly Thr Pro Leu Met
            35                  40                  45 gac tct ggc ggt agg ata acc tct cat tta agt ggg ctc ttt tat aga      192
Asp Ser Gly Gly Arg Ile Thr Ser His Leu Ser Gly Leu Phe Tyr Arg
        50                  55                  60 acg ata aat cta atg gaa gcc ggt att aag ccg gcc tac gtc ttt gat      240
Thr Ile Asn Leu Met Glu Ala Gly Ile Lys Pro Ala Tyr Val Phe Asp
65                  70                  75                  80 gga aag cct ccg gaa ttt aaa cgc aag gaa cta gaa aaa cgc cgt gaa      288
Gly Lys Pro Pro Glu Phe Lys Arg Lys Glu Leu Glu Lys Arg Arg Glu
                85                  90                  95 gct cgt gaa gag gca gaa cta aaa tgg aaa gaa gct cta gcc aag gga      336
Ala Arg Glu Glu Ala Glu Leu Lys Trp Lys Glu Ala Leu Ala Lys Gly
            100                 105                 110 aac ctg gag gaa gct agg aaa tac gct caa agg gca act aag gtt aat      384
Asn Leu Glu Glu Ala Arg Lys Tyr Ala Gln Arg Ala Thr Lys Val Asn
        115                 120                 125 gaa atg cta atc gaa gat gca aag aag ctt ttg caa cta atg gga ata      432
Glu Met Leu Ile Glu Asp Ala Lys Lys Leu Leu Gln Leu Met Gly Ile
    130                 135                 140 cca ata att cag gct cca agt gaa gga gaa gcc caa gcg gca tac atg      480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca      528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga      576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag      624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa      672
Leu Val Val Leu Asp Glu Val Leu Lys Glu Leu Lys Ile Thr Arg Glu
    210                 215                 220
```

```
aag ctt ata gaa ctt gca att ctg gtt ggg act gac tat aat cct ggg    720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat    768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt    816
Ser Arg Asp Pro Leu Ala Lys Phe Gln Arg Gln Ser Asp Val Asp Leu
            260                 265                 270 tac gct att aag gaa ttc ttc ctt aac cct cct gtc act aat gaa tac    864
Tyr Ala Ile Lys Glu Phe Phe Leu Asn Pro Pro Val Thr Asn Glu Tyr
        275                 280                 285 tcg ctt agt tgg aag gag cct gat gag gaa gga ata tta aaa ttc ctc    912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa    960
Cys Asp Glu His Asn Phe Ser Glu Glu Arg Val Lys Asn Gly Ile Glu
305                 310                 315                 320 aga cta aaa aag gcg ata aaa gct gga aga caa tca acg ctt gag agt    1008
Arg Leu Lys Lys Ala Ile Lys Ala Gly Arg Gln Ser Thr Leu Glu Ser
                325                 330                 335 tgg ttc gtt aaa aag aaa ccc taa                                     1032
Trp Phe Val Lys Lys Lys Pro
                340

<210> SEQ ID NO 54
<211> LENGTH: 343
<212> TYPE: PRT
<213> ORGANISM: Artificial Sequence
<220> FEATURE:
<223> OTHER INFORMATION: Flap endonuclease mutant(Y33AF35A)

<400> SEQUENCE: 54

Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Ala Gln Ala Leu Ser Thr Ile Arg Gln Arg Asp Gly Thr Pro Leu Met
        35                  40                  45

Asp Ser Gly Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
```

-continued

```
            195                 200                 205
Leu Val Val Leu Asp Glu Val Leu Lys Glu Leu Lys Ile Thr Arg Glu
        210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
                260                 265                 270

Tyr Ala Ile Lys Glu Phe Phe Leu Asn Pro Pro Val Thr Asn Glu Tyr
            275                 280                 285

Ser Leu Ser Trp Lys Glu Pro Asp Glu Glu Gly Ile Leu Lys Phe Leu
        290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser
                325                 330                 335

Trp Phe Val Lys Lys Lys Pro
                340
```

FLAP ENDONUCLEASE MUTANTS

BACKGROUND OF THE INVENTION

1. Field of the Invention

The present invention relates to a novel flap endonuclease mutant derived from a wild type flap endonuclease by modifying its substrate specificity, and a reagent for the analysis of genetic polymorphism using the same.

2. Background Art

A flap endonuclease is an essential enzyme for DNA replication/repair, because it recognizes DNA structure in a specific manner to cleave flap strands. In addition, this enzyme has 5' exonuclease activity. The enzyme has been characterized for its crystal structure, and its mutant has been used to investigate the substrate recognizing mechanisms. In addition, a *Pyrococcus* derived thermostable enzyme is known as a thermostable flap endonuclease.

Meanwhile, substrate specificity of these flap endonucleases has been utilized in recent years for analyzing genetic polymorphism.

By genetic polymorphism is meant a phenomenon that nucleotide sequences in the same position of a certain gene differ between different individuals, and it is distinguished from mutation by the frequency with which they occur. However, since genetic polymorphism may cause diseases directly, and single nucleotide polymorphism (SNP), the currently most frequent polymorphism, is thought to complicate lifestyle-related diseases and is considered a genetic predisposition, enormous data has been accumulated regarding the location and nucleotides of SNPs.

Known methods of SNP analysis using the flap endonuclease as stated above include an invader method. The method involves determining the presence/absence of a SNP by examining whether a flap endonuclease recognizes the three-nucleotide overlapping structure formed as a result of annealing of the target nucleic acid (SNP area on the genome) and invader and signal probes and cleaves the flap portion. However, flap endonucleases known to date have substrate specificity that is so broad that they detect genetic defects other than SNPs, such as nicks, and are insufficient in reliability.

[Non-patent Document 1] Kaiser, M., Lyamicheva, N., Ma, W., Miller, C., Neri, B., Fors, L., and Lyamichev, V., (1999) J. Biol. Chem., 274, 21387-21394

[Non-patent Document 2] Lyamichev, V., Brow, M. A. D., Varvel, V. E., and Dahlberg, J. E., (1999) Proc. Natl. Acad. Sci., 96, 6143-6148

SUMMARY OF THE INVENTION

It is an object of the present invention to modify the substrate specificity of flap endonuclease to provide analytical means that is more accurate and sensitive than conventional methods in detecting genetic polymorphism.

To solve the problems described above, the inventors have succeeded in the introduction of a mutation into the substrate-binding site of a flap endonuclease to prepare a mutant with modified substrate specificity.

Wild type flap endonuclease has a broad substrate specificity and acts on substrates where one strand of the double-stranded DNA has been cleaved, resulting in a 3' projection structure, substrates devoid of such 3' projection structure, and substrates with nicks, while the mutant described above acts on substrates where one strand of the double-stranded DNA has been cleaved resulting in a 3' projection structure and where the complementary portion of the cleaved DNA strand is linked to form base pairs devoid of deletion sites in relation to the other DNA strand. In other words, the mutant of the present invention acts on substrates having 3' projection structure and it hardly cleaves substrates which do not have such 3' projection structure; moreover, it acts only on DNA strands having 3' projection structure that have specific structure.

Using such substrate specificity of the mutant enzyme in the analysis of genetic polymorphism, a novel fluorescence method can be provided that detects accurately only polymorphism.

Thus, the present invention comprises (1) to (6) below.

(1) A flap endonuclease mutant wherein an amino acid in the amino acid sequence of the wild type flap endonuclease is substituted by other amino acid, wherein the mutant acts, among substrates for the wild type flap endonuclease, on the DNA substrates where one strand of the double-stranded DNA has been cleaved, resulting in a 3' projection structure, and where each of the cleaved DNA strand has a nucleotide sequence portion that is complementary to the other DNA strand, and the complementary nucleotide sequence portions are linked to form base pairs devoid of deletion sites in relation to the other DNA strand, and wherein the mutant does not act or has reduced activity on other substrates.

(2) A mutant of the flap endonuclease depicted in the amino acid sequence of SEQ ID No. 2 of the Sequence Listing, having a mutation selected from (A) the amino acid at position 33 is alanine or leucine, (B) the amino acid at position 35 is tyrosine, (C) the amino acid at position 79 is alanine or histidine, (D) the amino acids at positions 33 and 79 are both alanine, (E) the amino acids at positions 33 and 35 are both alanine, and (F) the amino acids at positions 278 and 279 are both alanine.

(3) DNA encoding the mutant of flap endonuclease as described in (2) above.

(4) A recombinant vector comprising the DNA encoding the mutant of flap endonuclease as described in (3) above.

(5) A transformant transformed by the recombinant vector as described in (4) above.

(6) A reagent for the analysis of genetic polymorphism consisting of the flap endonuclease mutant as described in (1) or (2) above.

BRIEF DESCRIPTION OF THE DRAWINGS

FIG. 14 is a schematic view showing the structure of the substrates prepared in Example 9;

DETAILED DESCRIPTION OF THE PREFERRED EMBODIMENTS

Figure 1:
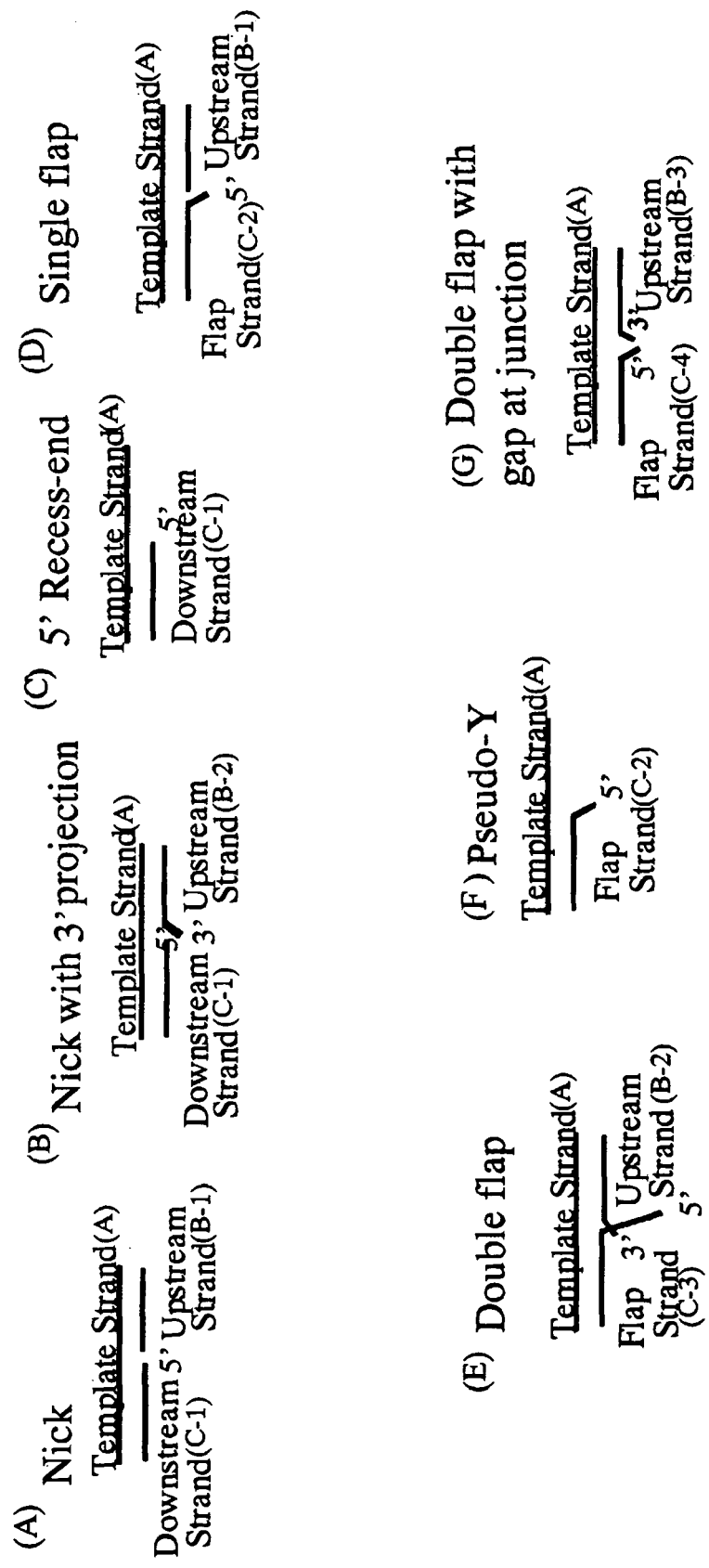
FIG. 1 is a schematic view showing the structure of substrates for flap endonuclease.

The flap endonuclease mutant of the present invention has been derived from a wild type flap endonuclease by modifying its substrate specificity. The wild type flap endonuclease acts on DNA substrates having nicks, nicks with 3' projection, 5' recess-ends, single flaps, double flaps, and pseudo-Y structure. Also, the wild type flap endonuclease acts on a DNA substrate having a double flap with a gap at a junction (hereafter referred to as a "double flap with a gap"). The structures of such DNA substrates are shown in FIG. 1.

Among these substrates, a double flap substrate with a gap at a junction has the 3' projection structure formed by cleavage on one strand of the double-stranded DNA, and each cleaved DNA strand has a nucleotide sequence complementary to the other DNA strand of the double-stranded DNA; however, even if the complementary nucleotide sequences are combined, some nucleotides corresponding to the other DNA strand are lacking, resulting in the absence of continuous base pairs with the other DNA strand.

Thus, the wild type flap endonuclease has a broad substrate specificity, and acts on the seven DNA substrates of different structures. In addition, the flap endonuclease has both endonuclease and exonuclease actions, and the wild type flap endonuclease eliminates, by its exonuclease action, the downstream strand at the 5' end of the substrate with a nick, nick with 3' projection or 5' recess-end among the seven DNA substrates described above. In addition, by its endonuclease action, the wild type flap endonuclease cleaves the 5' end flap of the flap strand of the substrate with a single flap, double flap, pseudo-Y structure, and double flap with a gap at a junction, and further eliminates a region closer to the 5' end of the cleavage site by its exonuclease action.

In contrast, the flap endonuclease mutant of the present invention acts only on the substrate with a nick with 3' projection or a double flap among the substrates for the wild type endonuclease described above.

In other words, for the substrates with nicks with 3' projection, the 5' end-side nucleotide of the downstream strand (C-1) extends to immediately before the nucleotide at the foot of the flap of the upstream strand (B-2), and the strands complementary to the template strands of the downstream strand (C-1) and the upstream strand (B-2) are linked to form base pairs devoid of deletions in relation to the other DNA strand (template strand (A)). Similarly, for substrates with double flaps, the complementary sequences of the flap strand (C-3) and upstream strand (B-2) for the other DNA strand (template strand (A)) are linked to form base pairs devoid of deletion sites in relation to the other DNA strand (template strand (A)).

However, the endonuclease mutant of the present invention does not act on the five types of DNA substrates other than these, or its activity on them is extremely weak.

The flap endonuclease mutant of the present invention has a mode of action similar to that of the wild type flap endonuclease, and eliminates the 5' end side of the downstream strand of the substrate with a nick with 3' projection and cleaves the flap portion of the flap strand of the substrate with a double flap. It further eliminates the 5' end side of the cleavage site by its exonuclease action.

The flap endonuclease mutant of the present invention has been derived from a wild type flap endonuclease by mutating the amino acid at the substrate-binding site. To obtain this mutant enzyme, a mutant gene is prepared by site-directed mutagenesis with PCR amplification using the gene encoding the amino acid sequence of the wild type flap endonuclease-1 shown in SEQ ID No. 2, or a plasmid containing this gene, as a template and using primers which have mutation, the mutant gene is linked to a suitable expression vector, this recombinant expression vector is introduced into a host microorganism to form a transformant, and this transformant can be incubated to obtain the subject flap endonuclease mutant from the culture.

In one embodiment of the present invention, this procedure was used to obtain a mutant gene of the gene encoding the wild type flap endonuclease-1 (SEQ ID No. 1 of the Sequence Listing) from *Pyrococcus horikoshii* (accession number JCM9974) and various mutant enzymes obtained with the mutant gene were examined for their enzymatic activity on each of the substrates. As a result, a thermostable flap endonuclease mutant was found which substantially acts only on DNA substrates having 3' projection ends of specific structure. This is exemplified as follows.

A mutant of the amino acid sequence (SEQ ID No. 2 of the Sequence Listing) of the wild type flap endonuclease-1 derived from *Pyrococcus horikoshii*, wherein (E) the amino acids tyrosine at position 33 and phenylalanine at position 35 are both substituted by alanine (hereinafter, sometimes referred to as Y33AF35A), the amino acid sequence of the mutant enzyme is shown in SEQ ID No. 54 of the Sequence Listing; or (F) the amino acids phenylalanine at position 278 and phenylalanine at position 279 are both substituted by alanine (hereinafter, sometimes referred to as F278AF279A), the amino acid sequence of the mutant enzyme is shown in SEQ ID No. 16 of the Sequence Listing.

Each of genes encoding Y33A, Y33L, F35Y, F79A, F79H, Y33AF79A, Y33AF35A, and F278AF279A as described above is not particularly limited as long as they can encode these mutant peptides, and examples of the nucleotide sequences of these genes include those shown in this order in SEQ ID Nos. 3, 5, 7, 9, 11, 13, 53 and 15 of the Sequence Listing.

The following Table 1 shows alignment of amino acid sequences of the flap endonuclease-1 (wild type) family.

TABLE 1

```
                    27      33 35
       phFEN-1   24  LAIDALNAIYQFLSTIRQRDGTPLMDS  50  (amino acid sequence 24 to 50 of SEQ ID No. 1)
       mjFEN-1   24  VAIDGMNALYQFLTSIRLRDGSPLRNR  50  SEQ ID No. 57
        spRAD2   31  VAIDASMSLYQFLIQVRSDQGQQLMNE  57  SEQ ID No. 58
        hFEN-1   31  VAIDASMSIYQFLIAVR-QGGDVLQNE  56  SEQ ID No. 59
        T5 Exo.  23  MIVDGTNLGFRFKHNNSKKPFASSYVS  49  SEQ ID No. 60
        T7 Exo.  22  LVMDGDWLVFQAMSAAEFDASWEEEIW  48  SEQ ID No. 61
   E.coli Pol. 1 10  ILVDGSSYLYRAYHAFPPLTNSAGEPT  37  SEQ ID No. 62
     Taq. Pol. 1 15  LLVDGHHLAYRTFHALKGLTTSRGEPV  42  SEQ IS No. 63

79 80
       phFEN-1   72  GIKFAYVF-DGEPPEFKRKELEK   93  (amino acid sequence 72 to 93 of SEQ ID No. 1)
       mjFEN-1   72  DIIEIWVF-DGEPPKLKEKTRKV   93  SEQ ID No. 64
        spRAD2   79  GIKFCFVF-DGKPPTLKSGELAK  100  SEQ ID No. 65
        hFEN-1   78  GIKPVYVF-DGKPPTLKSGELAK   99  SEQ ID No. 66
        T5 Exo.  60  ARTTIVLG-DKGKSVFR-LEHLP   80  SEQ ID No. 67
        T7 Exo.  77  GAPIVLAFTDSVN--WR-KELVD   96  SEQ ID No. 68
   E.coli Pol. 1 55  PTHAAVVF-DAKGKTFR-DELFE   75  SEQ ID No. 69
     Taq. Pol. 1 59  GDAVIVVF-DAKAPSFR-HEAYG   79  SEQ IS No. 70

279
                  278|
phFEN-1  274  IKEFFFLNPPMTNEYS  289  (amino acid sequence 274 to 289 of SEQ ID No. 1)
mjFEN-1  260  EIKRIFKEPKMTDNYS  275  SEQ ID No. 71
 spRAD2  279  DARRLFLDAEMLPGEE  294  SEQ ID No. 72
 hFEN-1  278  EAHQLFLEPEMLDPES  293  SEQ ID No. 73
```

(A) the amino acid tyrosine at position 33 is substituted by alanine or leucine (hereinafter, sometimes referred to as Y33A and Y33L, respectively), the amino acid sequences of these mutant enzymes are shown in SEQ ID Nos. 4 and 6, respectively, of the Sequence Listing;

(B) the amino acid phenylalanine at position 35 is substituted by tyrosine (hereinafter, sometimes referred to as F35Y), the amino acid sequence of the mutant enzyme is shown in SEQ ID No. 8 of the Sequence Listing;

(C) the amino acid phenylalanine at position 79 is substituted by alanine or hystidine (hereinafter, sometimes referred to as F79A and F79H, respectively), the amino acid sequences of these mutant enzymes are shown in SEQ ID Nos. 10 and 12, respectively, of the Sequence Listing;

(D) the amino acids tyrosine at position 33 and phenylalanine at position 79 are both substituted by alanine (hereinafter, sometimes referred to as Y33AF79A), the amino acid sequence of the mutant enzyme is shown in SEQ ID No. 14 of the Sequence Listing;

Symbols in the table represent as follows:
phFEN-1; flap endonuclease-1 (FEN-1) from *Pyrococcus horikoshii*
mjFEN-1; FEN-1 from *Methanococcus jannaschii*
spRAD2; RAD2 from *Schizosaccharomyces pomb*
hFEN-1; FEN-1 from a human being
T5 EXO; T5 exonuclease
T7 EXO; T7gene6 exonuclease
*E. coli* pol. 1; 5' exonuclease domain in *E. coli* polymerase 1
Taq.pol. 1; 5' exonuclease domain in *Thermus aguaticus* polymerase 1

According to the table, the amino acid at the site targeted for mutation in the substrate-binding domain of the flap endonuclease-1 from *Pyrococcus horikoshii* is almost common among the family, and in particular, is completely common among the flap endonuclease-1 (FEN-1) including that from the human being.

This strongly suggests that similar changes in substrate specificity can be achieved by applying the same mutations used to change the wild type flap endonuclease-1 from *Pyrococcus horikoshii* described above to the wild type flap endonuclease-1 from other source organisms.

The substrate specificity of the flap endonuclease mutant of the present invention for substantially acting on only DNA substrates having 3' projection provides a simple, accurate and novel method for analyzing genetic polymorphism.

A method for genetic polymorphism analysis using the flap endonuclease mutant of the present invention as a reagent for the analysis of genetic polymorphism is described below.

Analytical Method 1

Figure 5:
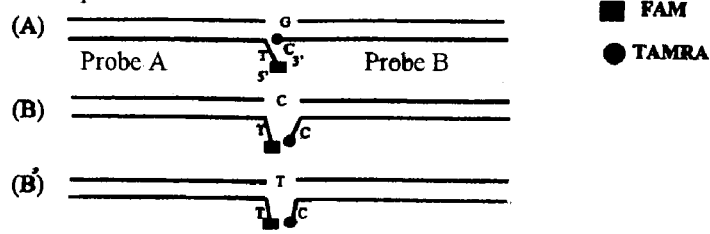
FIG. 5 is a schematic view showing a method for the analysis of genetic polymorphism using the flap endonuclease mutant of the present invention.
Figure 5:
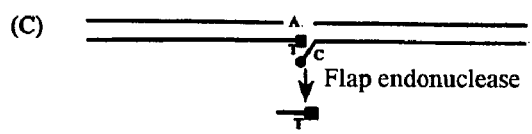
Figure 5:
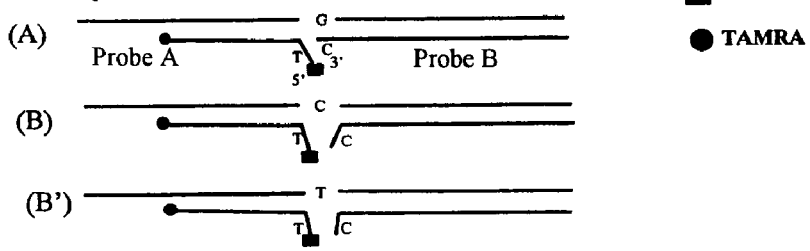
Figure 5:
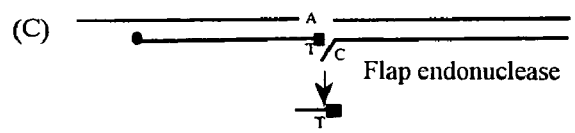
Figure 5:
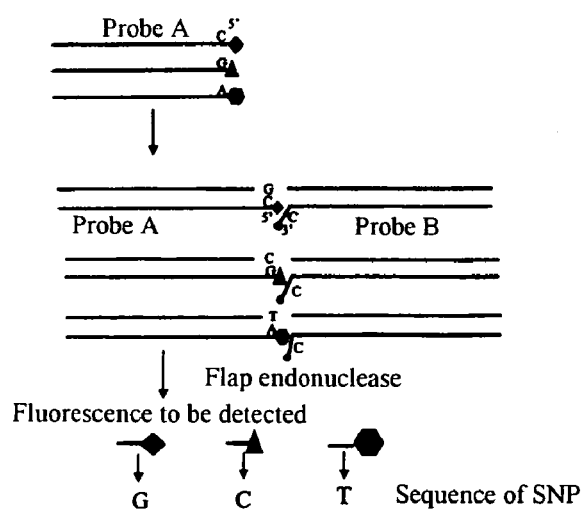

SNP analysis shown in FIG. 5 is taken as an example.

FAM and TAMRA in FIG. 5 represent a fluorescent dye, respectively and -A- represents a normal nucleotide in the absence of any SNP and -G-, -C-, and -T- represent nucleotides in the presence of polymorphism.

(a) An oligonucleotide having a nucleotide sequence complementary to sample DNA with a SNP site is synthesized such that its 5' end extends to a position corresponding to the SNP site and the 5' end is a nucleotide (T) capable of forming a base pair with the nucleotide (A) on the sample DNA in the absence of the SNP, and the oligonucleotide is used as probe A. Next, an oligonucleotide having a nucleotide sequence complementary to the sample DNA with a SNP site is synthesized such that its 3' end extends to a position corresponding to the SNP site and the 3' end is a nucleotide (C or G) other than the nucleotide (A) on the sample DNA in the absence of the SNP and its complementary nucleotide (T) capable of forming a base pair with the nucleotide (A), and the oligonucleotide is used as probe B. The 5' end of probe A and the 3' end of probe B are fluorescently labeled with a dye that would not emit fluorescence or that would emit fluorescence of a lowered intensity, due to the FRET effects generated upon contact of these ends.

Examples of combinations of fluorescent dyes that produce the FRET effects include a combination of TAMRA and FAM, and a combination of BHQ-1 and TET, HEX, or FAM. When the 5' end of probe A is labeled with FAN, for example, the 3' end of probe B may be labeled with TAMRA.

(b) Subsequently the probes A and B are annealed to the sample DNA. The structure of the double-stranded DNA after annealing differs between when the SNP is present and when absent.

[In the Presence of SNP]

When probe B with C at the 3' end is used, in the presence of polymorphism at a SNP site of the sample DNA, the nucleotide at the SNP site of the sample DNA is either G, C or T.

1) In the case of G, because it is complementary to the nucleotide (C) at the 3' end of probe B, forming a base pair, a 3' projection structure is not formed (see FIG. 5(1)(A)).

2) In the case of C, because the nucleotide (T) at the 5' end of probe A or the nucleotide (C) at the 3' end of probe B does not form a base pair with the nucleotide (G) at the SNP site of the sample DNA, both the nucleotide (T) at the 5' end of probe A and the nucleotide (C) at the 3' end of probe B form a projection structure, and the nucleotide sequence portions of probes A and B complementary to the sample DNA do not form continuous base pairs with the sample DNA, resulting in a gap (see FIG. 5(1)(B)).

3) In the case of T, as in 2) above, because the nucleotide (T) at the 5' end of probe A or the nucleotide (C) at the 3' end of probe B does not form a base pair with the nucleotide (T) at the SNP site of the sample DNA, both the nucleotide (T) at the 5' end of probe A and the nucleotide (C) at the 3' end of probe B form a projection structure, and the nucleotide sequence portions of probes A and B complementary to the sample DNA do not form continuous base pairs with the sample DNA (see FIG. 5(1)(B')).

Similarly, when probe B with (G) at the 3' end is used, in the presence of polymorphism at a SNP site of the sample DNA, the structure shown in FIG. 5(1)(A), (B) or (B') should be formed.

[In the Absence of SNP]

In contrast, in the absence of polymorphism at a SNP site of the sample DNA, in other words, if the nucleotide at the SNP site of the sample DNA is (A), the 5' end of probe A is T and forms a base pair, and the 3' end of probe B is (C) or (G) and does not form a base pair with the nucleotide (A) at the SNP site of the sample DNA, resulting in a projection end. Thus, the structure will be the nick structure with 3' projection shown in FIG. 1, and the 5' end of probe A and the nucleotide sequence portion complementary to the sample DNA excluding the flap portion of probe B form a continuous base pairs with the sample DNA without deletion sites (see FIG. 5(1)(C)).

(c) Next, the flap endonuclease mutant, a reagent for the analysis of genetic polymorphism of the present invention, is applied to the probes A and B annealed to the DNA sample.

In the presence of the SNP in the sample DNA, the flap endonuclease mutant does not act on the DNA substrates shown in (A), (B) and (B') of FIG. 5(1), so the fluorescent dye TAMRA of probe A and the fluorescent dye FAM of probe B are in proximity, resulting in the lack of fluorescence due to the FRET effect.

In contrast, in the absence of the SNP, the nucleotide sequence has a nick structure with a 3' projection, so the flap endonuclease mutant recognizes the structure as a substrate and cleaves the 5' end of probe A, and fluorescence is produced because the fluorescent dye TAMRA is not in proximity to the fluorescent dye FAM.

Therefore, the presence/absence of the SNP can be determined by detecting the presence/absence of fluorescence.

Analytical Method 2

Analytical method 2 is shown in FIG. 5(2).

This method is carried out in the same manner as the analytical method 1, except that the 3' end and the 5' end of probe A are labeled with a fluorescent dye that generates FRET effects upon proximity (e.g., a combination of TAMRA and FAM), respectively, and probe B is not subjected to fluorescent labeling. In such a case, a molecular length of probe A is determined, so that the fluorescent dyes at the ends are close to each other and fluorescence intensity is lowed due to the FRET effects (e.g., 20-mer or smaller).

In the presence of SNP, probe B does not have a 3' projection structure (FIG. 5(2)(A)), or a nucleotide sequence portion complementary to the sample DNA of probe A or probe B generates a gap between itself and the sample DNA instead of forming a continuous base pair (FIG. 5(2)(B) and (B')), as with the case of the analytical method 1. When SNP is present in the sample DNA, accordingly, any of the flap endonuclease mutants used would not act, and fluorescence intensity becomes weak due to the FRET effects. In the absence of SNP, however, a 3' projection nick structure is formed. A flap endonuclease mutant recognizes such structure as a substrate, the 5' end of probe A is cleaved (FIG. 5(2)(C)), a fluorescent dye, TAMRA, is separated from the position in proximity to FAM, and the fluorescence intensity is increased. Accordingly, observation of fluorescence intensity enables determination of the presence or absence of SNP.

According to this fluorescent labeling technique, the ends of probe A are each labeled with a different fluorescent dye, and the 3' end of probe B is not subjected to fluorescent labeling. When probes form a nick with 3' projection or double flap structure with the target gene in the analysis of genetic polymorphisms, accordingly, a flap strand can be cleaved without lowering enzyme activity. Thus, analysis can be performed with high sensitivity.

When a probe forms a 3' projection structure between itself and the target gene in the analysis of genetic polymorphisms, the enzyme activity is not lowered, and analysis can thus be performed with high sensitivity.

Analytical Method 3

The method shown in FIG. 5(3) is used to determine the nucleotide involved in the SNP.

This method uses three types of probe A with different 5' ends, for example C, G and A, and these 5' ends are labeled with different fluorescent dyes, which are selected such that fluorescence is quenched due to the FRET effect resulting from interaction with a fluorescent dye used to label the 3' end of probe B. However, the other procedure is the same as analytical method 1.

If these three types of probe A are used, a nick structure with 3' projection is produced only when the 5' end nucleotide of probe A is complementary to the nucleotide of the SNP of the sample DNA, so the flap endonuclease of the present invention can cleave the 5' end of the probe A and fluorescence is produced. The type of probe A can be identified from the type of wavelength of fluorescence produced, and the nucleotide of the SNP can be determined from the 5' end nucleotide.

Analytical Method 4

Figure 6:
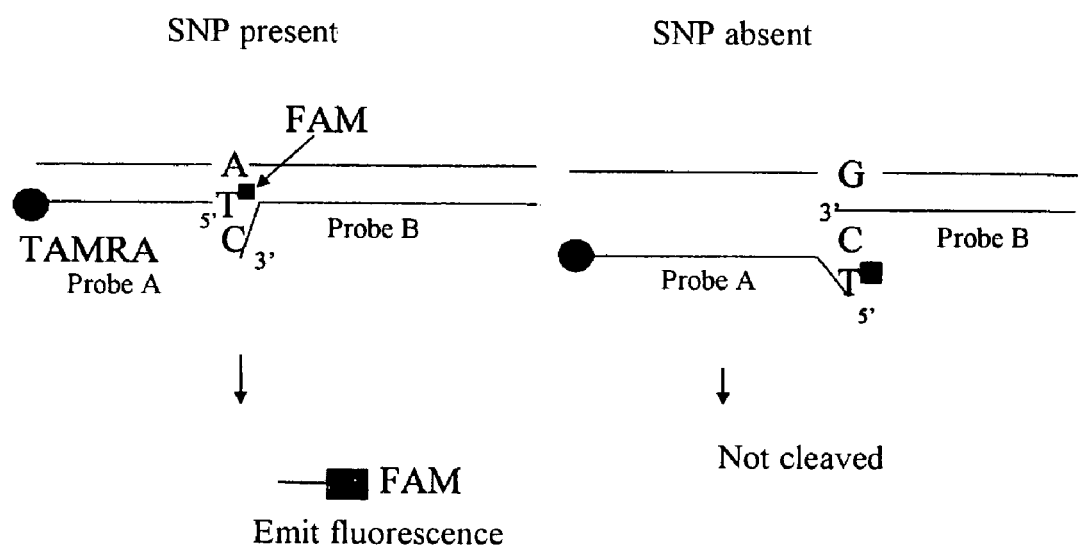
FIG. 6 is a schematic view showing other method for the analysis of genetic polymorphism using the flap endonuclease mutant of the present invention.

The method shown in FIG. 6 is used to detect a SNP easily when the nucleotide of the SNP is already determined. For example, if the nucleotide of the SNP is (A) and the nucleotide in the absence of the SNP is (G), the complementary nucleotide (T) of (A) is used for the 5' end of probe A and its 3' and 5' ends are labeled with, for example TAMRA and FAM. Preferably, this probe A is 20-mer or less than 20-mer in length as in analytical method 1. In addition, the 3' end nucleotide of the probe should be the complementary nucleotide (C) of nucleotide (G), which is the nucleotide in the absence of the SNP.

In the presence of the SNP in the sample DNA, since a 3' projection nick structure is formed when the sample DNA is annealed to probes A and B, the application of the flap endonuclease of the present invention will result in the cleavage of the 5' end of probe A, inducing the fluorescent dye (FAM) labeled on the 5' end to emit fluorescence. In the absence of the SNP, on the other hand, the nucleotide (C) at the 3' end of probe B forms a base pair with the nucleotide (G), which is the nucleotide in the absence of the SNP in the sample DNA, resulting in the absence of a 3' projection structure (a 5' single flap structure), so cleavage will not occur. Therefore, the fluorescent dyes used to label both ends of probe A are quenched due to the FRET effect.

Therefore, if the SNP nucleotide is already known, the probes can be configured as described above to analyze the SNP simply with one time testing.

Analytical Method 5

Figure 7:
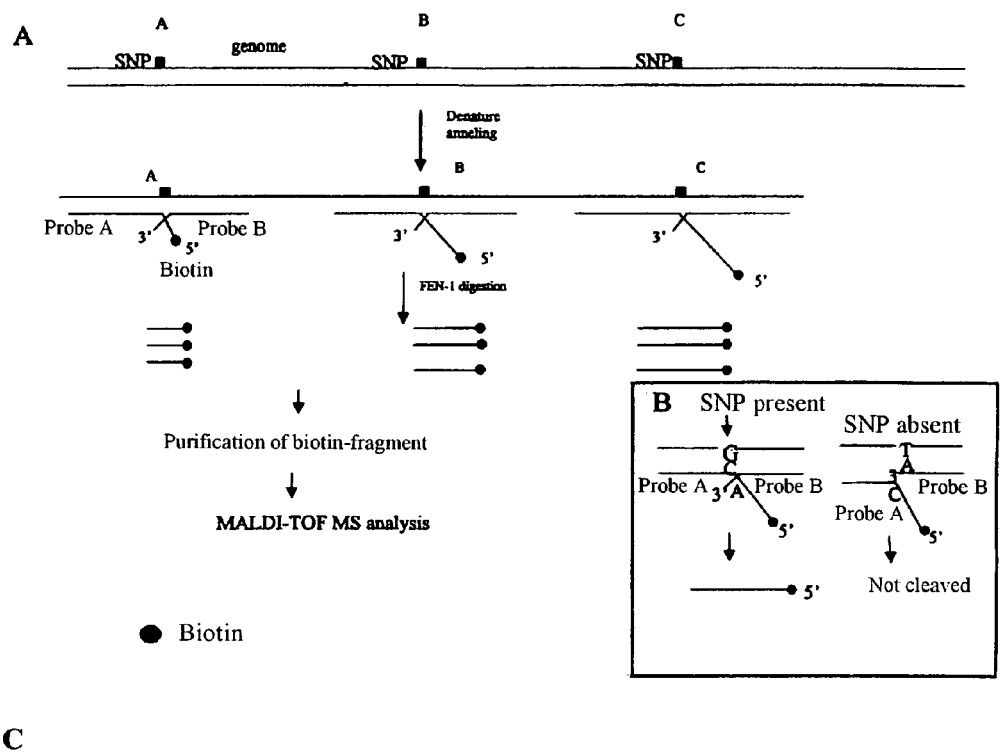
FIG. 7 is a schematic view showing other method for the analysis of genetic polymorphism using the flap endonuclease mutant of the present invention and depicts SEQ ID NO. 55 and SEQ ID NO. 56.
Figure 7:
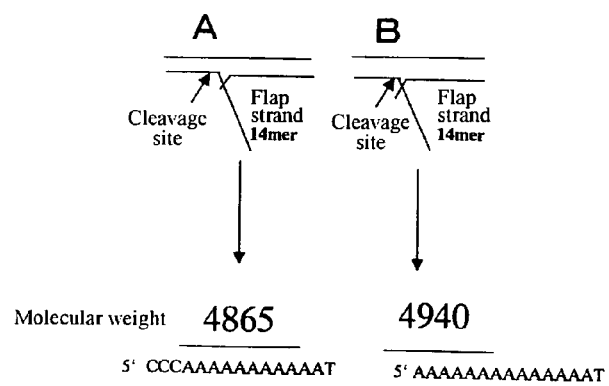

The method shown in FIG. 7 is used to analyze a number of SNPs in a genome in a simultaneous manner.

For example, if there are SNPs at positions A, B and C on a genome, probes A and B are prepared as shown in FIG. 7B. In probe A, the nucleotide C is used for the junction which is the complementary nucleotide for the SNP nucleotide G. The 3' end nucleotide of probe B should be the complementary nucleotide (A) of nucleotide (T), which is the nucleotide in the absence of the SNP. When these probes are annealed to the genome DNA, a double flap structure is formed in the presence of SNPs, and the flap endonuclease mutant of the present invention cleaves the structure at the point one nucleotide from the junction. In the absence of SNPs, on the other hand, a single flap structure is formed and cleavage will not occur.

Probe A used in this analytical method is synthesized such that the 5' end flap varies in length according to the SNP site detected, and the 5' end is linked with biotin. For example, as shown in FIG. 7, the 5' projection ends corresponding to the SNP sites A, B and C differ by 2 to 3 nucleotides in length, and the latter the longer. By doing this, DNA fragments of different lengths are obtained by cleaving the 5' end flap with the endonuclease mutant of the present invention. Because biotin is attached to the 5' end, the DNA fragment can be purified with an avidin column, and the molecular weight of the purified DNA fragment can be determined by mass spectrometry (MS). Because the length of the DNA fragment obtained varies depending on the SNP site, the SNP site can be identified based on the molecular weight determined. MALDI-TOF MS can be used to simultaneously analyze 384 specimens, each of which may contain 10 or more SNPs.

In the above technique, biotin is bound to the 5' end of probe A in order to purify a DNA fragment. With the use of a DNA purification means, such as ZipTip, a DNA fragment can be purified without the use of biotin, and a molecular weight of such fragment can then be assayed in the same manner as described above.

The molecular weights of nucleotides that constitute DNA vary from one another. Even if the 5' end flaps are of the same length, accordingly, a molecular weight of a flap strand can be altered by modifying the combination of nucleotides that constitute such flap, and the molecular weight of the cleaved DNA fragment may be assayed to identify the cleaved flap. As shown in FIG. 7C, for example, even if both 5' flap strands are determined to be the same size of 14-mer, the molecular weight of a fragment can be 4,865 and that of the other fragment can be 4,940, depending on differences in nucleotides that constitute such fragments. Thus, these fragments can be distinguished from each other. Accordingly, nucleotides that constitute a 5' flap strand are designed, and the molecular weight of the cleaved DNA fragment is assayed, in order to identify the cleaved flap. Thus, the SNP site corresponding thereto can be identified.

As the flap strand becomes longer, cleavage thereof becomes difficult due to a flap endonuclease mutant. By varying the combination and the length of nucleotides, flap strands of a wide range of molecular weights can be constructed within the range of flap strand length that the flap endonuclease mutant can effectively acts on.

Analytical Method 6

Genetic polymorphisms are classified as follows: the identical SNPs are present in the genomic gene and in the allele (homozygous type); and different SNPs are present therein (heterozygous type). According to the present invention, the presence or absence of SNP in the target gene sample can be easily detected, and whether or not the detected SNP is of a homozygous or heterozygous type can also be easily determined, when the SNP nucleotide has been identified.

Figure 20:
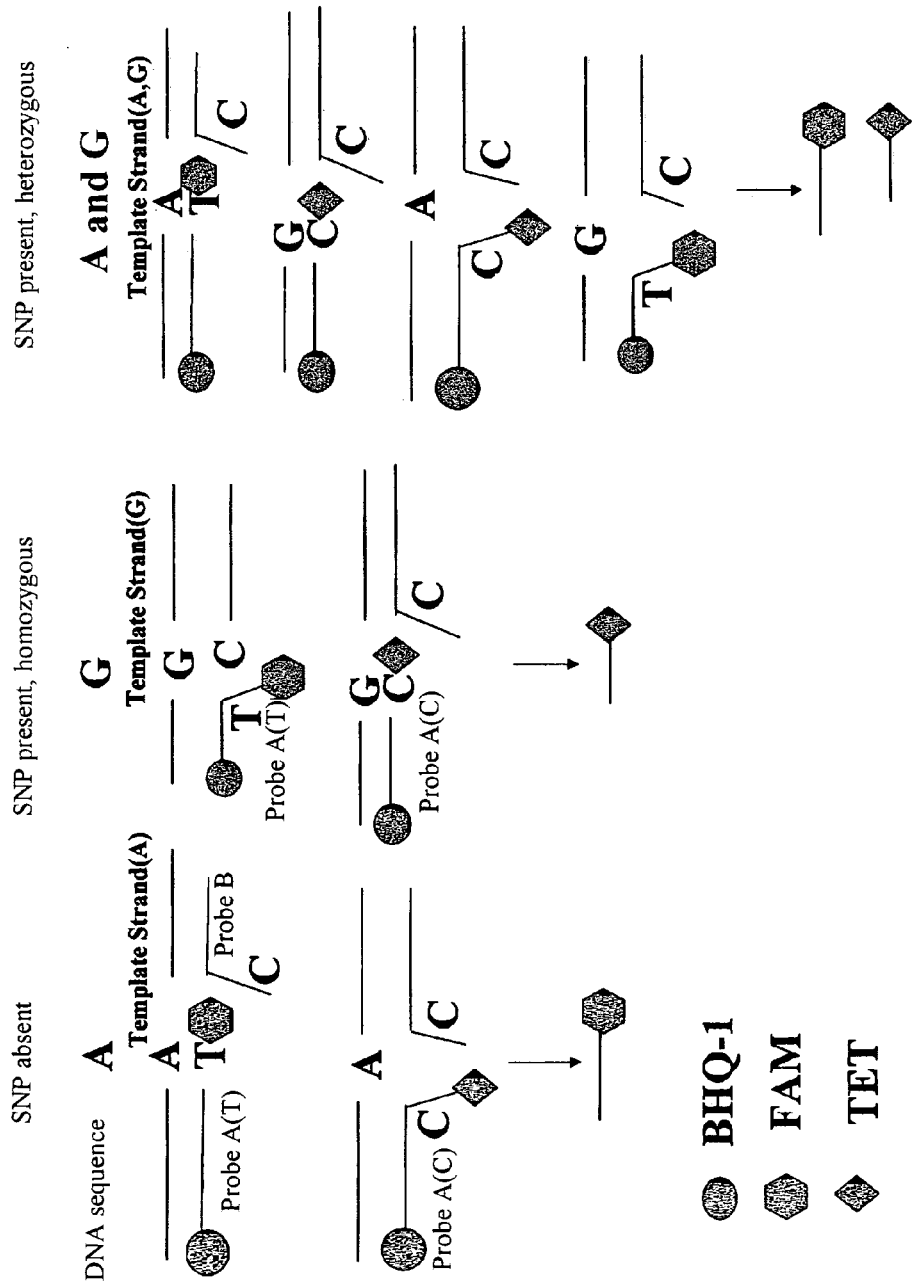
FIG. 20 is a schematic view showing a method for detecting the presence or absence of SNP in the target DNA and determining whether the SNP is homozygous or heterozygous, using the mutant enzyme of the present invention.

This technique is hereafter described with reference to FIG. 20. When there is no SNP and a normal nucleotide is A or when an SNP nucleotide is G, for example, probe A(T) comprising a 5' end nucleotide T and probe A(C) comprising a 5' end nucleotide C are synthesized, and both ends thereof are labeled with different fluorescent dyes. In such a case, the 5' end of probe A(T) is labeled with FAM and that of probe A(C) is labeled with TET, for example. Thus, both the 5' ends are labeled with different fluorescent dyes.

Subsequently, probe A(T), probe A(C), and probe B are annealed to the target DNA, and the mutant enzyme of the present invention is allowed to act thereon. In the absence of SNP (a normal nucleotide A), only probe A(T) forms a nick structure with 3' projection, it is cleaved with the enzyme of the present invention, and fluorescence derived from a fluorescent dye FAM is detected.

When SNPs are homozygous (i.e., both SNP nucleotides are G), only probe A(C) forms a nick structure with 3' projection, it is cleaved with the enzyme of the present invention, and fluorescence derived from a fluorescent dye TET is detected.

When SNPs are heterozygous (i.e., SNP nucleotides are A and G), probe A(T) and probe A(C) each form a nick structure with 3' projection, they are each cleaved with the enzyme of the present invention, and two types of fluorescence having different wavelength derived from TET and from FAM are detected.

Under other conditions, a probe forms a double flap structure with a gap or a single flap structure without a 3' projection. Thus, such probe is not cleaved with the enzyme of the present invention.

Thus, the presence or absence of SNP and whether SNP is of a homozygous or heterozygous type can be simultaneously detected by using two types of probe A having different 5' end nucleotides, allowing the mutant enzyme of the present invention to act on the analyte DNA, and detecting the resulting fluorescence wavelength.

The following examples illustrate the present invention, but are not intended to limit the scope of the invention.

EXAMPLES

Example 1

Preparation of a Mutant

The gene of mutant Y33A was prepared as follows.

Common primers and the primers which have mutation (primers for preparation of Y33A) were synthesized as shown below. First, PCR (after heating for five minutes at 96° C., DNA polymerase was added, then a cycle of 96° C. for 1 minute, 55° C. for 2 minutes and 70° C. for 2 minutes was repeated 25 times) was performed using a PET11a plasmid containing the gene (SEQ ID No. 1) encoding the wild type flap endonuclease-1 (FEN-1) from *Pyrococcus horikoshii* as the template, and using the FEN-U primer containing a restriction site (NdeI) and the Y33A-R primer which has mutation, and the FEN-R primer containing a restriction site (XhoI) and the Y33A-U primer which has mutation, to prepare two fragments having mutation, then PCR (using the same conditions as above) was performed with these fragments as templates using the FEN-U and FEN-R primers to introduce mutations, and restriction sites on both sides of the gene.

The nucleotide sequence of the structural gene for the flap endonuclease mutant Y33A is shown in SEQ ID No. 3.

The genes for the other flap endonuclease mutants Y33L, F35Y, F79A, F79H, Y33AF79A, F278AF279A, and Y33AF35A were prepared in the same manner as above. The nucleotide sequences for these structural genes are shown in SEQ ID Nos. 5, 7, 9, 11, 13, 15, and 53, respectively, of the Sequence Listing.

Common primers;

```
FEN-U
                                           (SEQ ID No. 17)
5'-GGGAATTCCTGCAGATCGCATATGGGTGTTCCTATCGGTGAC-3'

FEN-R
                                           (SEQ ID No. 18)
5'-ACGCGTCGACGTCCGCTCGAGCGGTTAGGGTTTCTTTTTAACGAACC
AAC-3'

Primers for preparation of Y33A;
Y33A-U
                                           (SEQ ID No. 19)
5'-ATAGATGCCCTAAACGCCATCGCGCAGTTTTTATCAACGATACGACA
G-3'

Y33A-R
                                           (SEQ ID No. 20)
5'-CTGTCGTATCGTTGATAAAAACTGCGCGATGGCGTTTAGGGCATCTA
T-3'

Primers for preparation of Y33L;
Y33L-U
                                           (SEQ ID No. 21)
5'-ATAGATGCCCTAAACGCCATCCTGCAGTTTTTATCAACGATACGACA
G-3'

Y33L-R
                                           (SEQ ID No. 22)
5'-CTGTCGTATCGTTGATAAAAACTGCAGGATGGCGTTTAGGGCATCTA
T-3'

Primers for preparation of F35Y;
F35Y-U
                                           (SEQ ID No. 23)
5'-GCCCTAAACGCCATCTATCAGTATTTATCAACGATACGACAGCGTGA
T-3'

F35Y-R
                                           (SEQ ID No. 24)
5'-ATCACGCTGTCGTATCGTTGATAAATACTGATAGATGGCGTTTAGGG
C-3'

Primers for preparation of F79A;
F79A-U
                                           (SEQ ID No. 25)
5'-GGTATTAAGCCGGCCTACGTCGCGGATGGAAAGCCTCCGGAATTTAA
A-3'

F79A-R
                                           (SEQ ID No. 26)
5'-TTTAAATTCCGGAGGCTTTCCATCCGCGACGTAGGCCGGCTTAATAC
C-3'

Primers for preparation of F79H;
F79H-U
                                           (SEQ ID No. 27)
5'-GGTATTAAGCCGGCCTACGTCCATGATGGAAAGCCTCCGGAATTTAA
A-3'

F79H-R
                                           (SEQ ID No. 28)
5'-TTTAAATTCCGGAGGCTTTCCATCATGGACGTAGGCCGGCTTAATAC
C-3'
```

```
-continued
Primers for preparation of F278AF279A;
F278AF279A-U
                                         (SEQ ID No. 29)
5'-CTTTACGCTATTAAGGAAGCGGCGCTTAACCCTCCTGTCACTAATGA

A-3'

F278AF279A-R
                                         (SEQ ID No. 30)
5'-TTCATTAGTGACAGGAGGGTTAAGCGCCGCTTCCTTAATAGCGTAAA

G-3'

Primers for preparation of Y33AF35A;
Y33AF35A-U
                                         (SEQ ID No. 39)
5'-ATAGATGCCCTAAACGCCATCGCGCAGGCGTTATCAACGATAAGACA

GAGG-3'

Y33AF35A-R
                                         (SEQ ID No. 40)
5'-CCTCTGTCTTATCGTTGATAACGCCTGCGCGATGGCGTTTAGGGCAT

CTAT-3'
```

The Y33AF79A gene (SEQ ID No. 13) was prepared by purifying a plasmid containing the above Y33A gene (SEQ ID No. 3) and using the resultant as a template and the primers for F79A (SEQ ID NOs. 25 and 26).

Next, PET11a (manufactured by Novagen) was digested with the restriction enzymes NdeI and XhoI and purified, and the restriction products were linked to each mutant gene described above by allowing to react at 16° C. for 2 hours using T4 ligase. A part of the linked DNA was introduced into competent cells of E. coli-XL1-BlueMRF, and colonies from each transformant were obtained. Each expression plasmid was purified from the obtained colonies by the alkali method, and obtained.

Example 2

Expression of Recombinant Gene

Competent cells of E. coli BL 21 (DE3) (manufactured by Novagen) were thawed, 0.1 ml of the thawed competent cells was transferred into each of two Falcon tubes, 0.005 ml each of the solutions of the expression plasmids above was added, the mixture was kept on ice for 30 minutes, heat shock was applied at 42° C. for 30 seconds, 0.9 ml of SOC medium was added and the mixture was incubated at 37° C. for one hour with shaking.

An appropriate amount of the obtained culture was placed on a 2YT agar plate containing ampicillin and incubated at 37° C. overnight to obtain each transformant.

Each of these transformants was incubated in 2YT medium (2 liters) containing ampicillin at 37° C. until absorbance at 660 nm reached 0.4, and then IPTG (isopropyl-b-D-thiogalactopyranoside) was added at 1 mM and the mixture was incubated at 30° C. for 4 hours. After incubation, cells were harvested by centrifugal separation (6,000 rpm, 20 minutes).

Example 3

Purification of Mutant Enzymes

The cells collected were subjected to freeze-thawing at −20° C., respectively and two volumes of 50 mM Tris-HCl buffer (pH 8.0) as compared to the cell were added to obtain a suspension. Each of the resultant suspensions was heated at 85° C. for 30 minutes, centrifuged (11,000 rpm, 20 minutes), adsorbed to a HiTrapSP (manufactured by Pharmacia) column, and eluted by NaCl concentration gradient to obtain active fractions. These fractions represented solutions of purified Y33A, Y33L, F35Y, F79A, F79H, F278AF279A, Y33AF35A, and Y33AF79A.

Example 4

Conditions for Enzymatic Reaction (1) Synthetic Oligonucleotide

Oligonucleotides having the following nucleotide sequences were synthesized. All of these oligonucleotides were synthesized by Hokkaido System Science company.

```
Template strand (A); 54-mer,
                                         (SEQ ID No. 31)
5'-GAGCTAGATGTCGGACTCTGCCTCAAGACGGTAGTCAACGTGCACTC

GAGGTCA-3'

Downstream strand (C-1); 28-mer,
                                         (SEQ ID No. 35)
5'-TCTTGAGGCAGAGTCCGACATCTAGCTC-3'

Upstream strand (B-1); 26-mer,
                                         (SEQ ID No. 32)
5'-TGACCTCGAGTGCACGTTGACTACCG-3'

Upstream strand (B-2); 27-mer,
                                         (SEQ ID No. 33)
5'-TGACCTCGAGTGCACGTTGACTACCGC-3'

Flap strand (C-2); 32-mer,
                                         (SEQ ID No. 36)
5'-TAACTCTTGAGGCAGAGTCCGACATCTAGCTC-3'

Flap strand (C-3); 57-mer,
                                         (SEQ ID No. 37)
5'-GCATCTGACGGATGTCAAGCAGTCCTAACTCTTGAGGCAGAGTCCGA

CATCTAGCTC-3'
```

Of these, the 5' end of the oligonucleotides downstream strand (C-1), flap strand (C-2), and flap strand (C-3) was fluorescently (FAM) labeled.

(2) Preparation of Substrates

Oligonucleotides described above were combined as (A)+ (C-1)+(B-1), (A)+(C-1)+(B-2), (A)+(C-1), (A)+(C-2)+(B-1), (A)+(C-3)+(B-2) and (A)+(C-2), boiled in 20 mM Tris-HCl buffer (pH 7.4) containing 150 mM NaCl and the solution was cooled slowly to 4° C. to anneal them. Thus each substrate was prepared. The names and structures of the substrates are shown in FIG. 1.

(3) Flap Endonuclease Activity

Two pmoles of each fluorescently (FAM)-labeled substrate and each of the mutant enzymes Y33A, Y33L, F35Y, F79A, F79L, F79H and F278AF279A were added to 10 µl of 50 mM Tris-HCl buffer (pH 8.0, 15 mM $MgCl_2$, 100 mg/ml bovine serum albumin) and allowed to react at 60° C. for 1 to 10 minutes, and activity was measured every one minute. Then, 10 µl of 95% formamide, 20 mM EDTA, and 1 mg/ml xylenecyanol were added to terminate the enzyme reaction. The solution was heated to 100° C., quenched on ice, and analyzed by 15% polyacrylamide gel (containing 7 M urea) electrophoresis (PAGE). This electrophoretic pattern was subjected to autoradiography with phospholmager (manufactured by Bio-Rad), and the molecular species and amount of the reactant were determined. Kinetics analysis was performed to calculate Km and Kcat.

(4) Substrate Specificity of Mutants

Figure 2:
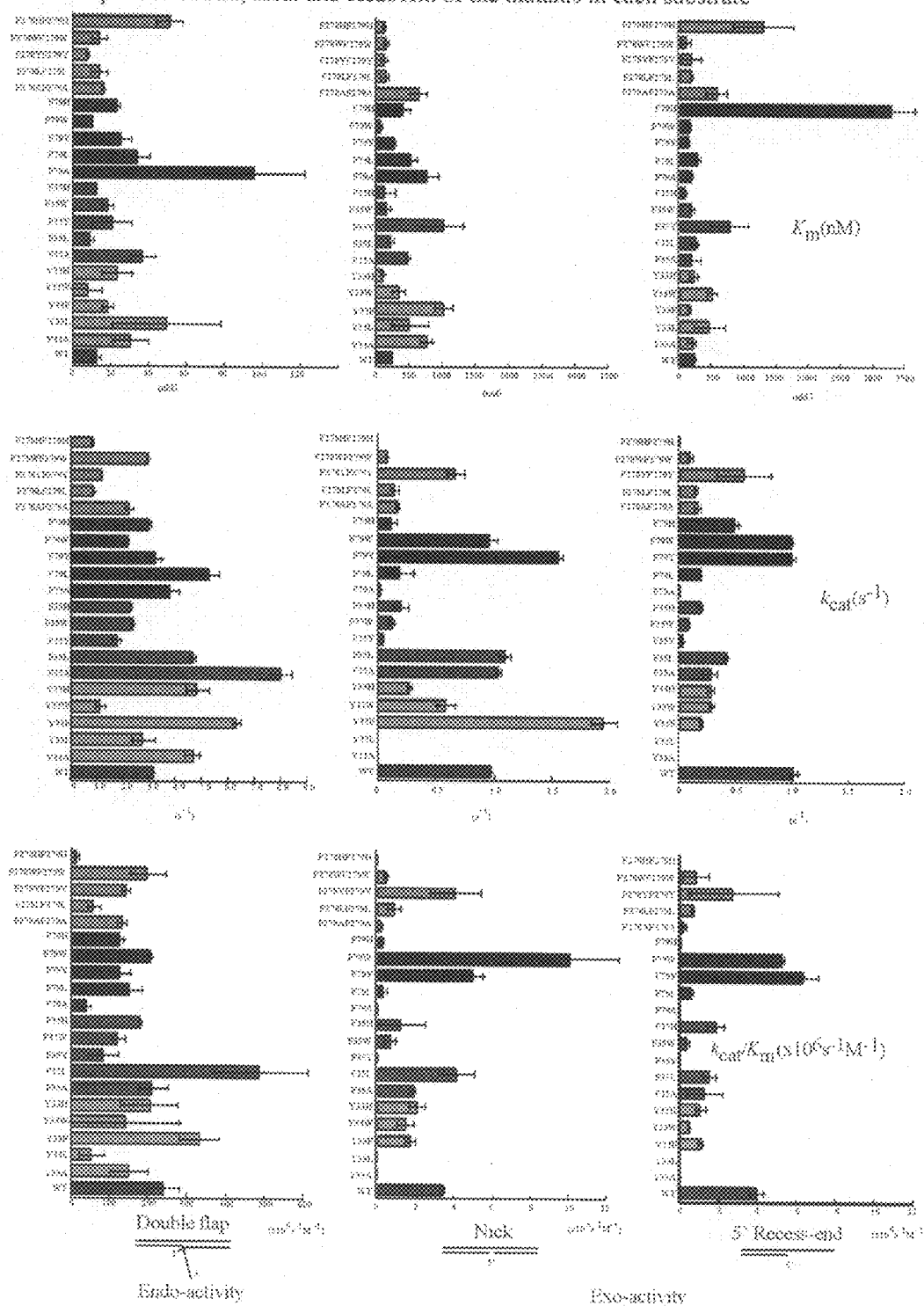
FIG. 2 is a graph showing the activity of each flap endonuclease mutant for the double flap, nick and 5' recess-end substrates.
Figure 3:
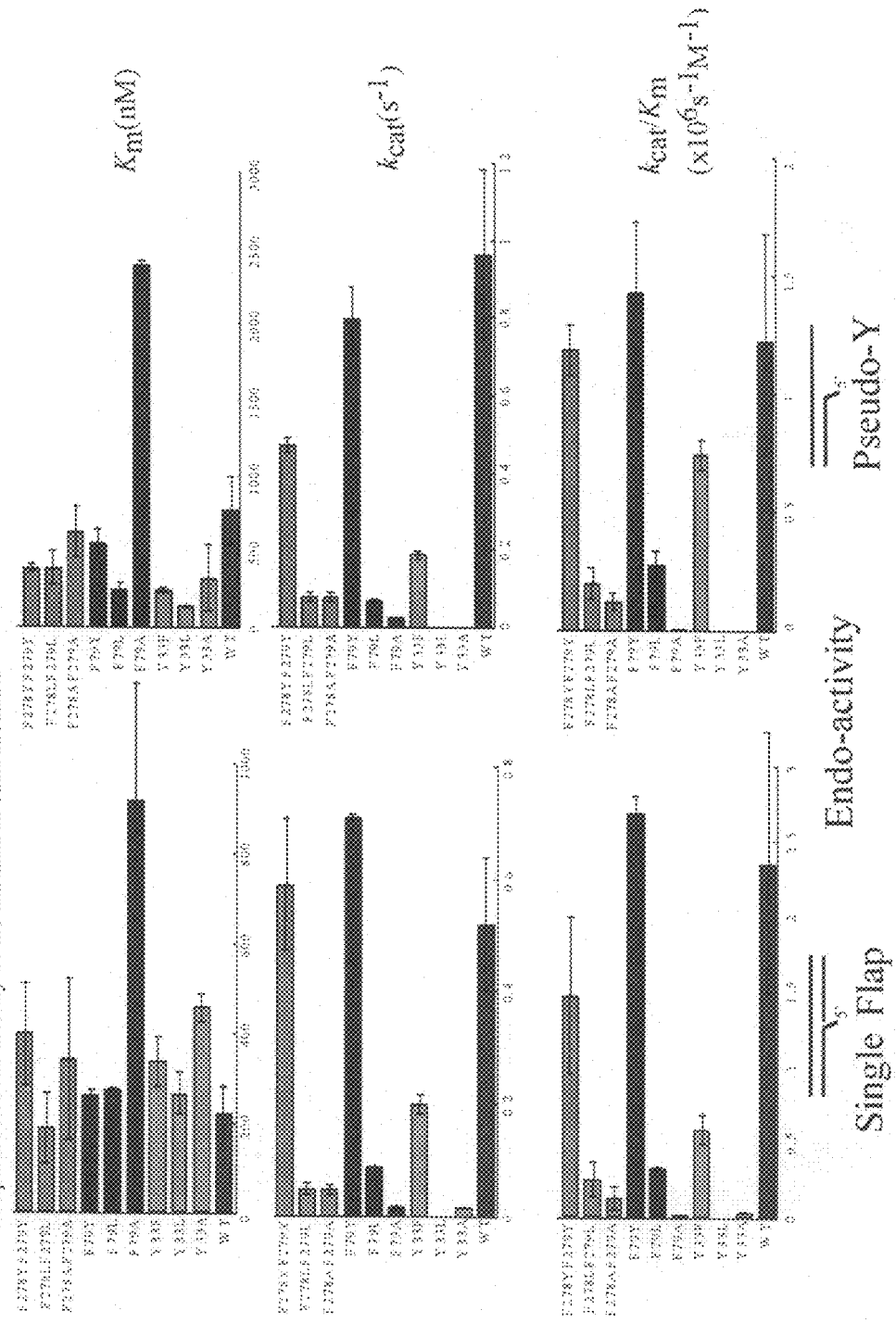
FIG. 3 is a graph showing the activity of each flap endonuclease mutant for the single flap and pseudo-Y substrates.
Figure 4:
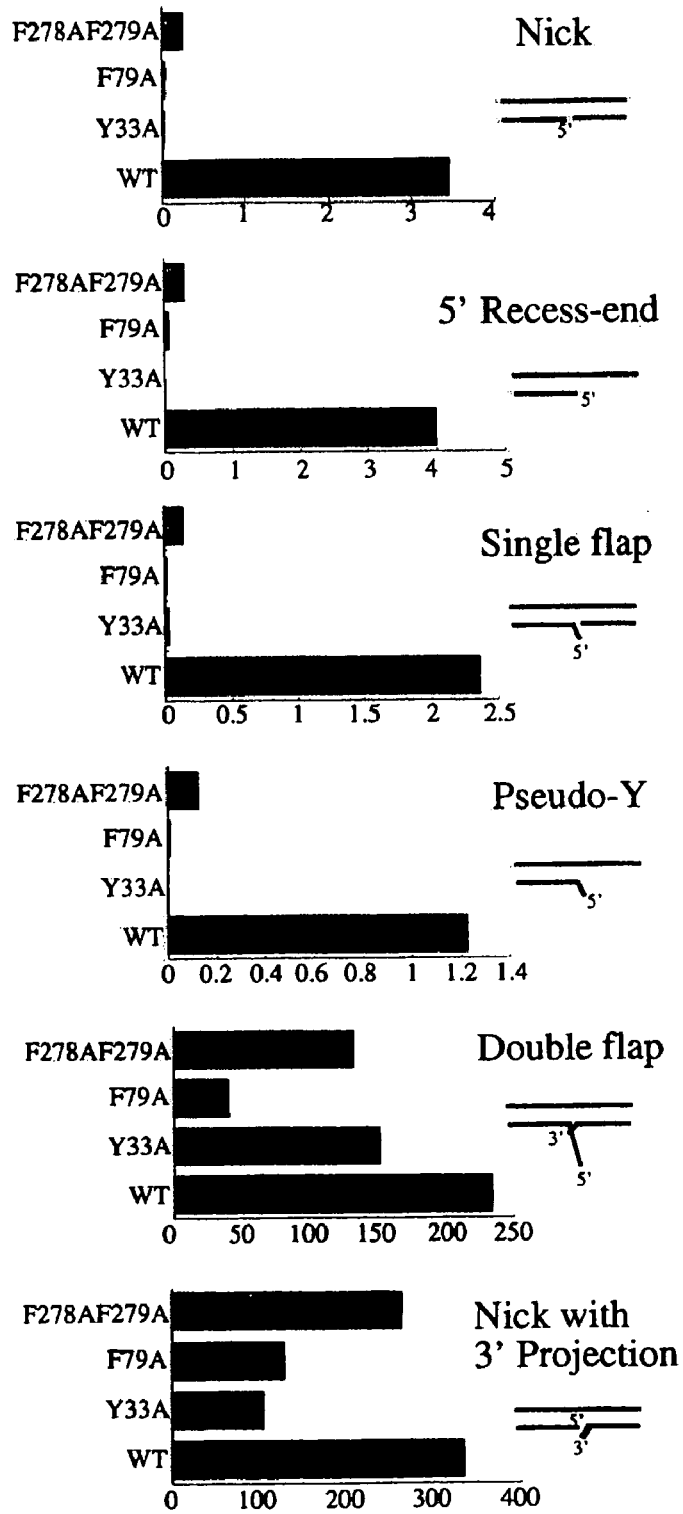
FIG. 4 is a graph showing the activity of the mutants of flap endonuclease of the present invention for the six types of substrates described above.

Changes in substrate specificity of each mutant described above as well as those of other mutants and the wild type enzymes (WT) are shown in FIGS. 2, 3 and 4. The mutants Y33A, Y33L, F35Y, F79A, F79L, F79H and F278AF279A showed markedly decreased activity for the nick, recess-end, single flap and pseudo-Y substrates. However, little change in activity was observed for the double flap and nick with 3' projection substrates compared with WT.

The substrate of the 5' end fluorescence label was cleaved by both the wild type flap endonuclease and the mutants.

Example 5

Figure 9:
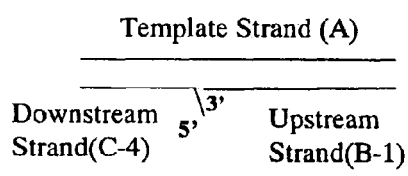
FIG. 9 is a schematic view showing the structure of the substrates used in the experiment of Example 5.
Figure 9:
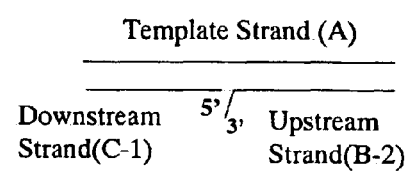
Figure 9:
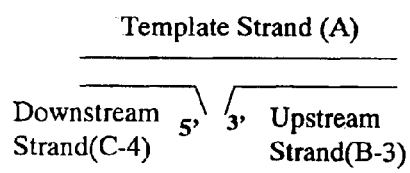

The following oligonucleotides were synthesized respectively. The 5' ends of C-1 and C-4 were fluorescently (FAM) labeled. Then, these oligonucleotides were annealed in the same manner as Example 4 to prepare the substrates having structures shown in FIG. 9.

```
Template strand (A); 54-mer,
                                        (SEQ ID No. 31)
5'-GAGCTAGATGTCGGACTCTGCCTCAAGACGGTAGTCAACGTGCACTC
GAGGTCA-3'

Upstream strand (B-3); 26-mer,
                                        (SEQ ID No. 34)
5'-TGACCTCGAGTGCACGTTGACTACCA-3'

Downstream strand (C-1); 28-mer,
                                        (SEQ ID No. 35)
5'-TCTTGAGGCAGAGTCCGACATCTAGCTC-3'

Downstream strand (C-4); 29-mer,
                                        (SEQ ID No. 38)
5'-CTCTTGAGGCAGAGTCCGACATCTAGCTC-3'
```

Structures of these substrates were three types, the single flap structure with 1-mer 5' projection (FIG. 9A), the double flap structure with a nick region with a 1-mer gap (FIG. 9B), and the nick structure with 3' projection (FIG. 9C).

Subsequently, two pmoles of each fluorescently (FAM) labeled substrate were added to 10 μm of 50 mM Tris-HCl buffer (pH 8.0, 15 mM MgCl$_2$, 100 mg/ml bovine serum albumin) and 0.1 ng or 1 ng of the wild type enzymes and the mutant enzymes F79A, Y33A and F278AF279A were further added per substrate and allowed to react at 60° C. for 5 minutes. Then, 10 μl of 95% formamide, 20 mM EDTA, and 1 mg/ml xylenecyanol were added to terminate the enzyme reaction. The solution was heated to 100° C., quenched on ice, and analyzed by 15% polyacrylamide gel (containing 7 M urea) electrophoresis (PAGE). This electrophoretic pattern was subjected to autoradiography with phosphoimager (manufactured by Bio-Rad).

Figure 8:
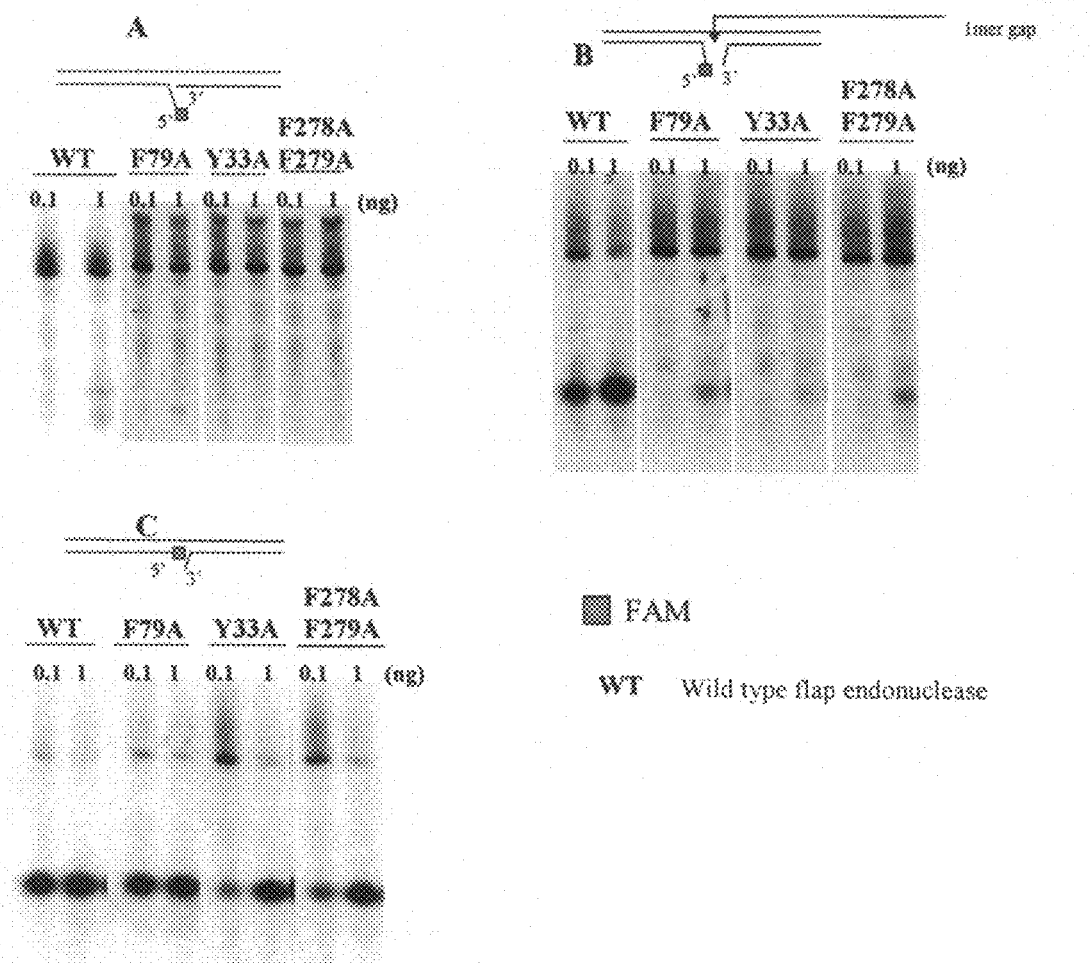
FIG. 8 is electrophoretic patterns showing the test results of substrate specificity necessary for use in the analysis of genetic polymorphism using the flap endonuclease mutant of the present invention.

Results are shown in FIG. 8. Results show that both of the wild type enzymes and the mutant enzymes of the present invention showed activity against the substrate C, but while the wild type enzymes showed activity against the substrates A and B, none of the mutant enzymes of the present invention did. Such substrate specificity shows that the flap endonuclease mutants of the present invention have sufficient capability for a reagent in an analytical method for genetic polymorphism described above.

Example 6

Figure 10:
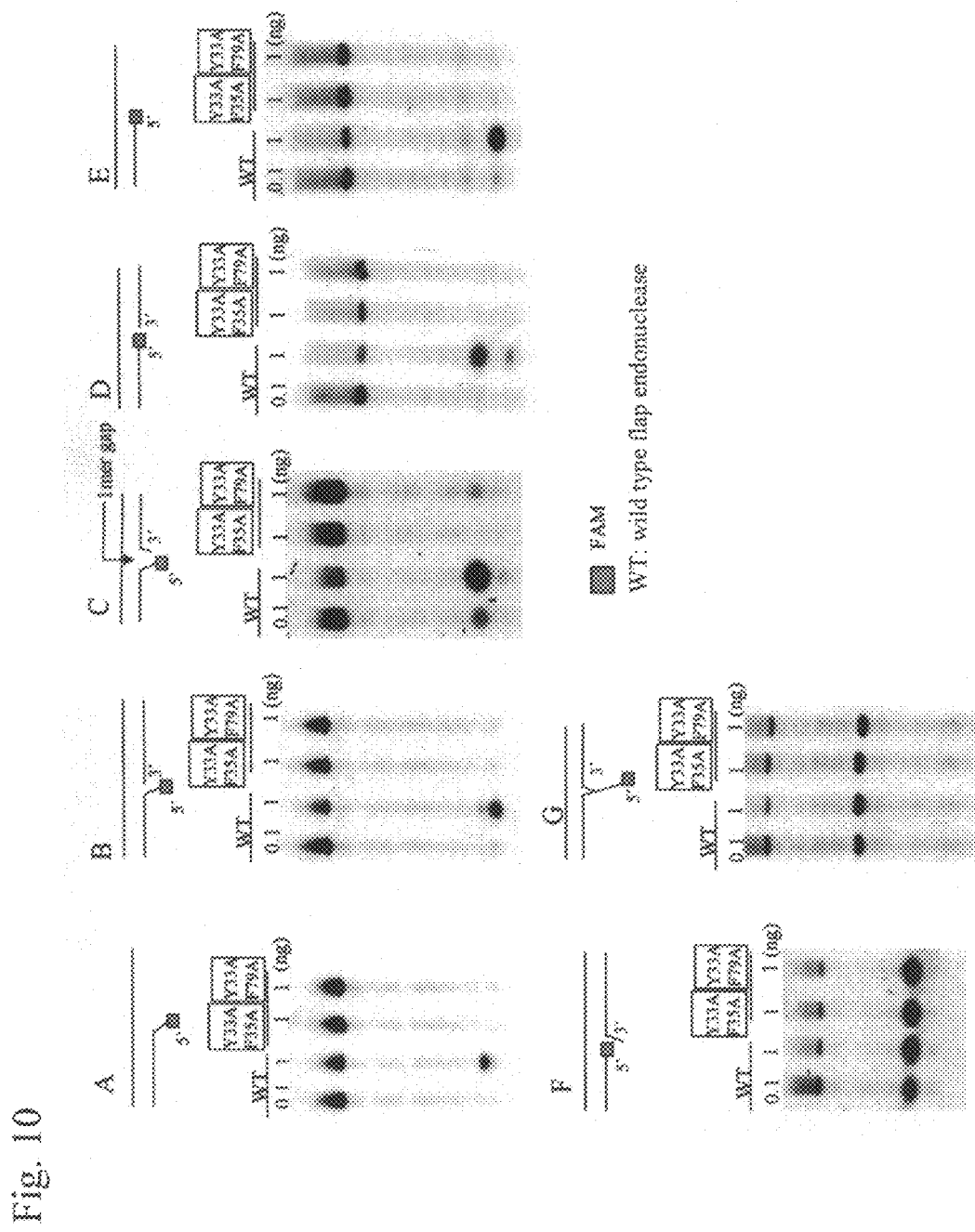
FIG. 10 is an electrophoretic photograph showing the activity of the flap endonuclease mutants of the present invention (Y33AF79A and Y33AF35A) for each substrate.

Two pmoles each of fluorescently (FAM)-labeled substrates prepared in Examples 4 and 5 (a total of 7 types) were added to 10 μl of 50 mM Tris-HCl buffer (pH 8.0, 15 mM MgCl$_2$, 100 mg/ml bovine serum albumin). Further, 0.1 ng or 1 ng of wild type enzymes and 1 ng of mutant enzymes Y33AF35A and Y33AF79A were added to each substrate, and the resultants were allowed to react at 60° C. for 5 minutes. Then, 10 μl of 95% formamide, 20 mM EDTA, and 1 mg/ml xylenecyanol were added to terminate the enzyme reaction. The solution was heated to 100° C., quenched on ice, and analyzed by 15% polyacrylamide gel (containing 7 M urea) electrophoresis (PAGE). This electrophoretic pattern was subjected to autoradiography with phospholmager (manufactured by Bio-Rad). The results are shown in FIG. 10.

According to such results, wild type enzymes exhibited the activities on all 7 types of the aforementioned substrates. In contrast, the mutant enzymes Y33AF35A and Y33AF79A exhibited the activity selectively on substrate F with the 3' projection (nick with 3' projection structure) and substrate G (a double flap structure), although they did not exhibit the activity on substrate C with 3' projection and a 1-mer gap (a double flap structure with a gap).

Example 7

The following oligonucleotides were synthesized.

```
Template strand (A); 54-mer,
                                        (SEQ ID No. 31)
5'-GAGCTAGATGTCGGACTCTGCCTCAAGACGGTAGTCAACGTGCACTC
GAGGTCA-3'

Upstream strand (B-1): 26-mer,
                                        (SEQ ID NO. 32)
5'-TGACCTCGAGTGCACGTTGACTACCG-3';

Upstream strand (B-2): 27-mer,
                                        (SEQ ID NO. 33)
5'-TGACCTCGAGTGCACGTTGACTACCGC-3'

Upstream strand (B-3): 26-mer,
                                        (SEQ ID NO. 34)
5'-TGACCTCGAGTGCACGTTGACTACCA-3'

Downstream strand (C-1-1): 20-mer,
                                        (SEQ ID NO. 41)
5'-TCTTGAGGCAGAGTCCGACA-3'

Flap strand (C-4-1): 20-mer,
                                        (SEQ ID NO. 42)
5'-CTCTTGAGGCAGAGTCCGAC-3'
```

Figure 11:
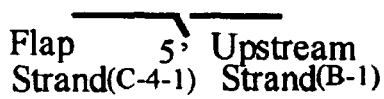
FIG. 11 is a schematic view showing the structure of the substrates prepared in Example 7.
Figure 11:
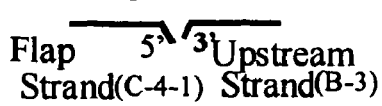
Figure 11:
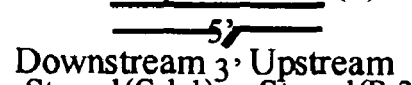

Strands C-4-1 and C-1-1 were labeled at the 5' end with FAM and at the 3' end with TAMRA, respectively, they were subjected to annealing in the same manner as in Example 4, and the substrates having the structures as shown in FIG. 11 were prepared.

Subsequently, 1 pmole each of the above fluorescently-labeled substrates was added to 10 μl of 50 mM Tris-HCl buffer (pH 8.0, 15 mM MgCl$_2$, 100 mg/ml bovine serum albumin). Further, 1 ng each of wild type enzymes and mutant enzymes were added to each substrate, and the resultants were allowed to react at 60° C. for 5 minutes. Then, 10 μl of 95% formamide, 20 mM EDTA, and 1 mg/ml xylenecyanol were added to terminate the enzyme reaction. The solution was heated to 100° C., quenched on ice, and analyzed by 15% polyacrylamide gel (containing 7 M urea) electrophoresis (PAGE). This electrophoretic pattern was subjected to autoradiography with phospholmager (manufactured by Bio-Rad).

Figure 12:
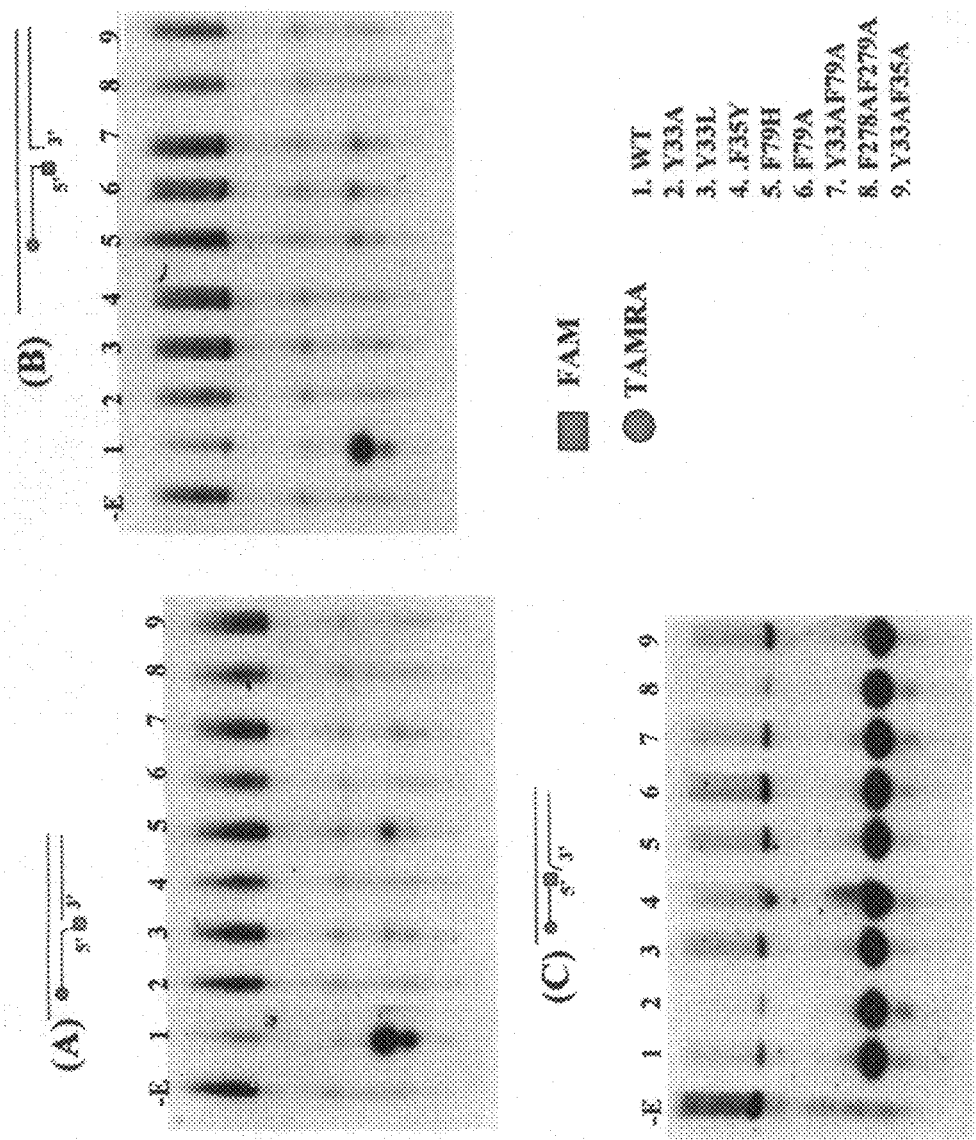
FIG. 12 is an electrophoretic photograph showing the activity of the mutant enzyme of the present invention for the substrates prepared in Example 7.

The results are shown in FIG. 12. According to such results, wild type enzymes exhibited the activities on all the substrates shown in FIG. 12 (A) to (C). In contrast, the mutant enzymes exhibited the activity selectively on substrate (C) with the 3' projection, although they did not exhibit any activity or exhibited very weak activity on substrate (A) or substrate (B) with the 3' projection and 1-mer gap.

Example 8

Ten pmoles each of fluorescently-labeled substrates prepared in Example 7 were added to 10 μl of 50 mM Tris-HCl buffer (pH 8.0, 15 mM MgCl$_2$, 100 mg/ml bovine serum albumin). Further, 10 ng each of wild type enzymes and mutant enzymes were added to each substrate, and the resultants were allowed to react at 60° C. for 5 minutes. Then, 200 μl of 50 mM Tris-HCl buffer (pH 8.0) was added, and the resultant was placed in ice to terminate the reaction. Fluorescence intensity was assayed using a fluorescent spectrophotometer (FP-750, JASCO Corporation) using a 500-nm filter with excitation/emission of 494 nm/520 nm.

Figure 13:
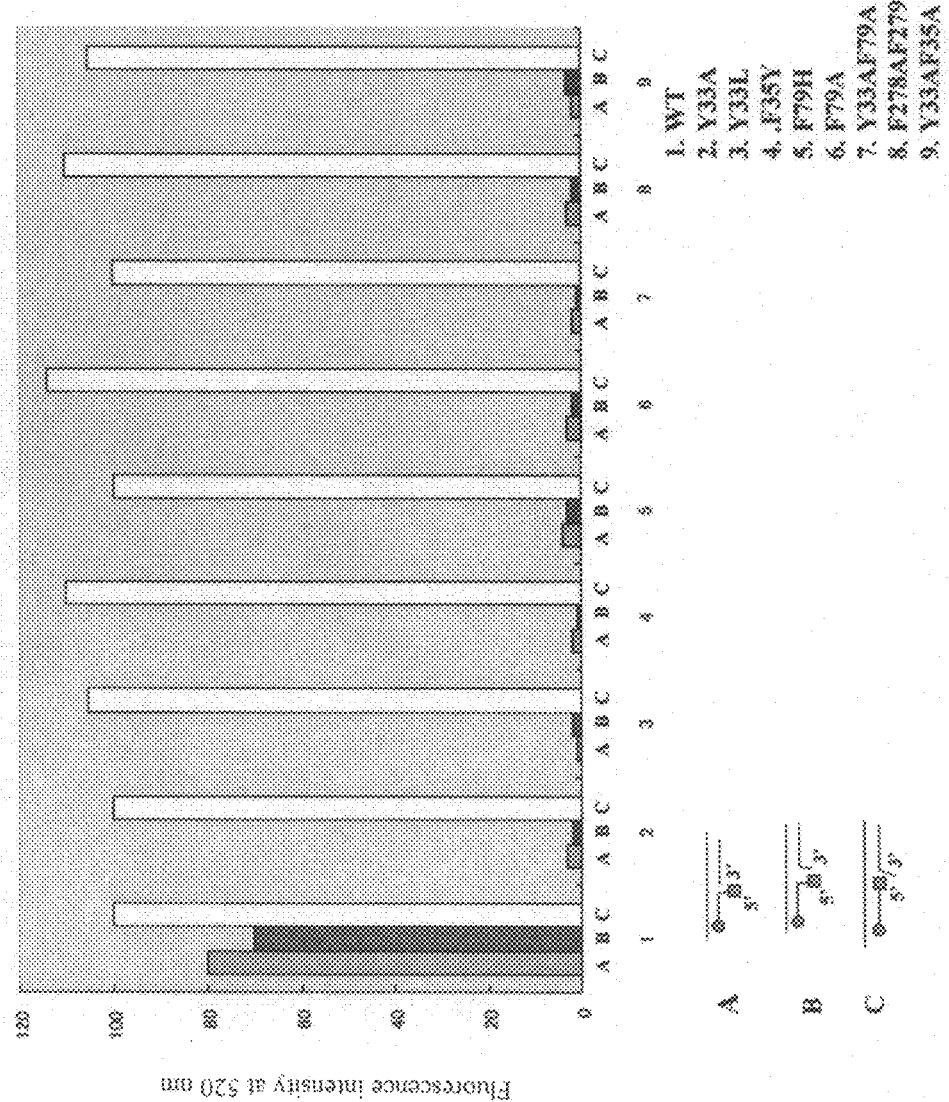
FIG. 13 is a graph showing the results of assaying the activity of the mutant enzyme of the present invention for the substrates prepared in Example 7 based on fluorescence intensity.

The results are shown in FIG. 13. In FIG. 13, numerical values of bar graphs indicate the values obtained as follows: that is, an enzyme-free sample was designated as a control, and the value of the control was subtracted from the value of the enzyme-containing sample.

According to the results, a wild type enzyme exhibited the activity on all the substrates A to C. In contrast, the mutant enzymes exhibited the activity selectively on substrate C with 3' projection; however, they did not exhibit the activity on substrate B with a 3' projection and a 1-mer gap.

Example 9

The following oligonucleotides were synthesized.

```
Template strand (A): 54-mer,
                                          (SEQ ID NO. 31)
5'-GAGCTAGATGTCGGACTCTGCCTCAAGACGGTAGTCAACGTGCACTC
GAGGTCA-3'

Upstream strand (B-1): 26-mer,
                                          (SEQ ID NO. 32)
5'-TGACCTCGAGTGCACGTTGACTACCG-3'

Upstream strand (B-2): 27-mer,
                                          (SEQ ID NO. 33)
5'-TGACCTCGAGTGCACGTTGACTACCGC-3'

Upstream strand (B-3): 26-mer,
                                          (SEQ ID NO. 34)
5'-TGACCTCGAGTGCACGTTGACTACCA-3'

Downstream strand (C-1): 28-mer,
                                          (SEQ ID NO. 35)
5'-TCTTGAGGCAGAGTCCGACATCTAGCTC-3'

Flap strand (C-4): 29-mer,
                                          (SEQ ID NO. 38)
5'-CTCTTGAGGCAGAGTCCGACATCTAGCTC-3'
```

The 3' ends of B-1, B-2, and B-3 were labeled with TAMRA, and the 5' ends of C-1 and C-4 were labeled with FAM. Subsequently, these oligonucleotides were subjected to annealing in the same manner as in Example 4 to prepare substrates having the structures shown in FIG. 14.

Ten pmoles each of the above fluorescently-labeled substrates were added to 10 μl of 50 mM Tris-HCl buffer (pH 8.0, 15 mM MgCl$_2$, 100 mg/ml bovine serum albumin). Further, 50 ng of wild type enzymes or 400 ng of mutant enzymes were added to each substrate, and the resultants were allowed to react at 60° C. for 5 minutes. Then, 200 μl of 50 mM Tris-HCl buffer (pH 8.0) was added, and the resultant was placed in ice to terminate the reaction. Fluorescence intensity was assayed using a fluorescent spectrophotometer (FP-750, JASCO Corporation) using a 500-nm filter with excitation/emission of 494 nm/520 nm. The enzyme-free samples were designated as the controls, and the values of the controls were subtracted from the values of the enzyme-containing samples. The determined values represent the values of the samples.

Figure 15:
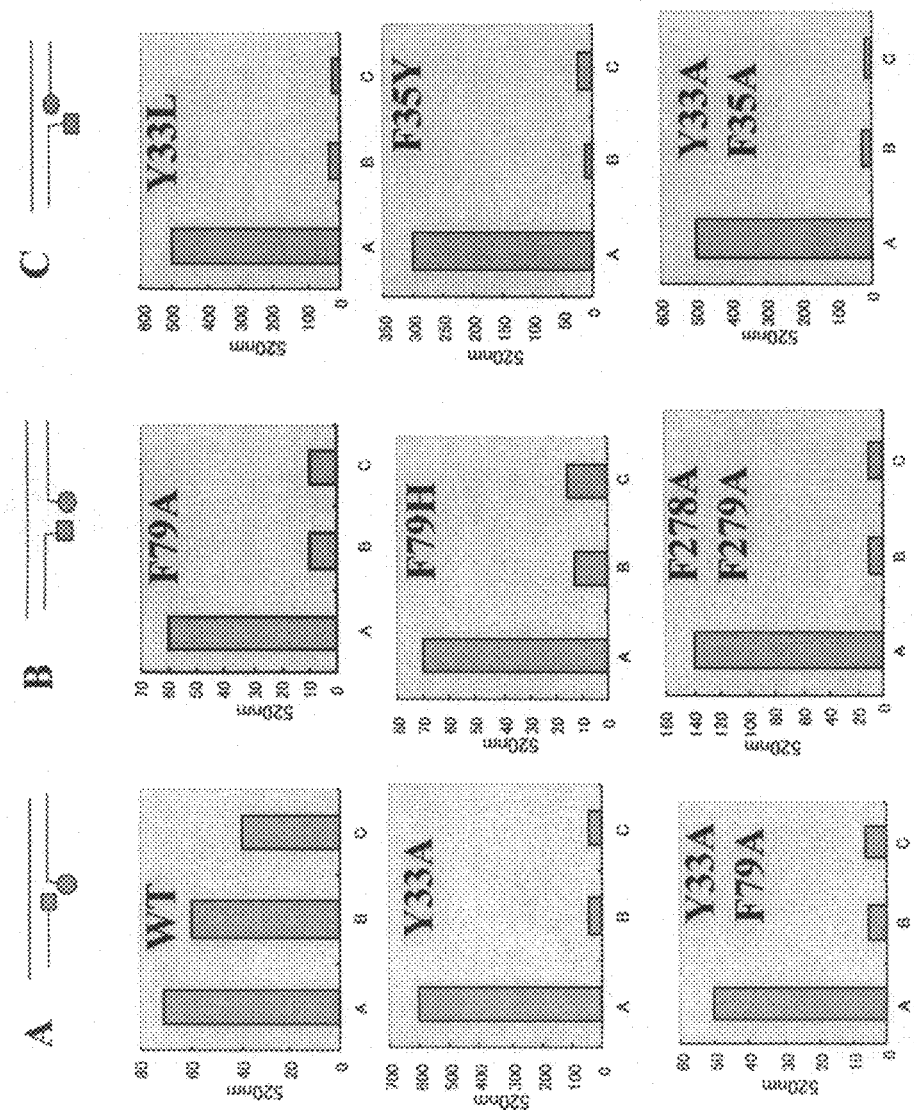
FIG. 15 is a graph showing the results of assaying the activity of the mutant enzyme of the present invention for the substrates prepared in Example 9 based on fluorescence intensity.

The results are shown in FIG. 15.

When TAMRA was bound to the 3' end of the upstream strand B-1, B-2, or B-3, a wild type enzyme and mutant enzymes exhibited weaker activity than the activity on the strand that was not fluorescently labeled at its 3' end. When the amount of the enzyme reached to 50 ng, the activity was detected. The wild type enzyme exhibited a high level of activity on substrates A, B, and C, and the mutant enzymes exhibited a high level of activity selectively on substrate A. Accordingly, polymorphisms can be analyzed via such fluorescent labeling.

Example 10

As the models of the target genes of the polymorphism analysis, the following three types of oligonucleotides were synthesized.

These oligonucleotides differed from each other by the nucleotide at the underlined position, and it was assumed that SNP was present at such position.

```
Template strand (G); 54-mer,
                                          (SEQ ID NO. 43)
5'-GAGCTAGATGTCGGACTCTGCCTCAAGGCGGTAGTCAACGTGCACTC
GAGGTCA-3'

Template strand (C): 54-mer,
                                          (SEQ ID NO. 44)
5'-GAGCTAGATGTCGGACTCTGCCTCAAGCCGGTAGTCAACGTGCACTC
GAGGTCA-3'

Template strand (T): 54-mer,
                                          (SEQ ID NO. 45)
5'-GAGCTAGATGTCGGACTCTGCCTCAAGTCGGTAGTCAACGTGCACTC
GAGGTCA-3'
```

As probes A, the following oligonucleotides were synthesized. These oligonucleotides differed from each other by the nucleotide at the underlined position, and each of such nucleotides was labeled with a different fluorescent dye.

```
Probe A(C): 28-mer,
                                          (SEQ ID NO. 46)
5'-CCTTGAGGCAGAGTCCGACATCTAGCTC-3'
```

The 5' end was labeled with a fluorescent dye (TET).

```
Probe A(G): 28-mer,
                                          (SEQ ID NO. 47)
5'-GCTTGAGGCAGAGTCCGACATCTAGCTC-3'
```

The 5' end was labeled with a fluorescent dye (HEX).

```
Probe A(A): 28-mer,
                                          (SEQ ID NO. 48)
5'-ACTTGAGGCAGAGTCCGACATCTAGCTC-3'
```

The 5' end was labeled with a fluorescent dye (FAM).

The following DNA was synthesized as probe B, and the 3' end thereof was labeled with a quencher (BHQ-1).

```
Probe B (upstream strand b-2): 27-mer,
                                        (SEQ ID NO. 33)
5'-TGACCTCGAGTGCACGTTGACTACCGC-3'
```

The above oligonucleotides were subjected to annealing in the same manner as in Example 4 to prepare the following substrates 1 to 9.

Figure 16:
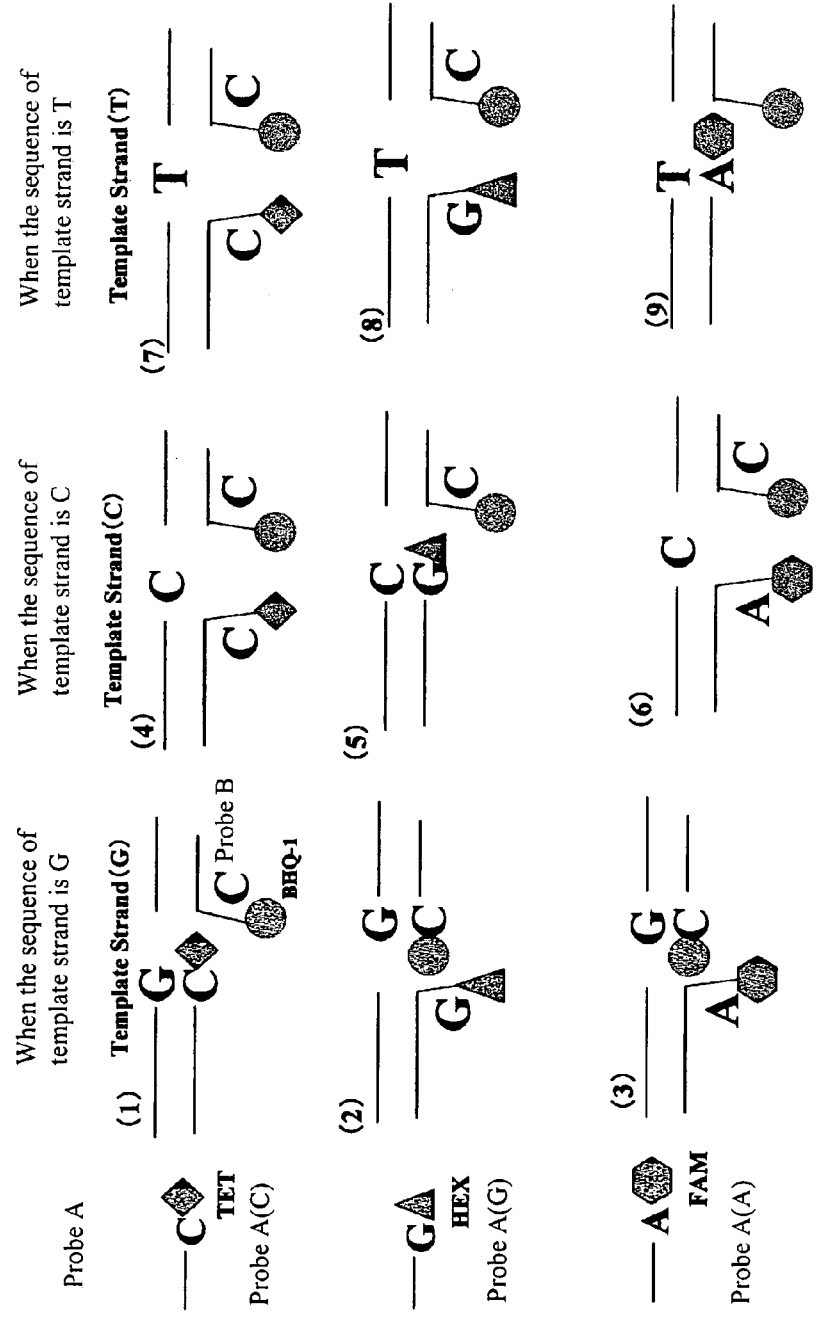
FIG. 16 is a schematic view showing the structure of the substrates prepared in Example 10.

The structures of the substrates generated by such annealing are shown in FIG. 16(1) to (9).

Substrate 1: template strand (G)+probe A(C)+probe B
Substrate 2: template strand (G)+probe A(G)+probe B
Substrate 3: template strand (G)+probe A(A)+probe B
Substrate 4: template strand (C)+probe A(C)+probe B
Substrate 5: template strand (C)+probe A(G)+probe B
Substrate 6: template strand (C)+probe A(A)+probe B
Substrate 7: template strand (T)+probe A(C)+probe B
Substrate 8: template strand (T)+probe A(G)+probe B
Substrate 9: template strand (T)+probe A(A)+probe B Subsequently, 40 pmoles each of fluorescently-labeled substrates were added to 10 µl of 50 mM Tris-HCl buffer (pH 8.0, 15 mM MgCl$_2$, 100 mg/ml bovine serum albumin). Further, 170 ng of wild type enzymes or 400 ng of the mutant enzymes were added to each substrate, and the resultants were allowed to react at 60° C. for 10 minutes. Then, 200 µl of 50 mM Tris-HCl buffer (pH 8.0) was added thereto, and the resultant was placed in ice to terminate the reaction. The excitation wavelength and the emission wavelength varied depending on the fluorescence type. A filter type also varied.

TET: excitation wavelength of 510 nm; emission wavelength of 540 nm; 520 nm filter HEX: excitation wavelength of 520 nm; emission wavelength of 550 nm; 540 nm filter FAM: excitation wavelength of 494 nm; emission wavelength of 525 nm; 500 nm filter The enzyme activity on each substrate was detected by assaying the fluorescence intensities of TET, HEX, and FAM generated at the excitation wavelengths thereof using a fluorescent spectrophotometer (FP-750, JASCO Corporation) through a filter. The enzyme-free samples were designated as the controls, and the values of the controls were subtracted from the values of the enzyme-containing samples. The determined values represent the values of the samples.

Figure 17:
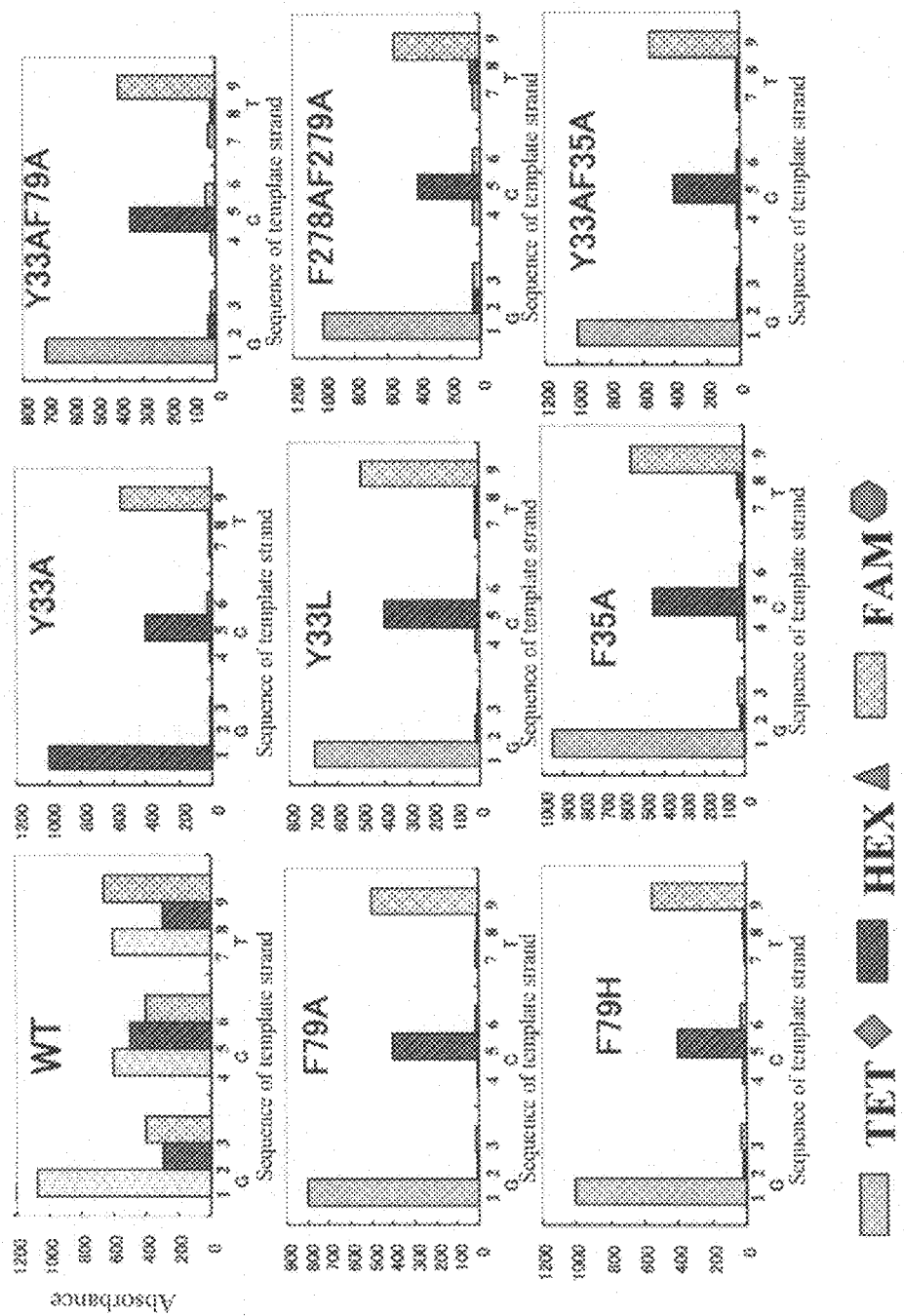
FIG. 17 is a graph showing the results of assaying the activity of the mutant enzyme of the present invention for the substrates prepared in Example 10 based on fluorescence intensity.

The results are shown in FIG. 17.

According to such results, the wild type enzymes exhibited the activity on all the substrates; however, all the mutant enzymes of the present invention exhibited a high level of activity selectively on substrates 1, 5, and 9. This indicates that only probe A(C), probe A(A), and probe A(G) formed base pairs with the template strands and formed 3' projection nick structures (FIG. 16). When TET fluorescence derived from probe A(C) is detected, accordingly, a nucleotide at a position that was assumed to be an SNP site of the template strand is found to be G, for example. Thus, an SNP nucleotide can be identified based on the fluorescence type resulting from the use of the mutant enzyme of the present invention.

Example 11

In the following experiment, the mutant enzyme of the present invention was used in order to determine whether or not an SNP of interest is present in the target gene, when the SNP nucleotide has been identified.

As the models for the target genes of the polymorphism analysis, the following oligonucleotides were synthesized.

In these nucleotide sequences, nucleotide G at the underlined position was assumed to be a normal nucleotide and nucleotide A was assumed to be an SNP nucleotide.

```
Template strand (A): 54-mer,
                                        (SEQ ID NO. 31)
5'-GAGCTAGATGTCGGACTCTGCCTCAAGACGGTAGTCAACGTGCACTC
GAGGTCA-3'

Template strand (G): 54-mer,
                                        (SEQ ID NO. 43)
5'-GAGCTAGATGTCGGACTCTGCCTCAAGGCGGTAGTCAACGTGCACTC
GAGGTCA-3'
```

As probe A, an oligonucleotide having the following sequence in which a 5' end nucleotide corresponding to SNP is T was synthesized. The 5' end thereof was labeled with FAM and the 3' end was labeled with TAMRA.

```
                                        (SEQ ID NO. 49)
Probe A(T): 20-mer, 5'-TCTTGAGGCAGAGTCCGACA-3'
```

As probe B, the following oligonucleotide was used.

```
                                        (SEQ ID NO. 33)
Probe B: 27-mer, 5'-TGACCTCGAGTGCACGTTGACTACCGC-3'
```

Figure 18:
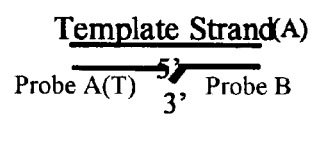
FIG. 18 is a schematic view showing the structure of the substrates prepared in Example 11.
Figure 18:
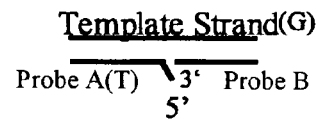

These oligonucleotides were subjected to annealing in the same manner as in Example 4. Thus, substrates having two types of structures shown in FIG. 18 were formed (fluorescent dyes are not shown).

Subsequently, 1 pmole each of fluorescently-labeled substrates were added to 10 µl of 50 mM Tris-HCl buffer (pH 8.0, 15 mM MgCl$_2$, 100 mg/ml bovine serum albumin). Further, 1 ng each of the wild type enzymes and the mutant enzymes were added to each substrate, and the resultants were allowed to react at 60° C. for 5 minutes. Then, 10 µl of 95% formamide, 20 mM EDTA, and 1 mg/ml xylenecyanol were added to terminate the enzyme reaction. The solution was heated to 100° C., quenched on ice, and analyzed by 15% polyacrylamide gel (containing 7 M urea) electrophoresis (PAGE). This electrophoretic pattern was subjected to autoradiography with phospholmager (manufactured by Bio-Rad).

Figure 19:
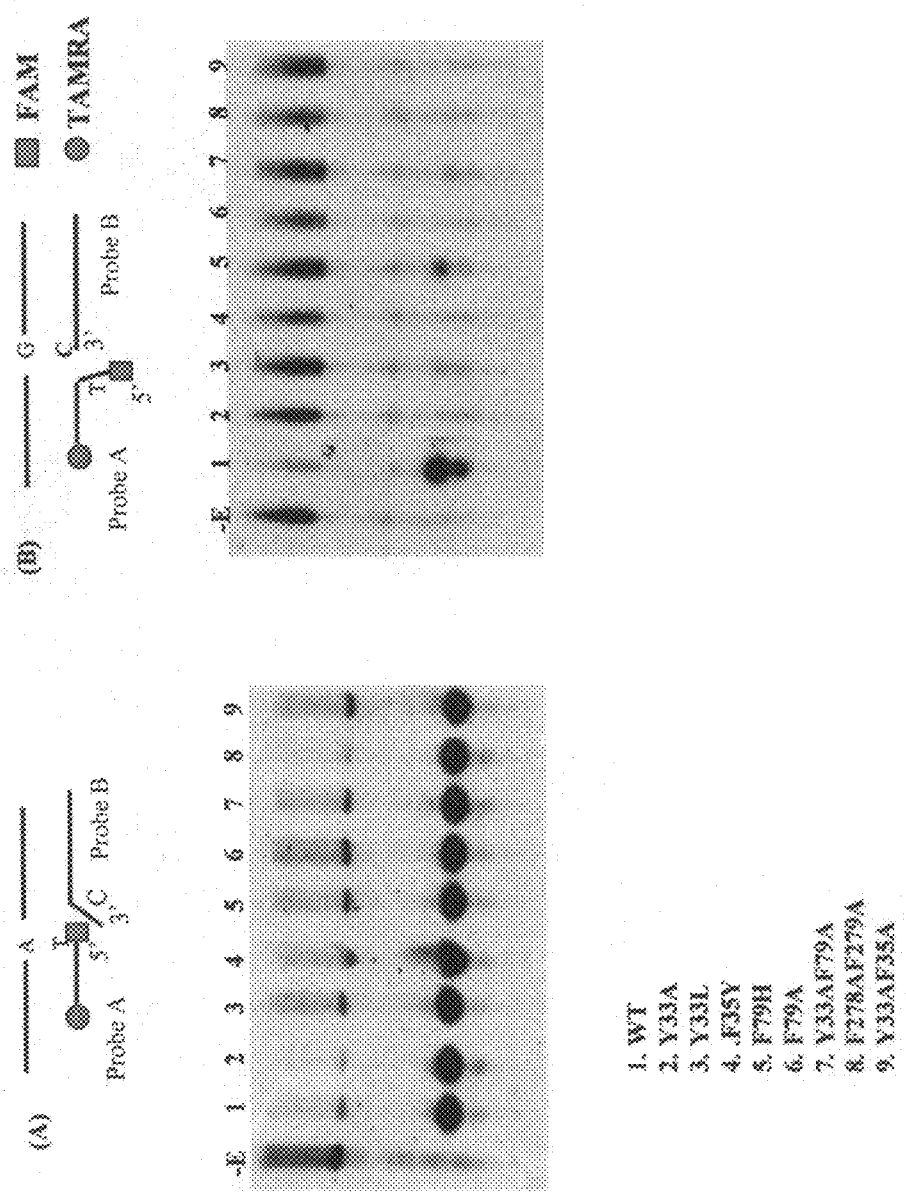
FIG. 19 is an electrophoretic photograph showing the activity of the mutant enzyme of the present invention for the substrates prepared in Example 11.

The results are shown in FIG. 19.

According to such results, the wild type enzymes exhibited the activity on substrates A and B. In contrast, all the mutant enzymes of the present invention exhibited the activity selectively on substrate A, and they did not exhibit any activity level on substrate B or they exhibited very weak activity thereon. When an SNP nucleotide has been identified, probe A having at its 5' end a nucleotide that forms a base pair with the SNP nucleotide may be used. Thus, a 3' projection nick structure is formed, the 5' end of probe A is cleaved with the mutant enzyme of the present invention, and fluorescence derived from the FAN bound to the 5' end is generated. In the absence of SNP, probe A is not cleaved, and no fluorescence is generated. Thus, the presence or absence of SNP can be determined based on the fluorescence (see FIG. 6).

Example 12

In the following experiment, the mutant enzymes of the present invention were used in order to determine the presence or absence of SNP in the target gene and whether or not the detected SNP is of a homozygous or heterozygous type, when an SNP nucleotide has been identified.

As models for the target genes, the following oligonucleotides were synthesized. Nucleotide A at the underlined position was a normal nucleotide, and nucleotide G was an SNP nucleotide.

```
Template strand (A): 54-mer,
                                          (SEQ ID NO. 31)
5'-GAGCTAGATGTCGGACTCTGCCTCAAGACGGTAGTCAACGTGCACTC
GAGGTCA-3'

Template strand (G): 54-mer,
                                          (SEQ ID NO. 43)
5'-GAGCTAGATGTCGGACTCTGCCTCAAGGCGGTAGTCAACGTGCACTC
GAGGTCA-3'
```

The following oligonucleotides were synthesized as probes A. The 5' end of probe A(T) was labeled with FAM and the 3' end was labeled with BHQ-1. The 5' end of probe A(C) was labeled with TET and the 3' end was labeled with BHQ-1.

```
Probe A(T): 20-mer,
                                          (SEQ ID NO. 49)
5'-TCTTGAGGCAGAGTCCGACA-3'

Probe A(C): 20-mer,
                                          (SEQ ID NO. 50)
5'-CCTTGAGGCAGAGTCCGACA-3'

Probe B (upstream strand B-2): 27-mer,
                                          (SEQ ID NO. 33)
5'-TGACCTCGAGTGCACGTTGACTACCGC-3'
```

These oligonucleotides were subjected to annealing in the same manner as in Example 4 to prepare the following substrates 1 to 6.

Figure 21:
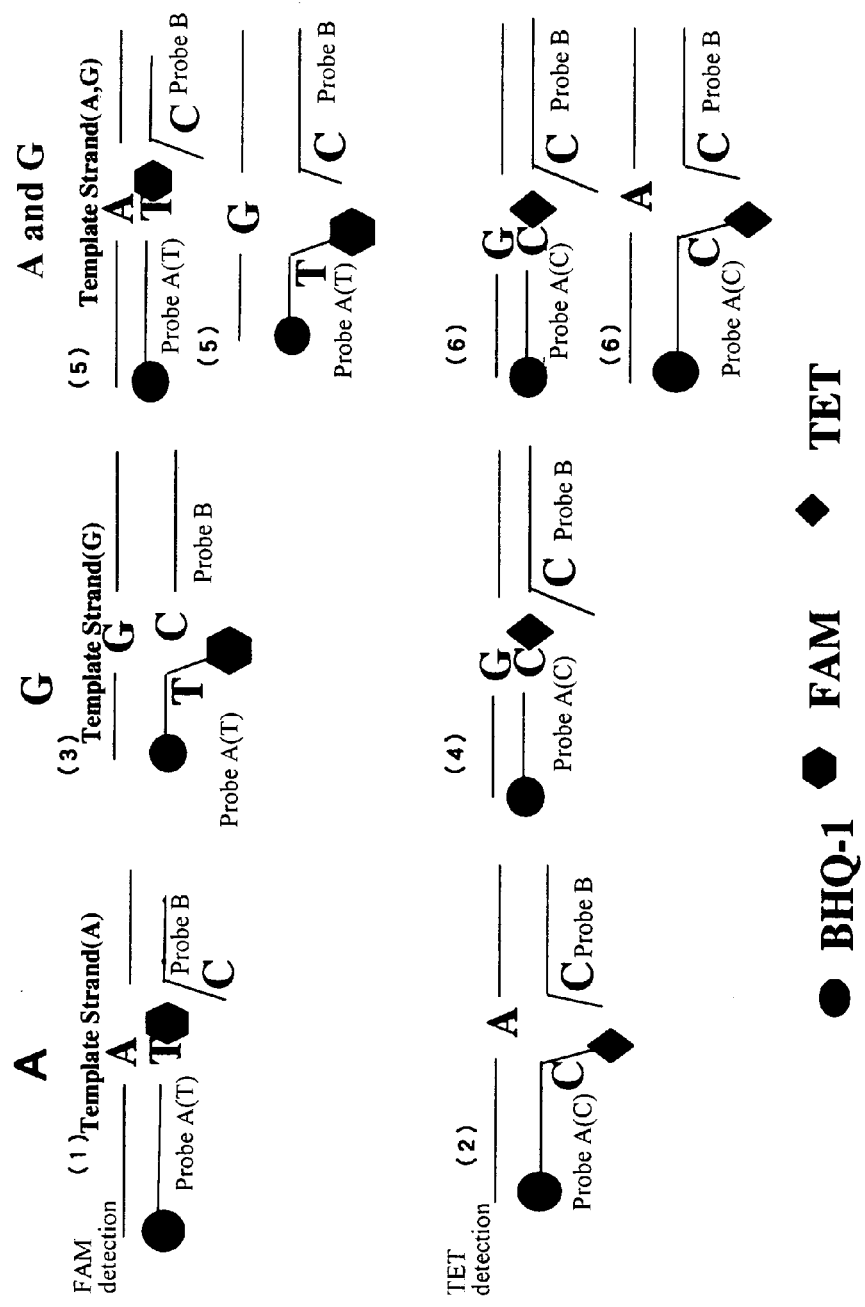
FIG. 21 is a schematic view showing the structure of the substrates prepared in Example 12.

Substrate 1: template strand (A)+probe A(T)+probe B
Substrate 2: template strand (A)+probe A(C)+probe B
Substrate 3: template strand (G)+probe A(T)+probe B
Substrate 4: template strand (G)+probe A(C)+probe B
Substrate 5: template strand (A), template strand (G)+probe A(T)+probe B
Substrate 6: template strand (A), template strand (G)+probe A(C)+probe B The structures of substrates 1 to 6 are shown in FIG. 21.

Subsequently, 10 pmoles each of fluorescently-labeled substrates were added to 10 μl of 50 mM Tris-HCl buffer (pH 8.0, 15 mM MgCl$_2$, 100 mg/ml bovine serum albumin). Further, 10 ng each of the wild type enzymes and the mutant enzymes were added to each substrate, and the resultants were allowed to react at 60° C. for 10 minutes. Then, 200 μl of 50 mM Tris-HCl buffer (pH 8.0) was added thereto, and the resultant was placed in ice to terminate the reaction.

The excitation wavelength and the emission wavelength varied depending on the fluorescence type, as shown below. A filter type also varied.

TET: excitation wavelength of 510 nm; emission wavelength of 540 nm; 520 nm filter FAM: excitation wavelength of 494 nm; emission wavelength of 525 nm; 500 nm filter The enzyme activity on each substrate was detected by assaying the fluorescence intensities of TET, HEX, and FAM at the excitation wavelengths thereof for each substrate using a fluorescent spectrophotometer (FP-750, JASCO Corporation) through a filter. The enzyme-free samples were designated as the controls, and the values of the controls were subtracted from the values of the enzyme-containing samples. The determined values represent the values of the samples.

Figure 22:
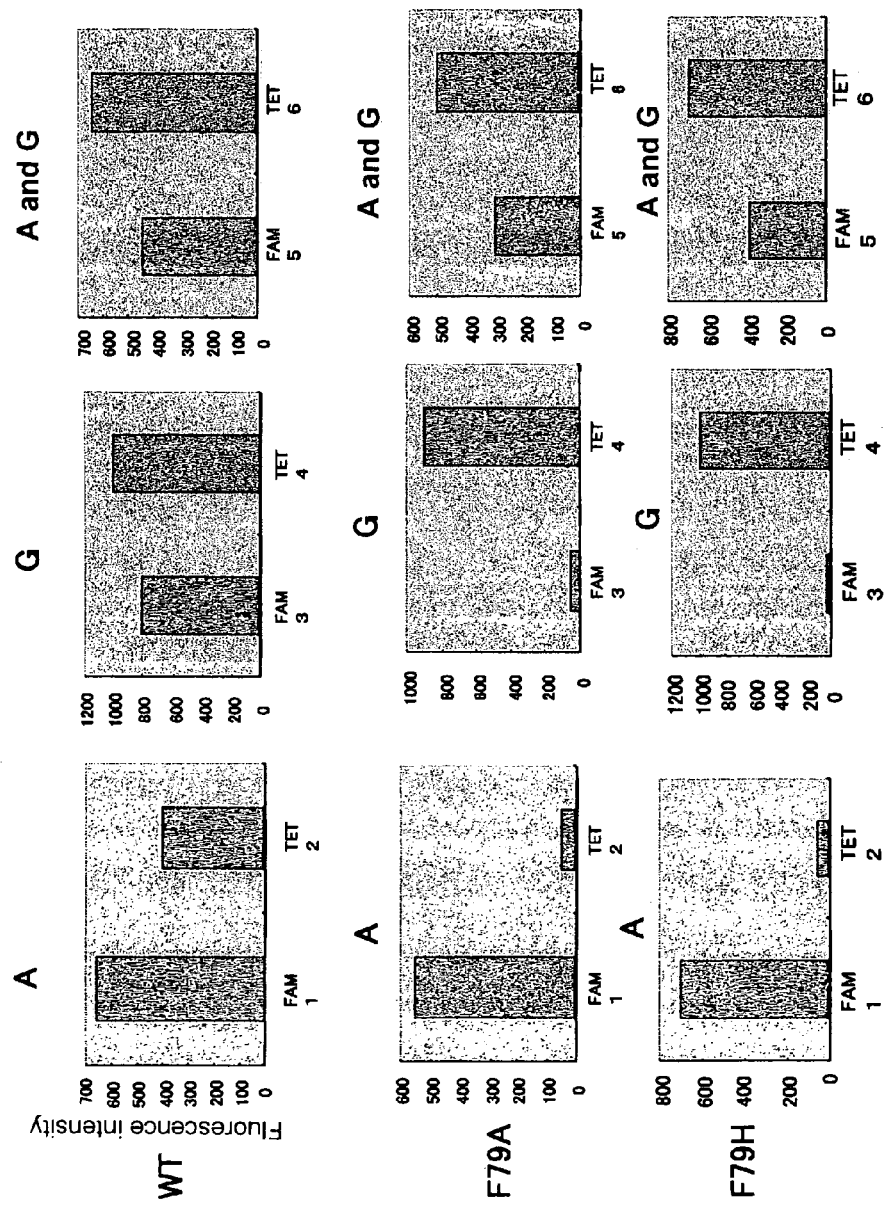
FIG. 22 is a graph showing the results of assaying the activity of wild type enzymes and the mutant enzymes of the present invention (F79A and F79H) for the substrates prepared in Example 12 based on fluorescence intensity.
Figure 23:
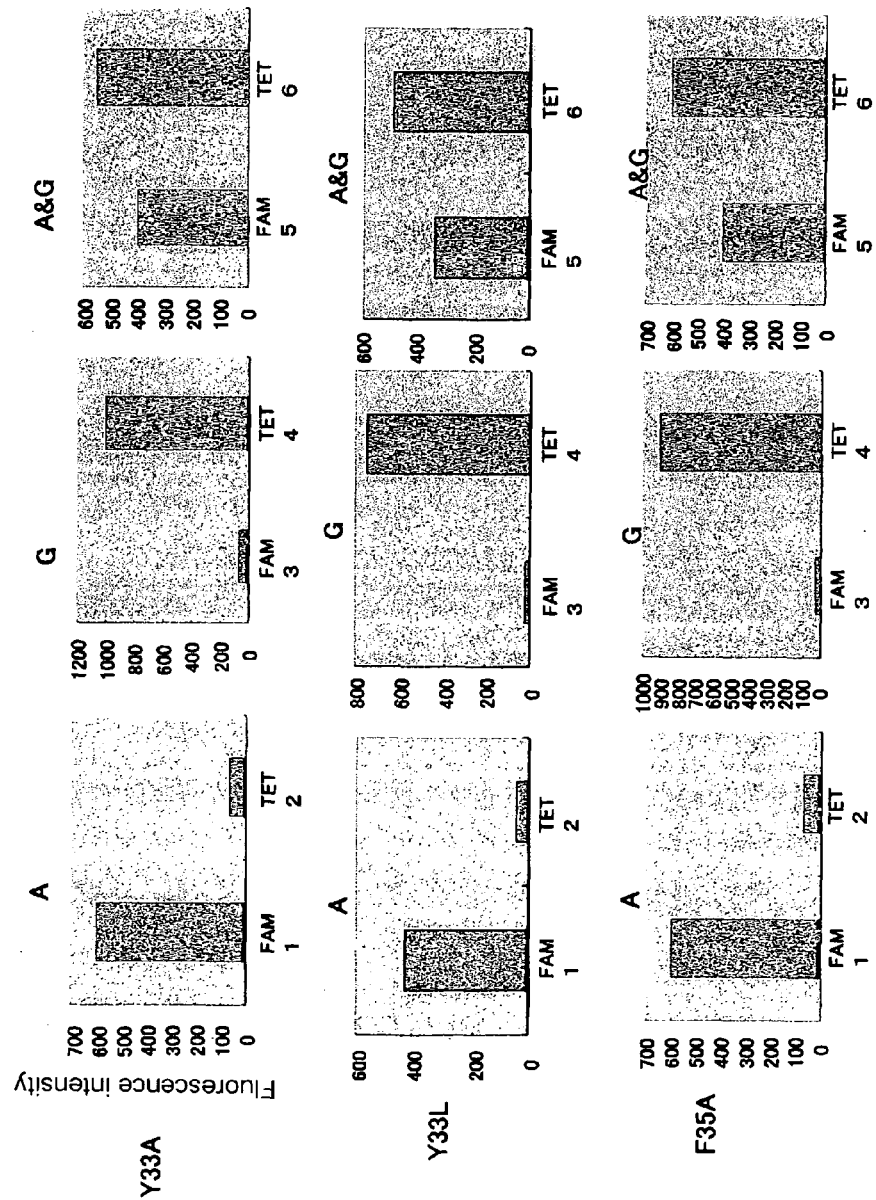
FIG. 23 is a graph showing the results of assaying the activity of the mutant enzymes of the present invention (Y33A, Y33L, and F35A) for the substrates prepared in Example 12 based on fluorescence intensity.
Figure 24:
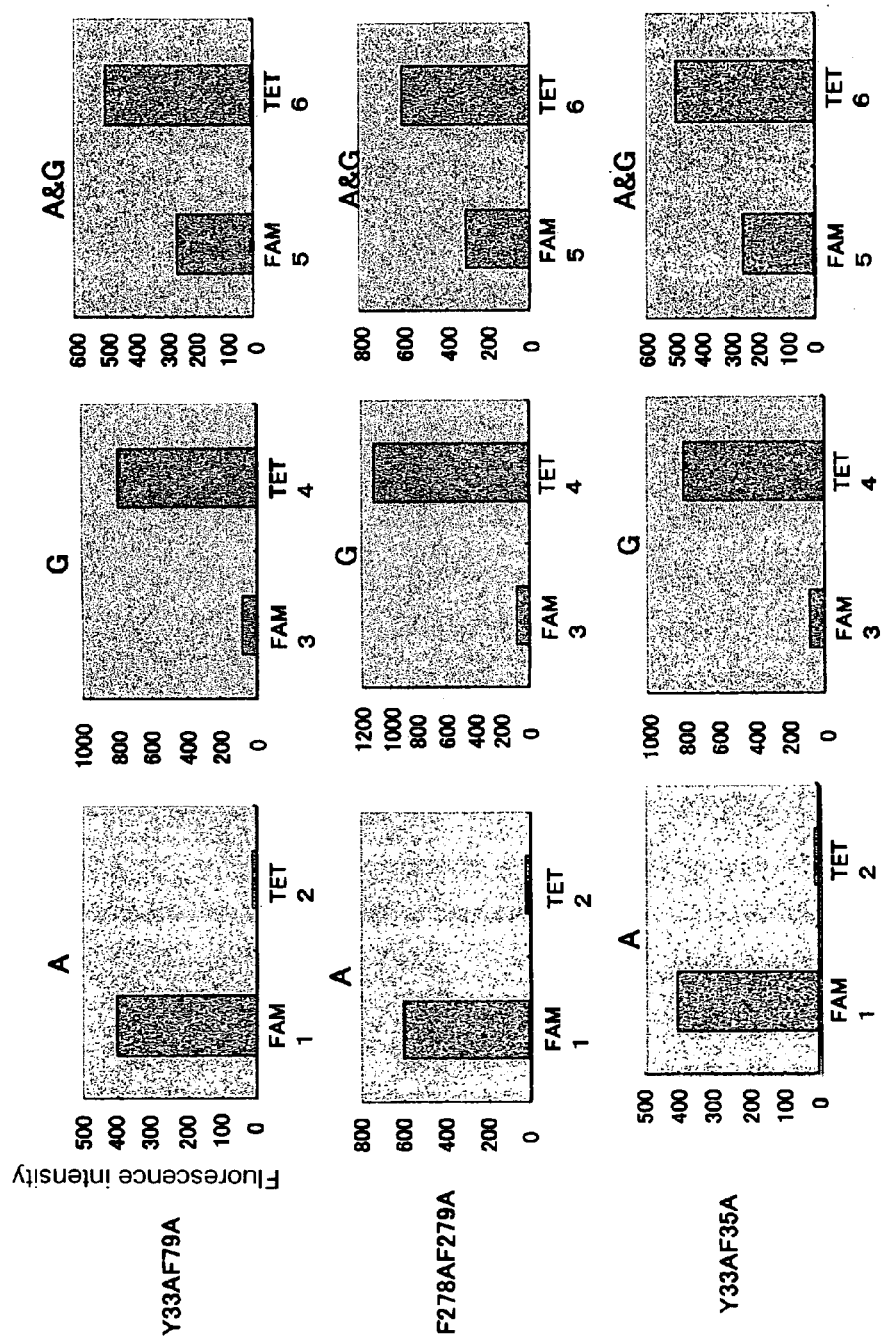
FIG. 24 is a graph showing the results of assaying the activity of the mutant enzymes of the present invention (Y33AF79A, F278AF279A, and Y33AF35A) for the substrates prepared in Example 12 based on fluorescence intensity.

The results are shown in FIGS. 22, 23, and 24.

When the mutant enzymes of the present invention were used, FAM was detected and a high level of activity was observed on substrate 1 in the case of template strand (A). In the case of template strand (G), TET was detected, and a high level of activity was observed on substrate 4. When template strand (A) and (G) were used, FAM and TET were detected, and a high level of activity was observed on substrates 5 and 6. Substrates 1 and 2 are identified when the target gene contains no SNP. Substrates 3 and 4 are identified when SNP is of GG homozygous. Substrates 5 and 6 are identified when SNP is of AG heterozygous. The fact that different fluorescence was detected in each case indicates that the technique of polymorphism analysis according to the present invention is effective for the determination of whether or not the detected SNP is of homozygous or heterozygous as well as for the detection of the presence or absence of SNP. In contrast, differences in the fluorescence intensity of FAM and TET detected on each substrate were not obvious in the case of wild type enzymes.

Example 13

The following experiment is intended to verify that, when a plurality of genome SNPs are simultaneously analyzed (analytical method 5), the sites of the detected SNPs can be identified by changing the nucleotides of the 5' flap strand to be cleaved without changing the length thereof.

The following oligonucleotides were synthesized. Frap strands (C-5) and (C-6) were of the identical length of 14-mer; however, nucleotides at flap sites differed from each other (C-5: CCCAAAAAAAAAAA; C-6: AAAAAAAAAAAAAA).

```
Template strand (A): 54-mer,
                                          (SEQ ID NO. 31)
5'-GAGCTAGATGTCGGACTCTGCCTCAAGACGGTAGTCAACGTGCACTC
GAGGTCA-3'

Upstream strand (B-2): 27-mer,
                                          (SEQ ID NO. 33)
5'-TGACCTCGAGTGCACGTTGACTACCGC-3'

Flap strand (C-5) 43-mer,
                                          (SEQ ID NO. 51)
5'-CCCAAAAAAAAAAATCTTGAGGCAGAGTCCGACATCTAGCTC-3'

Flap strand (C-6): 43-mer;
                                          (SEQ ID NO. 52)
5'-AAAAAAAAAAAAAATCTTGAGGCAGAGTCCGACATCTAGCTC-3'
```

Figure 25:
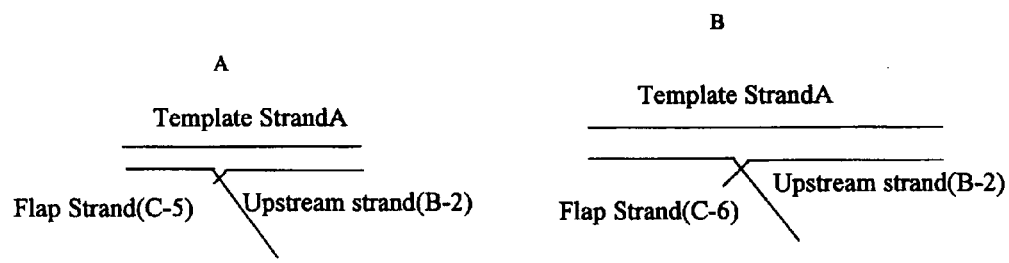
FIG. 25 is a schematic view showing the structure of the substrates prepared in Example 13.

These oligonucleotides were subjected to annealing in the same manner as in Example 4 to prepare the following substrates A and B. The structures of substrates A and B are shown in FIG. 25.

Substrate A: template strand (A)+flap strand (C-5)+upstream strand (B-2)

Substrate B: template strand (A)+flap strand (C-6)+upstream strand (B-2)

Subsequently, 2.5 μmoles each of substrates were added to 190 μl of 50 mM Tris-HCl buffer (pH 8.0, 15 mM MgCl$_2$). Further, 1.5 μmoles of wild type enzymes were added to each substrate, and the resultants were allowed to react at 60° C. for 60 minutes. EDTA (0.2M, 9.5 μl) was added thereto to result in a final concentration of 10 mM for inactivation. Sample solutions containing 5'-cleaved flap portions obtained from the substrates were mixed and then purified using ZipTip (Millipore Corporation) in the following manners a) to k). Thereafter, the molecular weight was assayed using the MALDI-TOF/MS analyzer. The steps of purification and molecular weight assay are shown in the following a) to k).

a) ZipTip (C18, Millipore) is mounted on a P10 pipette and pipetting is carried out five times in 50% AcCN.

b) Pipetting is carried out five times in a 0.1M TEAA solution.

c) The sample (200 µl is removed from 600 µl, dehydrated, and dissolved in 20 µl of sterilized water) is subjected to pipetting approximately 10 times.

d) A 0.1M TEAA solution is suctioned and discharged to the other vessel (performed five times).

e) The DNA sample is eluted in 50% acetonitrile using a microtube.

f) DOWEX-50W-hydrogen beads (SIGMA) substituted with an ammonia form are thinly sprinkled on a parafilm and 7 µl of the eluted sample is spotted thereon.

g) After several times of pipetting, the sample is allowed to stand still for approximately 10 minutes to avoid drying.

h) 1 µl of the matrix (3HPA, a saturated aqueous solution manufactured by Tokyo Kasei) is spotted on the TOF/MS assay plate.

i) 1 µl of the sample was collected while refraining from suctioning beads, the matrix and the sample are mixed on the plate (pipetting).

j) The sample plate is air dried.

k) Assay is carried out using the MALDI-TOF/MS analyzer.

Figure 26:
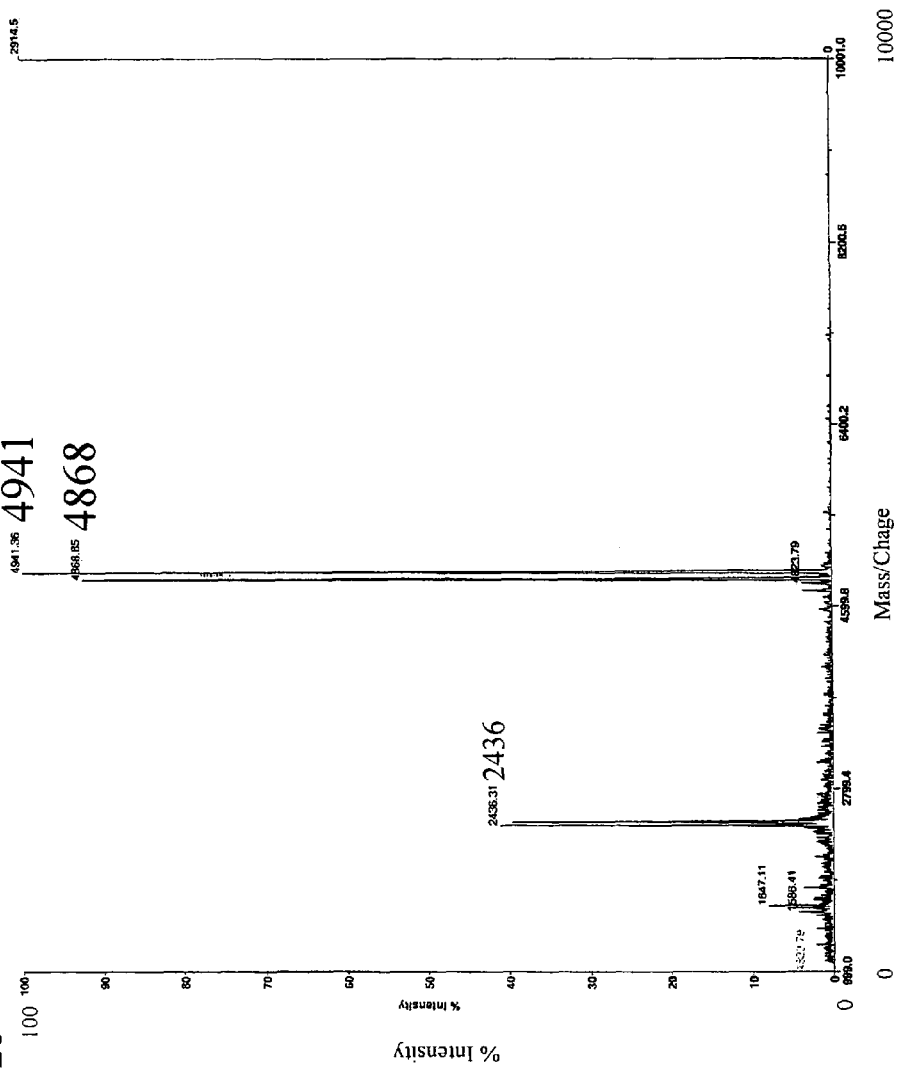
FIG. 26 is a graph showing the results of the mass analysis of each cleaved flap portion obtained by allowing the mutant enzymes of the present invention to act on the substrates prepared in Example 13.
Figure 27:
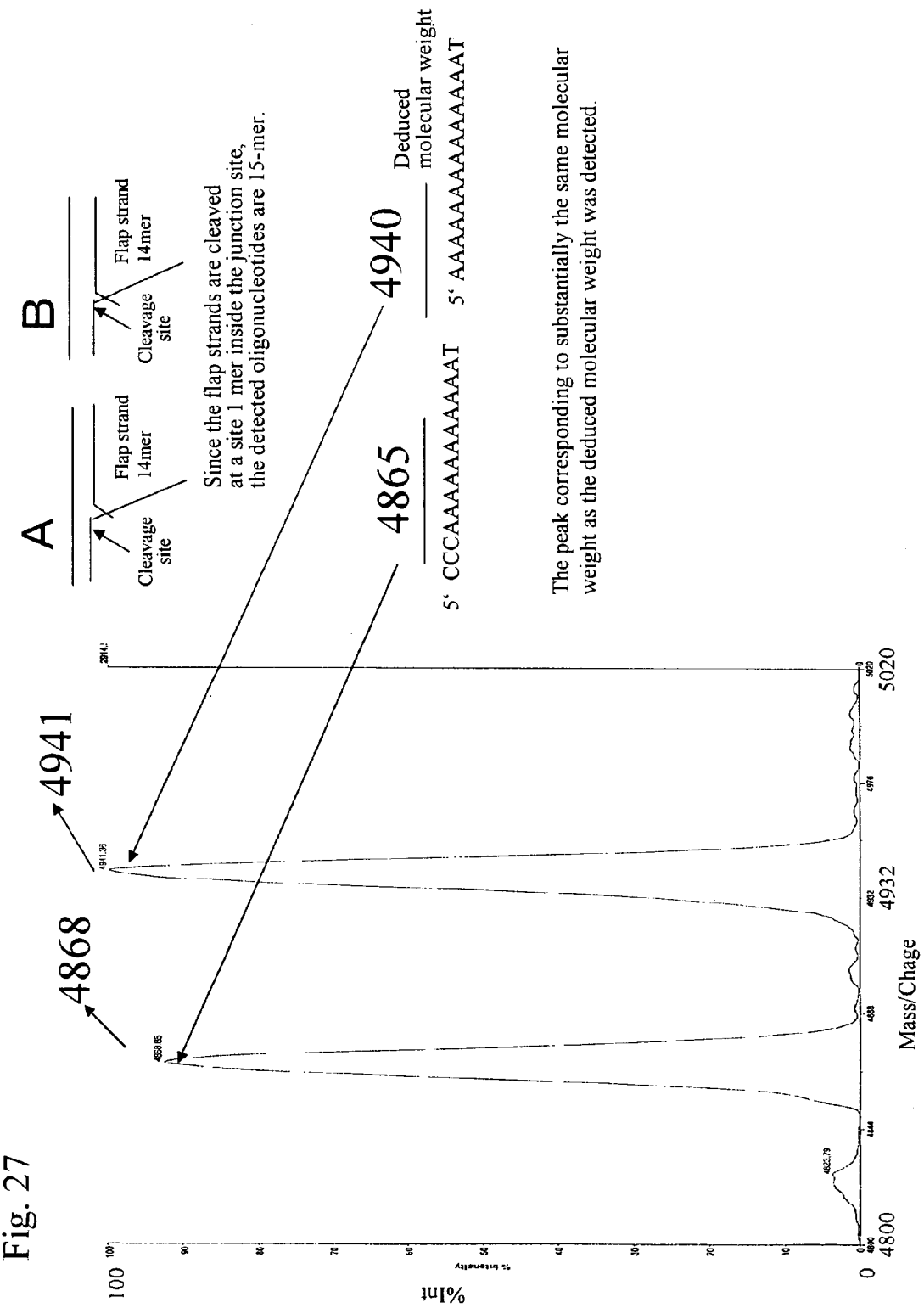
FIG. 27 is a view showing that the molecular weight obtained by the above mass analysis is substantially the same as a putative molecular weight and depicts SEQ ID NO. 55 and SEQ ID NO. 56.

The results are shown in FIGS. 26 and 27.

As a result of the mass analysis, peaks were detected at 4868 and 4911. The value, 4868, is equivalent to the molecular weight, 4865 Da, of the oligonucleotide in which the flap strand of substrate A had been cleaved. The value, 4991, is equivalent to the molecular weight, 4,940 Da, of the oligonucleotide in which the flap strand of substrate B had been cleaved.

No other peak was detected. A cleavage site recognized by the flap endonuclease was located 1-mer inside of the junction site.

Oligonucleotides were purified with the use of ZipTip. The flap strand was degraded by exonuclease, it was detected at a site of a small molecular weight, and it thus did not disturb the sample detection. Downstream strand B was not detected. It was thought that template strand A remained annealed to downstream strand B, this structure was bound to the enzyme, and downstream strand B was thus not detected.

Thus, only the cleaved oligonucleotides could be detected. This indicates that a large number of types of SNPs can be simultaneously analyzed by changing the flap strand length and modifying the sequence.

INDUSTRIAL APPLICABILITY

The flap endonuclease mutant of the present invention has a novel property characterized in that it acts on only the substrate that has a 3' projection structure, and in particular a nick substrate with a 3' projection structure and double-flap substrate shown in FIG. 1, and it hardly cleaves the other substrates for the wild type flap endonuclease. Using the flap endonuclease mutant of the present invention having such substrate specificity, only cases of polymorphism can be detected accurately in the analysis of genetic polymorphism, and this detection can be performed easily.

What is claimed is:

1. An isolated mutant flap endonuclease comprising the amino acid sequence of SEQ ID No. 2, in which one or more amino acids are substituted; wherein said one or more substitutions are selected from the group consisting of:
   (A) the amino acid corresponding to position 33 is alanine or leucine,
   (B) the amino acid corresponding to position 35 is tyrosine,
   (C) the amino acid corresponding to position 79 is alanine or histidine,
   (D) the amino acids corresponding to positions 33 and 79 are both alanine,
   (E) the amino acids corresponding to positions 33 and 35 are both alanine, and
   (F) the amino acids corresponding to positions 278 and 279 are both alanine.

2. A reagent for the analysis of genetic polymorphisms consisting of the mutant flap endonuclease according to claim 1.

* * * * *